(12) United States Patent
Qian et al.

(10) Patent No.: US 10,047,122 B2
(45) Date of Patent: Aug. 14, 2018

(54) PEPTIDE AND PEPTIDE MIMETIC BINDING ANTAGONISTS OF POLO-LIKE KINASE 1 POLO BOX DOMAIN AND METHODS OF USE

(71) Applicant: The United States of America, as represented by the Secretary, Department of Health & Human Services, Washington, DC (US)

(72) Inventors: Wenjian Qian, Frederick, MD (US); Jung Eun Park, Bethesda, MD (US); Christopher C. Lai, Ellicott City, MD (US); James A. Kelley, Silver Spring, MD (US); Kyung S. Lee, Gaithersburg, MD (US); Terrence R. Burke, Jr., Bethesda, MD (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 0 days.

(21) Appl. No.: 14/776,512

(22) PCT Filed: Mar. 14, 2014

(86) PCT No.: PCT/US2014/029071
§ 371 (c)(1),
(2) Date: Sep. 14, 2015

(87) PCT Pub. No.: WO2014/153101
PCT Pub. Date: Sep. 25, 2014

(65) Prior Publication Data
US 2016/0039872 A1    Feb. 11, 2016

Related U.S. Application Data

(60) Provisional application No. 61/784,971, filed on Mar. 14, 2013.

(51) Int. Cl.
| | | |
|---|---|---|
| *A61K 38/00* | (2006.01) | |
| *C07K 7/06* | (2006.01) | |
| *C12N 9/12* | (2006.01) | |
| *C07F 9/141* | (2006.01) | |
| *C07F 9/40* | (2006.01) | |
| *C07K 1/06* | (2006.01) | |

(52) U.S. Cl.
CPC ............ *C07K 7/06* (2013.01); *A61K 38/005* (2013.01); *C07F 9/1411* (2013.01); *C07F 9/4071* (2013.01); *C07K 1/061* (2013.01); *C12N 9/1205* (2013.01); *C07K 2319/21* (2013.01); *C07K 2319/50* (2013.01)

(58) Field of Classification Search
None
See application file for complete search history.

(56) References Cited

U.S. PATENT DOCUMENTS

2012/0065146 A1    3/2012    Burke, Jr. et al.

FOREIGN PATENT DOCUMENTS

| WO | WO 2010/132869 | | 11/2010 |
| WO | WO 2012/142245 | * | 10/2012 |
| WO | WO 2012/142245 A2 | | 10/2012 |

OTHER PUBLICATIONS

Rhodes et al. (downloaded from URL:< http://spdbv.vital-it.ch/TheMolecularLevel/Goodies/Get2NoHistidine.html>).*
Hwang et al. (Org. Lett., 2004, 6 (10), pp. 1555-1556).*
International Search Report and Written Opinion, for PCT/US2014/029071, dated Nov. 17, 2014.
Lu, Fa, et al: "Serendipitous alkylation of a Plk1 ligand uncovers a new binding channel", Nature Chemical Biology, 7(9): 595-601, Jan. 1, 2011. XP055032617, ISSN: 1552-4450, DOI: 10.1038/nchembio.614.
Qian,Wenjian, et al: "Effects on polo-like kinase 1 polo-box domain binding affinities of peptides incurred by structural variation at the phosphoamino acid position", Bioorganic & Medicinal Chemistry, 21(14): 3996-4003. May 26, 2012. XP028595028, ISSN: 0968-0896, DOI: 10.1016/j.BMC.2012.05.036.
Liu, Fa, et al.: "Preparation of orthogonally protectest (25,3R)-2-amino-3-methyl-4-phsphonobutyri c acid (Pmab) as a phosphatase-stable phosphothreonine mimetic and its use in the synthesis of polo-box domain-binding peptides", Tetrahedron, Elsevier Science Publishers, Amsterdam, NL, 65(47): 9673-79. Nov. 21, 2009. XP026696877, ISSN: 0040-4020, DOI: 10.1016/J.TET.2009.09.093.
Qian,Wenjian, et al: "Peptide-based inhibitors of Plk1 polo-box domain containing mono-anionic phosphothreonine esters and their pivaloyloxymethyl prodrugs", Chemistry & Biology, Oct. 1, 2013. 20(10): 1255-64. XP055126907, ISSN: 1074-5521, DOI: 10.1016/J.CHEMBIOL.2013.09.005.
Qian,Wenjian, et al: Retraction of Peptide-based inhibitors of Plk1 polo-box domain containing mono-anionic phosphothreonine esters and their pivaloyloxymethyl prodrugs, Chemistry & Biology, Sep. 18, 2014. 21(9): 1254.

(Continued)

*Primary Examiner* — Jennifer Pitrak McDonald
*Assistant Examiner* — Sergio Coffa
(74) *Attorney, Agent, or Firm* — Bryan D. Zerhusen; Locke Lord LLP

(57) ABSTRACT

The invention provides novel compounds that may serve as anticancer therapeutics. The compounds of the invention bind to polo-like kinases through the polo-box domain. In certain embodiments, the compounds of the invention are POM-protected peptide derivatives. The use of cationic bis-alkyl his residues in combination with a mono POM-protected phophoryl group results in a peptide possessing an overall neutral charge. The peptide derivatives of the invention have achieved both good efficacy and an enhanced bioavailability. The invention also provides methods of use, compositions, and kits thereof. Further, the invention provides a novel method of design and/or synthesis of phosphoryl-derived peptide derivatives useful as therapeutic agents.

30 Claims, 15 Drawing Sheets

(56) References Cited

OTHER PUBLICATIONS

Qian,Wenjian, et al: "Design and synthesis of a reagent for solid-phase incorporation of the phosphothreonine mimetic (2S,3R)-2-amino-3-methyl-4-phosphonobutyric acid (Pmab) into peptides in a bio-reversible phosphonyl-bis-pivaloyloxymethyl (POM) prodrug form". Nov. 1, 2013, Amino Acids, 45(5) 1143-8. XP055126918, ISSN: 0939-4451, DOI: 10.1007,s00726-013-1567-1.
Accession No. O00444.3 GI:160113150 RecName: Full=Serine/threonine-protein kinase PLK4; AltName: Full=Polo-like kinase 4; Short=PLK-4; AltName: Full=Serine/threonine-protein kinase 18; AltName: Full=Serine/threonine-protein kinase Sak.
Accession No. P53350.1 GI: 1709658 RecName: Full=Serine/threonine-protein kinase PLK1; AltName: Full=Polo-like kinase 1; Short=PLK-1; AltName: Full=Serine/threonine-protein kinase 13; Short=STPK13.
Accession No. Q07832.2 GI: 1709659 RecName: Full=Serine/threonine-protein kinase PLK1; AltName: Full=Polo-like kinase 1; Short=PLK-1; AltName: Full=Serine/threonine-protein kinase 13; Short=STPK13.
Accession No. Q62673.1 GI: 12230396 RecName: Full=Serine/threonine-protein kinase PLK1; AltName: Full=Polo-like kinase 1; Short=Plk-1.
Accession No. Q9H4B4.2 GI:5133882 RecName: Full=Serine/threonine-protein kinase PLK3; AltName: Full=Cytokine-inducible serine/threonine-protein kinase; AltName: Full=FGF-inducible kinase; AltName: Full=Polo-like kinase 3; Short=PLK-3; AltName: Full=Proliferation-related kinase.
Accession No. Q9NYY3.3 GI:22096374 RecName: Full=Serine/threonine-protein kinase PLK2; AltName: Full=Polo-like kinase 2; Short=PLK-2; Short=hPlk2; AltName: Full=Serine/threonine-protein kinase SNK; Short=hSNK; AltName: Full=Serum-inducible kinase.
Accession No. XP_001163585.1 GI:114661620 Predicted: polo-like kinase isoform 1 [Pan troglodytes].
Collaborative Computational Project, No. 4. The CCP4 suite: programs for protein crystallography. Acta Crystallogr D Biol Crystallogr. Sep. 1, 1994;50(Pt 5):760-3. PubMed PMID: 15299374.
Adams, P.D. et al. "Phenix, a comprehensive python-based system for macromolecular structure solution", Acta Crystallogr. D Biol. Crystallogr. 66, 213-21.
Allentoff, A.; Mandiyan, S.; Liang, H.; Yuryev, A.; Vlattas, I.; Duelfer, T.; Sytwu, I.-L; Wennogle, L. Understanding the cellular uptake of phosphopeptides. Cell Bio chem. Biophys. 1999, 31, 129-140.
Arrendale, A.; Kim, K.; Choi, J.; Li, W.; Geahlen, R. L.; Borch, R. F., et al, "Synthesis of a phosphoserine mimetic prodrug with potent 14-3-3 protein inhibitory activity", Chem. Biol 2012, 19, 764-771.
Attard, T. J.; O'Brien-Simpson, N.; Reynolds, E. C., et al, "Synthesis of phosphopeptides in the fmoc mode", Int. J. Pept. Res. Ther. 2007, 13, 447-468.
Berge et al. (1977) "Pharmaceutical Salts", J. Pharm. Sci. 66:1-19.
Blume-Jensen, P.; Hunter, T. et al, "Oncogenic kinase signaling", Nature 2001, 411, 355-36.
Boutselis, I. G.; Yu, X.; Zhang, Z.-Y.; Borch, R. F., "Synthesis and cell-based activity of a potent and selective protein tyrosine phosphatase 1B inhibitor prodrug", J. Med. Chem. 2007, 50, 856-864.
Burke, T. R., Jr.; Lee, K.; "Phosphotyrosyl mimetics in the development of signal transduction inhibitors", Acc. Chem. Res. 2003, 36, 426-433.
Eisele, F.; Owen, D. J.; Waldmann, H., "Peptide conjugates as tools for the study of biological signal transduction", Bioorg Med Chem 1999, 7, 193-224.
Elia, A. E. H. and Yaffe, M. B. (2004) Phosphoserine/Threonine Binding Domains, in Modular Protein Domains (eds G. Cesareni, M. Gimona, M. Sudol and M. Yaffe), Wiley-VCH Verlag GmbH & Co. KGaA, Weinheim, FRG. doi: 10.1002/3527603611.ch8, (p. 163-179).

Goguen, B. N.; Aemissegger, A.; Imperiali, B, "Sequential Activation and deactivation of protein function using spectrally differentiated caged phosphoamino acids", J. Am. Chem. Soc. 2011, 133, 11038-11041.
Hanisch, A. et al., "Different Plk1 functions show distinct dependencies on polo-box domain-mediated targeting", Mol. Biol. Cell 17, 448-459 (2006).
Hecker, S. J.; Erion, M. D., "Produgs of phosphates and phosphonates", J. Med. Chem. 2008, 51, 2328-2345.
Hwang, Y.; Cole, P.A., "Efficient synthesis of phosphorylated prodrugs with bis(POM)-phosphoryl chloride", Org. Lett. 2004, 6, 1555-1556.
Kraulis, P.J., "Molscript: a program to produce both detailed and schematic plots of protein structures", J. Appl. Crystallogr. 24, 946-950 (1991).
Ladbury, J. E., "Protein-protein recognition in phosphotyrosine-mediated intracellular signaling", In: Waksman G. (eds) Proteomics and Protein-Protein Interactions. Protein Reviews, Rev. 2005, 3, pages, 165-184 Springer, Boston, MA.
Liu et al. Identification of high affinity polo-like kinase 1 (Plk1) polo-box domain binding peptides using oxime-based diversification. ACS Chem Biol 2012. 7(5): 805-10.
Liu et al. Peptoid-Peptide hybrid ligands targeting the polo box domain of polo-like kinase 1. Chembiochem 2012. 13(9): 1291-1296.
Liu, F. et al., "Preparation of orthogonally protected (2S,3R)-2-amino-3-methyl-4-phosphonobutryic acid (Pmab) as a phosphatase-stable phosphothreonine mimetic and its use in the syntheses of polo-box domain-binding peptides", Tetrahedron 65, 9673-9679 (2009).
Liu, F.; Serendipitous alkylation of a Plk1 ligand uncovers a new binding channel. Nat Chem Biol. Jul. 17, 2011;7(9):595-601. doi: 10.1038/nchembio.614. PubMed PMID: 21765407; PubMed Central PMCID: PMC3158281.
Liu, W.-Q.; Vidal, M.; Mathe, C; Perigaud, C; Garbay, C., "Inhibition of the ras-dependent mitogenic pathway by phosphopeptide prodrugs with antiproliferative properties", Bioorg. Med. Chem. Lett. 2000, 10, 669-672.
Liu, W.-Q.; et al, "Structure-activity relationships of small phosphopeptides, inhibitors of grb2 SH2 domain, and their prodrugs", C. J. Med. Chem. 2004, 47, 1223-1233.
Lu, C. H. S.; Liu, K.; Tan, L. P.; Yao, S. Q., "Current Chemical Biology tools for studying protein phosphorylation and dephosphorylation", Chem. Eur. J. 2012, 18, 28-39.
Mandal, P. K.; Gao, F.; Lu, Z.; Ren, Z.; Ramesh, R.; Birtwistle, J. S.; Kaluarachchi, K. K.; Chen, X.; Bast, R. C; Liao, W. S.; McMurray, J. S., "Potent and selective phosphopeptide mimetic prodrugs targeted to the SRC homology 2 (SH2) domain of signal transducer and activator of transcription 3", J. Med. Chem. 2011, 54, 3549-3563.
Mandal, P. K.; Liao, W. S. L.; McMurray, J.S.; "Synthesis of phosphatase-stable, cell-permeable peptidomimetic pro-drugs that target the SH2 domain of staf3", Org Lett. 2009, 11, 3394-3397.
Mathe, C; Perigaud, C; Gosselin, G.; Imbach, J.-L., "Phosphopeptide prodrug bearing an s-acyl-2-thioethyl enzyme-labile phosphate protection", J. Org. Chem. 1998, 63, 8547-8550.
McMurray, J. S.; Coleman, D. R. I. V.; Wang, W.; Campbell, M. L., "The synthesis of phosphopeptides", Biopolymers (PEPT SCI) 2001, 60, 3-31.
McRee, D.E. , "Xtalview/xfit—a versatile program for manipulating atomic coordinates and electron density", J. Struct. Biol. 125, 156-65 (1999).
Minor, W. et al., "HKL-3000: the integration of data reduction and structure solution—from diffraction images to an initial model in minutes", Acta Crystallogr. D Biol. Crystallogr. 62, 859-66 (2006).
Nair, S. A.; Lee, B.; Hangauer, D. G., "Synthesis of orthogonally protected l-homocysteine and l-2-amino-4-phosphonobutanoic acid from L-homoserine", Synthesis 1995, 810-814.
Navaza, J., "Implementation of molecular replacement in AMORE", Acta Crystallogr. D Biol. Crystallogr. 57, 1367-72 (2001).
Otaka, A.; Mitsuyama, E.; Kinoshita, T.; Tamamura, H.; Fujii, N., "Stereoselective synthesis of CF2-substituted phosphothreonine

(56) References Cited

OTHER PUBLICATIONS mimetics and their incorporation into peptides using newly developed deprotection procedures", J. Org. Chem. 2000, 65, 4888-4899.

Ottinger, E. A.; Shekels, L. L.; Bernlohr, D. A.; Barany, G., "Synthesis of phosphotyrosine-containing peptides and their use as substrates for protein tyrosine phosphatases", Biochemistry 1993, 32, 4354-4361.

Panigrahi, K.; Eggen, M.; Maeng, J.-H.; Shen, Q.; Berkowitz, D. B., "The a a-difluorinated phosphonate l-pser-analogue: an accessible chemical tool for studying kinase-dependent signal transduction in vitro, and in living cells", Chem. Biol. 2009, 16, 928-936.

Perich, J. W., "Efficient Fmoc/solid-phase synthesis of abu(p)-containing peptides using fmoc-abu(PO3Me2)-OH", Int. J. Pept. Protein Res. 1994, 44, 288-294.

Richter, S.; Bergmann, R.; Pietzsch, J.; Ramenda, T.; Steinbach, J.; Wuest, F., "Fluorine-18 labeling of phosphopeptides: a potential approach for the evaluation of phosphopeptide metabolism in vivo", Biopolymers (PEPT SCI) 2009, 92, 479-488.

Rogers, L. D.; Foster, L., "Phosphoproteomics-finally fulfilling the promise", J. Mol. BioSyst. 2009, 5, 1122-1129.

Rothman, D. M.; Vazguez, M. E.; Vogel, E. M., Imperiali, B., "Cages phospho-amino acid building blocks for solid-phase peptide synthesis", J. Org. Chem. 2003, 68, 6795-6798.

Saulnier et al., "An efficient method for the synthesis of Guanidino prodrugs", (1994), Bioorganic and Medicinal Chemistry Letters, vol. 4, p. 1985.

Schultz, C., "Prodrugs of biologically active phosphate esters", Bioorg. Med. Chem. 2003, 11, 885-898.

Seong, Y.S. et al., "A spindle checkpoint arrest and a cytokinesis failure by the dominant-negative polo-box domain of plk1 in U-2 OS cells", J. Biol. Chem. 277, 32282-32293 (2002).

Shapiro, G.; Buechler, D.; Ojea, V.; Pombo-Villar, E.; Ruiz, M.; Weber, H. P., "Synthesis of both d- and l-fmoc-abu[PO(OCH2CH=Ch2)2]-OH for solid phase phosphonopeptide synthesis", Tetrahedron Lett. 1993, 34, 6255-6258.

Srivastva, DN, "Bioreversible phosphate protective groups: Synthesis and stability of model acyloxymethyl phosphates", Bioorganic Chemistry, vol. 12, Issue 2, Mar. 1984, pp. 118-129.

Stankovic, C. J.; et al., "The role of 4-phosphonodifluoromethyl- and 4-phosphono-phenylalanine in the selectivity and cellular uptake of sh2 domain ligands", Bioorg. Med. Chem. Lett. 1997, 7, 1909-1914.

Strebhardt, K. et al., "Targeting polo-like kinase 1 for cancer therapy", Nat. Rev. Cancer 6, 321-330. (2006).

Toth, G. K.; Kele, Z.; Varadi,G.; "Phosphopeptides—chemical synthesis, analysis, outlook and limitations", Curr. Org. Chem. 2007, 11, 409-426.

Van de Weerdt, W. B. C. M.; Littler, D. R.; Klompmaker, R.; Huseinovic, A.; Fish, A.; Perrakis, A.; Medema, R. H. Biochim. Biophys. Acta, 2008, 1783, 1015-1022.

Yaffe, M. B., "Phosphotyrosine-binding domains in signal transduction", Nat. Rev. Mol. Cell Biol. 2002, 3, 177-186.

Yun SM, Moulaei ,et al., Structural and functional analyses of minimal phosphopeptides targeting the polo-box domain of polo-like kinase 1. Nat Struct Mol Biol. Aug. 2009;16(8):876-882. doi: 10.1038/nsmb.1628. Epub Jul. 13, 2009. Erratum in: Nat Struct Mol Biol. Apr. 2011;18(4):516. PubMed PMID: 19597481; PubMed Central PMCID: PMC2721907.

Zhao, S.; Etzkorn, F.A., "A phosphorylated prodrug for the inhibition of pin1", Bioorg. Med. Chem. Lett. 2007, 17, 6615-6618.

\* cited by examiner

| | |
|---|---|
| FIG. 9A | FIG. 9A |
| | FIG. 9B |
| | FIG. 9C |

| Entry | No. | $R^1$ | $R^2$ | $R^3$ | $R^b$ | ELISA,$IC_{50}$/nM[b] |
|---|---|---|---|---|---|---|
| 0 | 4j (Qian30) | H | H | OH | absent | 3.0 |
| 1 | Qian48 | H | H | OH | ⤳⁀⁀⁀OH | 1.3 |
| 2 | Qian113 (S/A mutant of Qian048) | H | H | H | ⤳⁀⁀⁀OH | >300 |
| 3 | Qian49 | H | H | OH | ⤳⁀⁀⁀(OH)(OH) | ~1.2 |

FIG. 9B

| | | | | | |
|---|---|---|---|---|---|
| 4 | Qian50 | H | H | OH | (methoxy chain) | 1.2 |
| 5 | Qian62 (S/A mutant of Qian50) | H | H | H | (methoxy chain) | >300 |
| 6 | Qian51 | H | H | OH | (carboxylic acid chain) | 1.3 |
| 7 | Qian52 | H | H | OH | (alkenyl chain) | 3.9 |
| 8 | Qian53 | H | H | OH | (thiophene chain) | 4.7 |
| 9 | Qian54 | H | H | OH | (furan chain) | 6.1 |

| | | | | | |
|---|---|---|---|---|---|
| 10 | Qian55 | H | H | OH | ![Me group] | 4.8 |
| 11 | Qian63 | H | H | OH | ![(CH2)7Ph] | 39 |
| 12 | Qian74 | H | H | OH | ![CH2CH(OH)CH2OH chain] | 1.2 |
| 13 | Qian114 (S/A mutant of Qian74) | H | H | H | ![CH2CH(OH)CH2OH chain] | 1.54 |
| 14 | Qian075 | H | H | OH | ![CH2CH(OH)CH2OH chain] | 1.9 |
| 15 | Qian076 | H | H | OH | ![CH2CH(OH)CH2OH chain] | 2.6 |
| 16 | Qian077 | H | H | OH | ![CH(OH)CH(OH)CH2OH chain] | 15.1 |

FIG. 9C

PEPTIDE AND PEPTIDE MIMETIC BINDING ANTAGONISTS OF POLO-LIKE KINASE 1 POLO BOX DOMAIN AND METHODS OF USE

RELATED APPLICATIONS

This application claims the benefit of and priority to U.S. Provisional Application No. 61/784,971, filed on Mar. 14, 2013, and International Patent Application Serial No. PCT/US2014/029071 filed on Mar. 14, 2014 the contents of which are incorporated herein by referenced.

STATEMENT OF RIGHTS TO INVENTIONS MADE UNDER FEDERALLY SPONSORED RESEARCH

This work was supported by the Intramural Research Program of the National Institutes of Health. The U.S. government has certain rights in the invention.

BACKGROUND

Found in various eukaryotic organisms, polo-like kinases (collectively, Plks) are a conserved subfamily of Ser/Thr protein kinases that play critical roles in cell proliferation. Plks are characterized by the presence of a highly conserved C-terminal polo-box domain (PBD) composed of two structurally-related PB1 (residues 411-489 in Plk1) and PB2 (residues 511-592) motifs. Multiple forms of Plks, designated Plk1, Plk2/Snk, Plk3/Prk/Fnk, and Plk4/Sak, exist in mammals. Plk4 is the most distantly related member of the Plk subfamily and one of the two Plk4 variants, Sak-a, contains only the PB1 motif near the end of an unusually long C-terminal extension. Among the Plks, Plk1 has been studied most extensively because of its ability to override cellular checkpoints and induce genetic instability, leading to oncogenic transformation of human cells. Not surprisingly, Plk1 is overexpressed in a broad spectrum of human cancers and has been proposed as a new prognostic marker for many types of malignancies.

Furthermore, interference with Plk1 function induces apoptotic cell death in most tumor cells, but not in normal cells, and reduces tumor growth in mouse xenograft models. A Plk1 inhibitor known as BI 6727 (volasertib) is presently undergoing clinical trials for the treatment of various human cancers, including acute myeloid leukemia. In contrast to the role of Plk1 in cell proliferation and tumorigenesis, the two most closely related kinases, Plk2 and Plk3, appear to play a role in checkpoint-mediated cell cycle arrest to ensure genetic stability and prevent oncogenic transformation. Thus, specific inhibition of Plk1, but not Plk2 or Plk3, is critically important for anti-Plk1 cancer therapy.

The PBD of Plk1 plays a critical role in proper subcellular localization and mitotic functions of Plk1 by interacting with phosphorylated Ser/Thr peptides with the invariable Ser residue at the −1 position (S-p-S/T motif). Crystal structures of the Plk1 PBD in complex with artificial phosphopeptides optimized for PBD binding have revealed that the PB1 and PB2 motifs have identical folds described as β6α (a six-stranded anti-parallel β-sheet and an α-helix) and form a hetero-dimeric phosphopeptide-binding module.

The phosphopeptide binds to a cleft formed between PB1 and PB2 and interacts with key amino acid residues from both polo-boxes. His538 and Lys540 from PB2 are pivotal for electrostatic interactions with the negatively charged phosphate group of phospho-Ser/Thr (p-Ser/Thr) residue, whereas Trp414 from PB1 is critical for the selection of Ser at the −1 position by engaging in two hydrogen bonding interactions and van der Waals interactions with the Ser-1 residue. These residues are conserved in the PBDs of Plk1, Plk2, and Plk3 (in short, Plk1-3), attesting to their importance (Plk4 has a distinct binding module and forms a homodimer through a motif called cryptic polo-box).

By examining PBD-binding phosphopeptides, the phosphopeptide "PLHSpT" was identified that specifically interacts with the Plk1 PBD with a high affinity, but not with the two closely-related Plk2 and Plk3 PBDs. Based on this peptide sequence, peptides with high PBD-binding affinity may be designed and prepared; however, even with high PBD-binding affinity, it is difficult for the peptides to achieve activity in whole-cell systems, possibly due to poor bioavailability arising from poor solubility or limited membrane transport (or both). There is a need in the art to design and prepare PBD-binding peptides with improved pharmaceutical properties, including increased bioavailability.

SUMMARY OF THE INVENTION

The invention involves design and synthesis of peptide-mimetic ligands of the polo-like kinase 1 (Plk1) which is a critical regulator of mitotic events and cellular proliferative potential. In particular, the invention provides novel compounds that inhibit polo-like kinases by binding to the polo-box domain.

In one aspect, the invention provides novel PBD-binding peptides (also referred to as "peptide derivatives") that may serve as anti-cancer therapeutics. The novel PBD-binding peptides of the invention offer a solution to the bioavailability problem that has been observed with the existing peptide compositions. Specifically, without wishing to be bound by any particular theory, it is believed that bioavailability of the peptides is enhanced by attaching a pivaloyloxymethyl ("POM") group and/or by utilizing intramolecular charge masking. The peptides of the invention have achieved both good efficacy and an enhanced bioavailability. The invention also provides methods of use and kits thereof. In a further aspect, the invention provides a novel method of design or synthesis (or both) of phosphoryl-derived peptide derivatives useful as therapeutic agents.

In certain embodiments, the novel compounds are peptide derivatives that contain 4-5 residue peptides, comprising, such as, a pThr, pSer, or Pmab (i.e., phosphonomethylamino butyric acid) residue.

The peptide derivatives in accordance with the invention demonstrate good cellular uptake. Certain peptide derivatives of the invention demonstrate good cellular efficacy. In certain embodiments, the peptide derivatives in accordance with the invention demonstrate high PBD-binding affinity.

The invention also provides the compounds as pharmaceutically acceptable salts, solvates, hydrates, or stereoisomers. In another aspect, the invention provides the compounds in pharmaceutically acceptable carriers and the use of the compounds for the preparation of a medicament. The invention further provides kits containing the compounds of the invention, and kits for synthesizing the compounds of the invention.

In one aspect, the invention provides a compound of Formula (I):

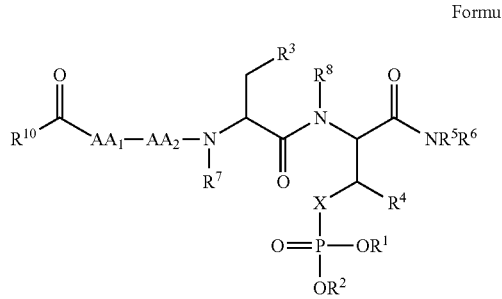

Formula (I)

or a pharmaceutically acceptable salt, solvate, hydrate, or stereoisomer thereof;
wherein
$R^{10}$ is

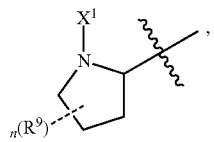

$(C_{1-6})$alkyl, amino, $(C_{2-6})$alkenyl, cycloalkyl, heterocyclic, aryl-$(C_{0-6})$alkyl, or heretoaryl-$(C_{0-6})$alkyl, wherein each of said alkyl, cycloalkyl, heterocyclic, aryl and heteroaryl moieties is optionally substituted by one or more same or different substituents selected from the group of aryl, heteroaryl, hydroxyl, hydrosulfide, alkyl, alkoxy, alkenyl, halogen, nitro, cyano, ester, amine, amide, carboxyl, and alkyl-carbonyl groups;

n 0, 1, 2, or 3;

X is O, —$(C_{1-6})$alkyl-, or —$C(Y)_2$—; wherein Y, for each occurrence independently, is F, Cl, or Br;

$X^1$ is H, $(C_{1-6})$alkyl-C(O)—, or a polyethylene glycol moiety or a derivative thereof;

$R^1$ and $R^2$, each independently, are selected from the group of H, $(C_{1-6})$alkyl-C(O)O—$(C_{1-6})$alkyl-, $(C_{1-20})$alkyl, allyl-$(C_{1-20})$alkyl, aryl-$(C_{1-20})$alkyl-, heteroaryl-$(C_{1-20})$alkyl, $X^2$O—C(O)—$(C_{1-6})$alkyl-, and amino$(C_{1-6})$alkyl, wherein each alkyl moiety that appears at the $R^1$ and $R^2$ positions is further optionally substituted by one or more carboxyl, hydroxyl, or alkoxy groups;

$X^2$ is H or $(C_{1-6})$alkyl; wherein the $(C_{1-6})$alkyl is optionally substituted by one or more hydroxyl, halo, or alkoxy groups;

$R^3$ is H, —OH, $(C_{1-6})$alkyl, $(C_{1-6})$alkyl-C(O)O—, or $(C_{1-6})$alkoxy;

$R^4$ is H, acyl, $(C_{1-6})$alkyl, $(C_{1-6})$alkyl-OC(O)O—, or $(C_{1-6})$alkyl-O—C(S)—O—;

$R^5$ and $R^6$, each independently, are selected from the group of H, $(C_{1-6})$alkyl, $(C_{1-6})$alkyl-C(O)—, $(C_{1-6})$alkoxy-$(C_{1-6})$alkyl, $X^3$=N—O—$(C_{1-6})$alkyl, and a glycine moiety; wherein $X^3$ is derived from a sugar moiety;

$R^7$ and $R^8$, each independently, are selected from the group of H, $(C_{1-20})$alkyl, and $(C_{1-20})$alkyl-C(O)—;

$R^9$ each independently, is R', R'—CH=N—O—, R'—$(C_{1-6})$alkyl-O—, R'—C(O)—NH—O—, R'—$(C_{1-6})$alkyl-S—, or R'—$(C_{1-6})$alkyl;

R' is H, $(C_{1-6})$alkyl, halo, amino-O—, $(C_{1-6})$alkyl-C(O)—, $(C_{2-6})$alkenyl, cycloalkyl, heterocyclic, aryl-$(C_{0-6})$alkyl, or heretoaryl-$(C_{0-6})$alkyl, wherein each of said alkyl, cycloalkyl, heterocyclic, aryl and heteroaryl moieties is optionally substituted by one or more same or different substituents selected from the group of aryl, heteroaryl, hydroxyl, hydrosulfide, alkyl, alkoxy, alkenyl, halogen, nitro, cyano, ester, amine, amide, carboxyl, and alkyl-carbonyl groups;

$AA_1$ is an amino acid moiety selected from the group of Cys, Asp, Glu, Phe, Gly, His, Ile, Lys, Leu, Met, Asn, Pro, Gln, Arg, Ser, Thr, Val, Trp, and Tyr; and $AA_2$ is absent or an amino acid moiety selected from the group of His, Gln, Ala, Cys, Glu, Phe, Ile, Met, Asn, Ser, Thr, Val, and Tyr;

wherein each of the amino acid moieties for $AA_1$ or $AA_2$ is optionally substituted by halo, $(C_{1-20})$alkyl, allyl-$(C_{1-20})$alkyl, $(C_{0-20})$alkoxy-C(O)—$(C_{1-20})$alkyl, amino$(C_{1-20})$alkyl, aryl-$(C_{1-20})$alkyl, heteroaryl-$(C_{1-20})$alkyl, aryl-$(C_{1-20})$alkyl-CH=N—O—, aryl-$(C_{1-20})$alkoxy, aryl-$(C_{1-20})$alkyl-S—, aryl-$(C_{1-20})$alkyl-C(O)—NH—O—, heteroaryl-$(C_{1-20})$alkyl-C(O)—NH—O—, and wherein each of the said alkyl, aryl and heteroaryl moieties is further optionally substituted by one or more same or different subtituents selected from the group of aryl, heteroaryl, alkenyl, alkoxy, alkyl, halo, hydroxyl, amine, amide, carboxyl, ester groups.

In certain embodiments of Formula (I):
a) $R^1$, $R^2$ and $R^3$ cannot be all H at the same time;
b) when n is 0 and $R^3$ is H, $AA_2$ is a substituted amino acid moiety; and
c) when $R^3$ is —OH, at least one of $R^1$ and $R^2$ must be $(C_{1-6})$alkyl-C(O)O—$(C_{1-6})$alkyl.

In another aspect, the invention provides a compound of Formula (II):

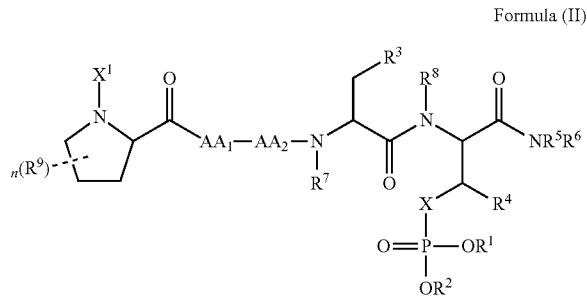

Formula (II)

wherein
n is 0, 1, 2, or 3;
X is O, —$(C_{1-6})$alkyl-, or —$C(Y)_2$—; wherein Y, for each occurrence independently, is F, Cl, or Br;

$X^1$ is H, $(C_{1-6})$alkyl-C(O)—, or a polyethylene glycol moiety or a derivative thereof;

$R^1$ and $R^2$, each independently, are selected from the group of H, $(C_{1-6})$alkyl-C(O)O—$(C_{1-6})$alkyl-, $(C_{1-20})$alkyl, allyl-$(C_{1-20})$alkyl, aryl-$(C_{1-20})$alkyl-, heteroaryl-$(C_{1-20})$alkyl, $X^2$O—C(O)—$(C_{1-6})$alkyl-, and amino$(C_{1-6})$alkyl, wherein each alkyl moiety that appears at the $R^1$ and $R^2$ positions is further optionally substituted by one or more carboxyl, hydroxyl, or alkoxy groups;

$X^2$ is H or $(C_{1-6})$alkyl; wherein the $(C_{1-6})$alkyl is optionally substituted by one or more hydroxyl, halo, or alkoxy groups;

$R^3$ is H, —OH, $(C_{1-6})$alkyl, $(C_{1-6})$alkyl-C(O)O—, or $(C_{1-6})$alkoxy;

$R^4$ is H, acyl, $(C_{1-6})$alkyl, $(C_{1-6})$alkyl-OC(O)O—, or $(C_{1-6})$alkyl-O—C(S)—O—;

$R^5$ and $R^6$, each independently, are selected from the group of H, $(C_{1-6})$alkyl, $(C_{1-6})$alkyl-C(O)—, $(C_{1-6})$alkoxy-$(C_{1-6})$alkyl, $X^3$=N—O—$(C_{1-6})$alkyl, and a glycine moiety; wherein $X^3$ is derived from a sugar moiety;

$R^7$ and $R^8$, each independently, are selected from the group of H, $(C_{1-20})$alkyl, and $(C_{1-20})$alkyl-C(O)—;

$R^9$ each independently, is R', R'—CH=N—O—, R'—$(C_{1-6})$alkyl-O—, R'—C(O)—NH—O—, R'—$(C_{1-6})$alkyl-S—, or R'—$(C_{1-6})$alkyl;

R' is H, $(C_{1-6})$alkyl, halo, amino-O—, $(C_{1-6})$alkyl-C(O)—, $(C_{2-6})$alkenyl, cycloalkyl, heterocyclic, aryl-$(C_{0-6})$alkyl, or heretoaryl-$(C_{0-6})$alkyl, wherein each of said alkyl, cycloalkyl, heterocyclic, aryl and heteroaryl moieties is optionally substituted by one or more same or different substituents selected from the group of aryl, heteroaryl, hydroxyl, hydrosulfide, alkyl, alkoxy, alkenyl, halogen, nitro, cyano, ester, amine, amide, carboxyl, and alkyl-carbonyl groups;

$AA_1$ is an amino acid moiety selected from the group of Cys, Asp, Glu, Phe, Gly, His, Ile, Lys, Leu, Met, Asn, Pro, Gln, Arg, Ser, Thr, Val, Trp, and Tyr; and $AA_2$ is absent or an amino acid moiety selected from the group of His, Gln, Ala, Cys, Glu, Phe, Ile, Met, Asn, Ser, Thr, Val, and Tyr;

wherein each of the amino acid moieties for $AA_1$ or $AA_2$ is optionally substituted by halo, $(C_{1-20})$alkyl, allyl-$(C_{1-20})$alkyl, $(C_{0-20})$alkoxy-C(O)—$(C_{1-20})$alkyl, amino$(C_{1-20})$alkyl, aryl-$(C_{1-20})$alkyl, heteroaryl-$(C_{1-20})$alkyl, aryl-$(C_{1-20})$alkyl-CH=N—O—, aryl-$(C_{1-20})$alkoxy, aryl-$(C_{1-20})$alkyl-S—, aryl-$(C_{1-20})$alkyl-C(O)—NH—O—, heteroaryl-$(C_{1-20})$alkyl-C(O)—NH—O—, and wherein each of the said alkyl, aryl and heteroaryl moieties is further optionally substituted by one or more same or different substituents selected from the group of aryl, heteroaryl, alkenyl, alkoxy, alkyl, halo, hydroxyl, amine, amide, carboxyl, ester groups;

or a pharmaceutically acceptable salt, solvate, hydrate, or stereoisomer thereof.

In certain embodiments of Formula (II):

a) $R^1$, $R^2$ and $R^3$ cannot be all H at the same time;

b) when n is 0 and $R^3$ is H, $AA_2$ is a substituted amino acid moiety; and c) when $R^3$ is —OH, at least one of $R^1$ and $R^2$ must be $(C_{1-6})$alkyl-C(O)O—$(C_{1-6})$alkyl.

Certain embodiments of the invention provide a compound of Formula (I) according to Formula (A) or (A'):

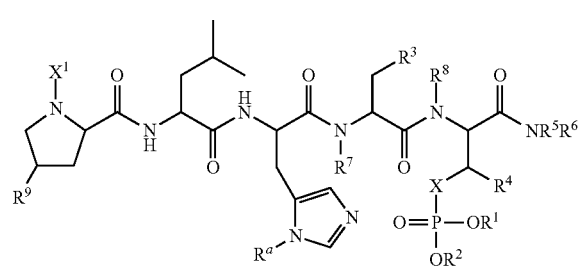

(A)

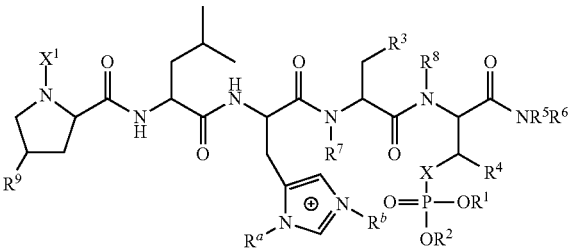

(A')

Wherein

X is O, $CH_2$, or $CF_2$;

$X^1$ is H, or $(C_{1-6})$alkyl-C(O)—;

$R^1$ and $R^2$, each independently, are selected from the group of H, $(C_{1-6})$alkyl-C(O)O—$(C_{1-6})$alkyl-, $(C_{1-20})$alkyl, allyl-$(C_{1-20})$alkyl, aryl-$(C_{1-20})$alkyl-, heteroaryl-$(C_{1-20})$alkyl, $X^2$O—C(O)—$(C_{1-6})$alkyl-, and amino$(C_{1-6})$alkyl, wherein each alkyl moiety that appears at the $R^1$ and $R^2$ positions is further optionally substituted by one or more carboxyl, hydroxyl, or alkoxy groups;

$R^3$ is H, —OH, $(C_{1-6})$alkyl, $(C_{1-6})$alkyl-C(O)O—, or $(C_{1-6})$alkoxy;

$R^4$ is H, acyl, or $(C_{1-6})$alkyl;

$R^5$ and $R^6$, each independently, are selected from the group of H, $(C_{1-6})$alkyl, $(C_{1-6})$alkyl-C(O)—, and $(C_{1-6})$alkoxy-$(C_{1-6})$alkyl;

$R^a$ is H, aryl-$(C_{1-20})$alkyl, heteroaryl-$(C_{1-20})$alkyl, $(C_{1-20})$alkyl, allyl-$(C_{1-20})$alkyl, $(C_{0-20})$alkoxy-C(O)—$(C_{1-20})$alkyl, or amino$(C_{1-20})$alkyl; wherein each of the said alkyl, aryl, and heteroaryl moieties is further optionally substituted by one or more same or different substituents selected from the group of $(C_{1-6})$alkyl, carboxyl, halo, hydroxyl, amine, and $(C_{1-6})$alkoxy groups;

$R^b$ is selected from the group of allyl-$(C_{1-6})$alkyl, aryl-$(C_{1-6})$alkyl-, heteroaryl-$(C_{1-6})$alkyl, and $(C_{1-6})$alkyl optionally substituted by one or more carboxyl, $(C_{1-6})$alkoxyl, or hydroxyl groups;

$R^7$ and $R^8$, each independently, are selected from the group of H, $(C_{1-6})$alkyl, and $(C_{1-6})$alkyl-C(O)—; and $R^9$ is H, halo, $(C_{2-6})$alkenyl-$(C_{1-6})$alkyl-O—, aryl-$(C_{1-6})$alkyl-CH=N—O—, heteroaryl-$(C_{1-6})$alkyl-CH=N—O—, or $(C_{1-6})$alkyl; wherein each of said alkyl, aryl and heteroaryl moieties is optionally substituted by one or more same or different substituents selected from the group of aryl, heteroaryl, hydroxyl, alkyl, alkoxy, alkenyl, halogen, nitro, cyano, ester, amine, amide, carboxyl, and alkyl-carbonyl groups;

or a pharmaceutically acceptable salt, solvate, hydrate, or stereoisomer thereof.

In other embodiments, the invention provides a compound of Formula (I) according to Formula (B) or (B'):

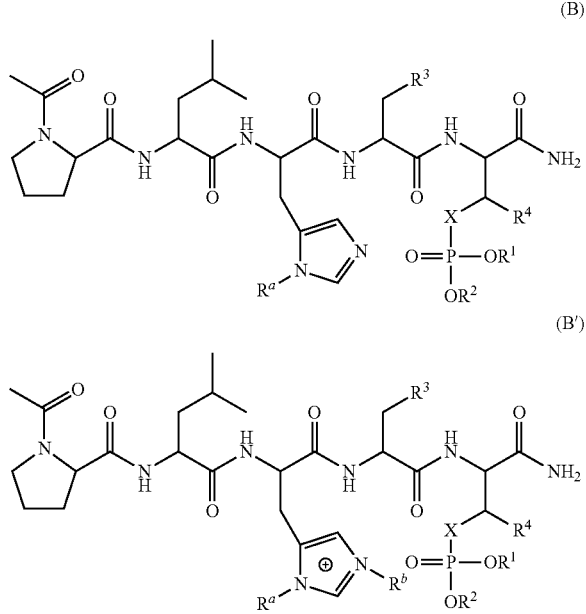

Wherein

X is O or CH$_2$;

one of R$^1$ and R$^2$ is (C$_{1-6}$)alkyl-C(O)O—(C$_{1-6}$)alkyl- or H, and the other is selected from the group of H, (C$_{1-6}$)alkyl, allyl-(C$_{1-6}$)alkyl-, aryl-(C$_{1-6}$)alkyl-, (C$_{1-6}$)alkyl-C(O)O—(C$_{1-6}$)alkyl-, and heteroaryl-(C$_{1-6}$)alkyl-; wherein each alkyl moiety is further optionally substituted by one or more carboxyl, hydroxyl, or (C$_{1-6}$)alkoxy groups;

R$^3$ is H, —OH, (C$_{1-6}$)alkyl, (C$_{1-6}$)alkyl-C(O)O—, or (C$_{1-6}$)alkoxy;

R$^4$ is H or (C$_{1-6}$)alkyl; and

R$^a$ is H, (C$_{1-10}$)alkyl, aryl-(C$_{1-10}$)alkyl, or heteoaryl-(C$_{1-10}$)alkyl; wherein each of the said alkyl, aryl, and heteroaryl moieties is further optionally substituted by one or more same or different substituents selected from the group of carboxyl, hydroxyl, and (C$_{1-6}$)alkoxy;

R$^b$ is selected from the group of allyl-(C$_{1-6}$)alkyl, aryl-(C$_{1-6}$)alkyl-, heteroaryl-(C$_{1-6}$)alkyl, and (C$_{1-6}$)alkyl optionally substituted by one or more carboxyl, (C$_{1-6}$)alkoxyl, or hydroxyl groups;

or a pharmaceutically acceptable salt, solvate, hydrate, or stereoisomer thereof.

Exemplified compounds of the above formulae include, but are not limited to, the compounds provided infra.

The invention provides compositions including any of the compounds of the above formulae (hereinafter "the compounds of the invention") in a pharmaceutically acceptable carrier, for use, for example, for the preparation of a medicament. The medicament can be, for example, a medicament for the prevention, amelioration, or treatment of a hyperproliferative disorder such as cancer.

The compounds of the invention can be used in methods for the prevention, amelioration, or treatment of a subject for a hyperproliferative disorder. Such methods can further include identification of a subject suffering from or suspected of suffering from a hyperproliferative disorder and/or monitoring the subject for prevention, amelioration, or treatment of a hyperproliferative disorder.

In certain embodiments, the hyperproliferative disorder is cancer. Cancers can be characterized as solid tumors and non-solid tumors. Cancers include, but are not limited to Acute Lymphoblastic Leukemia, Acute Myeloid Leukemia, Adrenocortical Carcinoma, Basal Cell Carcinoma, Bladder Cancer, Bone Cancer, Brain Tumor, Breast Cancer, Cervical Cancer, Chronic Lymphocytic Leukemia, Chronic Myelogenous Leukemia, Chronic Myeloproliferative Disorders, Colon Cancer, Colorectal Cancer, Cutaneous T-Cell Lymphoma, Esophageal Cancer, Ewing Family of Tumors, Retinoblastoma, Gastric (Stomach) Cancer, Gastrointestinal Tumors, Glioma, Head and Neck Cancer, Hepatocellular (Liver) Cancer, Hodgkin Lymphoma, Islet Cell Tumors (Endocrine Pancreas), Kidney (Renal Cell) Cancer, Laryngeal Cancer, Non-small Cell Lung Cancer, Small Cell Lung Cancer, Lymphoma, Medulloblastoma, Melanoma, Pancreatic Cancer, Prostate Cancer, Renal Cancer, Rectal cancer, Thyroid Cancer.

The compounds of the invention can also be used in methods for the prevention, amelioration, or treatment of a subject for acquired immunodeficiency syndrome (AIDS). In certain embodiments, the compounds of the invention can be tagged with a HIV Tat-sequence for inhibition of HIV budding.

The invention provides kits containing at least one compound of the inventions and instructions for use.

The invention provides libraries including at least two compounds of the invention.

In another aspect, the invention provides a pivaloyloxymethyl ("POM") protected amino acid analogue, or a salt, solvate, hydrate, or stereoisomer thereof. In certain embodiments, the POM-protected amino acid analogue of the invention is a mono- or di-POM protected pThr, pSer, or Pmab, which may be further protected by one or more additional protecting groups that are same or different from POM.

Thus, a further aspect of the invention provides a method for preparing peptide derivatives. The method comprises using a POM-protected amino acid analogue of the invention as an intermediate or a building block. Exemplified POM-protected amino acid analogues of the invention include, but are not limited to, those provided infra.

The invention also provides a compound (including a peptide derivative) prepared according to any preparation method of the invention.

The invention also includes methods of designing, synthesizing, and/or using the compounds or the POM-protected amino acid analogues of the invention. In certain embodiments, the invention provides compounds made according to any synthetic method disclosed herein.

Other aspects of the invention are discussed infra.

DETAILED DESCRIPTION

Definitions

Figure 1:
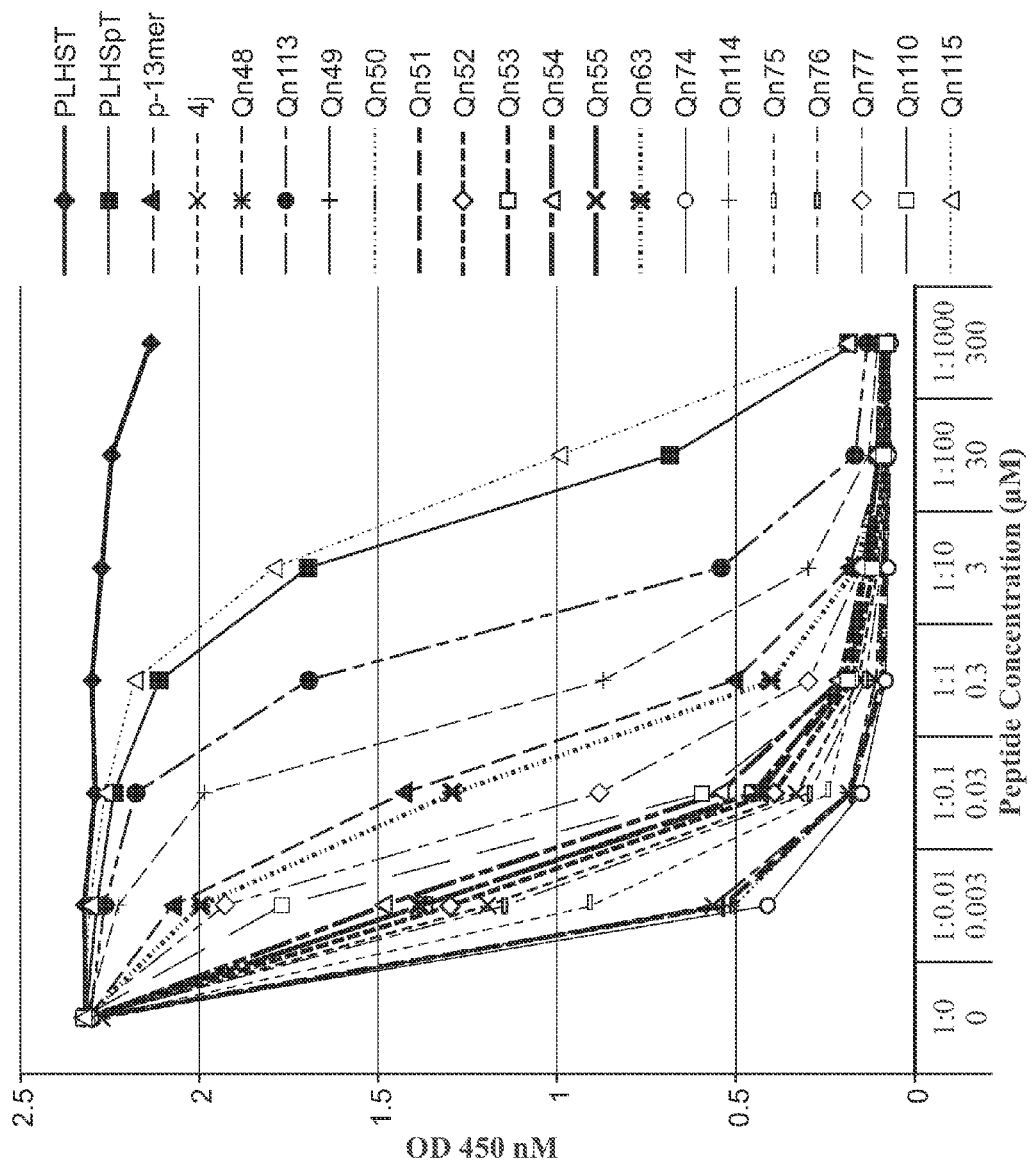
FIG. 1 is a chart showing data from ELISA binding assays for compounds provided in Table 2 infra.

An "agent" is understood herein to include a therapeutically active compound or a potentially therapeutically active compound. An agent can be a previously known or unknown compound. As used herein, an agent is typically a non-cell based compound, however, an agent can include a biological therapeutic agent, e.g., peptide or nucleic acid therapeutic, cytokine, antibody, etc.

An "agonist" is understood herein as a chemical substance capable of initiating the same reaction or activity typically produced by the binding of an endogenous substance or ligand to its target. An "antagonist" is understood herein as a chemical substance capable of inhibiting the reaction or activity typically produced by the binding of an endogenous substance (e.g., an endogenous agonist) to its target to prevent signaling through a receptor, to prevent downstream signaling, or to prevent cellular events (e.g., progression through cell cycle) that are the normal result of activation of the target. The antagonist can bind directly to the target or can act through other proteins or factors required for signaling. Agonists and antagonists can modulate some or all of the activities of the endogenous substance or ligand that binds to the target. Antagonists are typically characterized by determining the amount of the antagonist is required to inhibit the activity of the endogenous agonist. For example, an inhibitor at 0.01-, 0.1-, 1-, 5-, 10-, 50-, 100-, 200-, 500-, or 1000-fold molar concentration relative to the agonist can inhibit the activity of the agonist by at least 10%, 50%, 90%, or more.

As used herein "amelioration" or "treatment" is understood as meaning to lessen or decrease at least one sign, symptom, indication, or effect of a specific disease or condition. For example, amelioration or treatment of cancer can be determined using the standard RECIST (Response Evaluation Criteria in Solid Tumors) criteria including the assessment of tumor burden, by survival time, reduced presence of tumor markers (e.g., prostate specific antigen), or any other clinically acceptable indicators of disease state or progression. Amelioration and treatment can require the administration of more than one dose of an agent or therapeutic. As used herein, "prevention" is understood as to limit, reduce the rate or degree of onset, or inhibit the development of at least one sign or symptom of a disease or condition. For example, a subject having a genetic predisposition to develop a disease may develop disease later in life, e.g., delay of BRCA1 or BRCA2 related breast cancer development from third or fourth decade of life to fifth or beyond. Prevention can require the administration of more than one dose of an agent or therapeutic.

As used herein, an "aminooxy-containing amino acid" can be a modified proline, or an amino acid modified to provide a universal scaffold for modification with an aldehyde. Exemplary structures are provided:

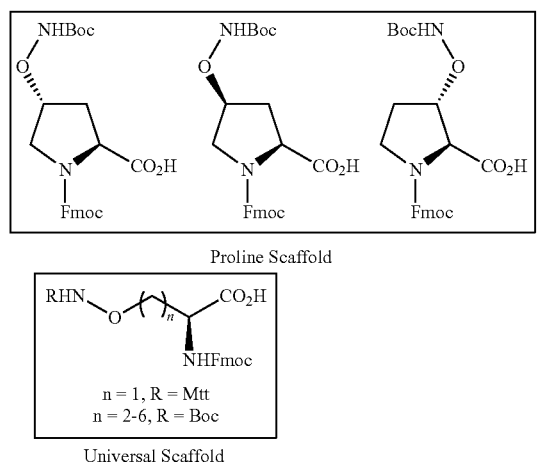

Proline Scaffold

Universal Scaffold n = 1, R = Mtt
n = 2-6, R = Boc

Chemical classes and groups are provided herein and referred to by chemical names, common names, and/or chemical structures. In the absence of an explicit definition herein, definitions of chemical structures can be found in chemical dictionaries, science textbooks, such as organic chemistry textbooks, or in databases. Chemical classes and groups commonly referred to herein are provided as follows.

The term "alkoxy," as used herein, refers to an alkyl or a cycloalkyl group which is linked to another moiety though an oxygen atom. Alkoxy groups can be optionally substituted with one or more substituents. As used herein, "C$_0$alkoxy" refers to a hydroxyl (—OH) group.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively. For example, the invention contemplates cyano and propargyl groups.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, the term "alkyl" refers to a group having two radical groups, such as "—CH$_2$—". The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., C$_1$-C$_{30}$ for straight chain, C$_3$-C$_{30}$ for branched chain), or 20 or fewer, even 10 or fewer. Likewise, preferred cycloalkyls have from 3-10 carbon atoms in their ring structure, and more preferably have 3, 4, 5, 6 or 7 carbons in the ring structure.

Moreover, the term alkyl as used throughout the specification and claims is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively.

As used herein, an amide is understood as a derivative of an oxoacids in which an acidic hydroxyl group has been replaced by an amino or substituted amino group. Compounds having one, two or three acyl groups on a given nitrogen are generically included and may be designated as primary, secondary and tertiary amides, respectively, e.g. PhC(=O)NH$_2$ benzamide, CH$_3$S(=O)$_2$NMe$_2$ N,N-dimethylmethanesulfonamide, [RC(=O)]$_2$NH secondary amides (see imides), [RC(=O)]$_3$N tertiary amides, PhP(=O)(OH)NH$_2$ phenylphosphonamidic acid. An amide group as used herein is understood as a group with —NH$_2$, NHR and NR$_2$. Amide groups should not be distinguished by means of the terms primary, secondary and tertiary.

As used herein, an "allyl" group is understood as a structure containing a carbon-carbon double bond. For example, it includes a structural formula H$_2$C=CH—CH$_2$R, where R is the connection to the rest of the molecule.

As used herein, "amine" or "amino" is understood as Compounds formally derived from ammonia by replacing one, two or three hydrogen atoms by hydrocarbon groups, and having the general structures RNH$_2$ (primary amines), R$_2$NH (secondary amines), R$_3$N (tertiary amines). An amino group is understood as having the structure NH$_2$, —NHR, or NR$_2$.

As used herein, "aryl group" is understood as refers to any functional group or substituent derived from a simple aromatic ring, may it be phenyl, thiophene, indolyl, etc (see IUPAC nomenclature, goldbook.iupac.org/A00464.html). Aryl groups derived from arenes by removal of a hydrogen atom from a ring carbon atom. Groups similarly derived from heteroarenes are sometimes subsumed in this definition. "Aryl" is used for the sake of abbreviation or generalization. For example, a simple aryl group is phenyl, C$_6$H$_5$; it is derived from benzene. The tolyl group, CH$_3$C$_6$H$_4$, is derived from toluene (methylbenzene). The xylyl group, (CH$_3$)$_2$C$_6$H$_3$, is derived from xylene (dimethylbenzene). The class of heterocyclyl groups derived from heteroarenes by removal of a hydrogen atom from any ring atom; an alternative term is hetaryl.

As used herein, "carboxylic acid" is understood as a group having the structure RC(=O)OH. A carboxylic acid group is understood to denote the —C(=O)OH group including its carbon atom.

As used herein, "carbonyl group" is understood as a group containing the carbonyl group, C=O. The term is commonly used in the restricted sense of aldehydes and ketones, however as used herein it includes carboxylic acids and derivatives.

As used herein, "carboxyl" or "carboxy" group is understood as a structure containing —COOH or —COOR. The term includes carboxylic acids and derivatives.

The term "enantiomers" refers to two stereoisomers of a compound which are non-superimposable mirror images of one another. An equimolar mixture of two enantiomers is called a "racemic mixture" or a "racemate."

As used herein, a "halogen" or "halo" is understood as an element located in Group VIIA of the periodic table. Halogens are reactive nonmetals having seven valence electrons. Halogen groups include —F, —Cl, —Br, and —I.

As used herein, modification of a class of chemical group with the term "hetero" is understood as the class of functional groups derived from the particular class of the functional group by removal of a hydrogen atom from any carbon atom.

"Heterocyclyl" groups as used herein are univalent groups formed by removing a hydrogen atom from any ring atom of a heterocyclic compound.

The term "heterocyclic" as used herein, refers to organic compounds that contain at least at least one atom other than carbon (e.g., S, O, N) within a ring structure. The ring structure in these organic compounds can be either aromatic or non-aromatic. Some examples of heterocyclic moieties include, are not limited to, pyridine, pyrimidine, pyrrolidine, furan, tetrahydrofuran, tetrahydrothiophene, and dioxane.

As used herein, "olefin group" is understood as an acyclic and or cyclic hydrocarbon having one or more carbon-carbon double bonds, apart from the formal ones in aromatic compounds. The class olefins subsumes alkenes and cycloalkenes and the corresponding polyenes.

In compounds, amino acid positions are determined relative to the phosphothreonine which is arbitrarily defined as position zero (0) Amino acids to the C-terminus of the peptide (to the right) are indicated as positions +1 (adjacent to the phosphothreonine), +2 (adjacent to the +1 position, but not the phosphothrenine), etc. Similarly, amino acids towards the N-terminus are defined as positions −1 (adjacent to the phosphothreonine), −2 (adjacent to the −1 position, but not the phosphothrenine), etc.

"Contacting a cell" is understood herein as providing an agent to a test cell e.g., a cell to be treated in culture or in an animal, such that the agent or isolated cell can interact with the test cell or cell to be treated, potentially be taken up by the test cell or cell to be treated, and have an effect on the test cell or cell to be treated. The agent or isolated cell can be delivered to the cell directly (e.g., by addition of the agent to culture medium or by injection into the cell or tissue of interest), or by delivery to the organism by an enteral or parenteral route of administration for delivery to the cell by circulation, lymphatic, or other means.

As used herein, "changed as compared to a control" sample or subject is understood as having a level of the analyte or diagnostic or therapeutic indicator to be detected at a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., PSA) or a substance produced by a reporter construct (e.g., β-galactosidase or luciferase). Depending on the method used for detection the amount and measurement of the change can vary. For example, a change in the amount of cleavage of analyte present will depend on the exact reaction conditions and the amount of time after exposure to the agent the sample is collected. Changed as compared to a control reference sample can also include decreased binding of a ligand to a receptor in the presence of an antagonist or other inhibitor. Determination of statistical significance is within the ability of those skilled in the art.

As used herein, "detecting", "detection" and the like are understood that an assay performed for identification of a specific analyte in a sample or a product from a reporter construct in a sample. Detection can also include identification of activation of a kinase or other enzyme. Detection can include the identification of a mutation in a gene sequence, such as a point mutation, a deletion of all or part of the coding sequence or transcriptional/translational regulatory sequences of the gene, a truncation of the gene sequence, or any other alteration that can alter the expression level or the sequence of the protein expressed by the gene, particularly when the alteration of the sequence results in a phenotypic change in the subject. Detection can include the determination of the size of a tumor, the presence or absence of metastases, the presence or absence of angiogenesis. The amount of analyte detected in the sample can be none or below the level of detection of the assay or method.

By "diagnosing" as used herein refers to a clinical or other assessment of the condition of a subject based on observation, testing, or circumstances for identifying a subject having a disease, disorder, or condition based on the presence of at least one sign or symptom of the disease, disorder, or condition. Typically, diagnosing using the method of the invention includes the observation of the subject for other signs or symptoms of the disease, disorder, or condition by physical examination, imaging, further laboratory tests, etc.

As used herein, a "diagnostic marker" is understood as one or more signs or symptoms of a disease or condition that can be assessed, preferably quantitatively to monitor the progress or efficacy of a disease treatment or prophylactic treatment or method. A diagnostic marker can be a substance that is released by a tumor (e.g., antigens such as PSA or enzymes). A diagnostic marker can be tumor size and/or grade of tumor and/or growth rate of tumor. A diagnostic marker can be the presence or absence of angiogenesis. A diagnostic marker can be a change in blood counts or cellular function measured in an in vitro assay, or the presence and characteristics of metastases (number and size).

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such a treatment may be ineffective in a subgroup that can be identified by the expression profile or profiles.) "Less effective" means that the treatment results in a therapeutically significant lower level of pharmacological effectiveness and/or a therapeutically greater level of adverse physiological effects, e.g., greater liver toxicity.

Thus, in connection with the administration of a drug, a drug which is "effective against" a disease or condition indicates that administration in a clinically appropriate manner results in a beneficial effect for at least a statistically significant fraction of patients, such as an improvement of symptoms, a cure, a reduction in disease signs or symptoms, extension of life, improvement in quality of life, or other effect generally recognized as positive by medical doctors familiar with treating the particular type of disease or condition.

As used herein, "Fmoc" is understood as 9-Fluorenylmethyloxycarbonyl having the molecular formula $C_{15}H_{11}ClO_2$. The structure of this protective group is well known.

As used herein, "heterologous" as in "heterologous protein" is understood as a protein not natively expressed in the cell in which it is expressed. The heterologous protein may be, but need not be, from a different species.

The term "hyperproliferative disorder" or "neoplasia" includes malignancies characterized by excess cell proliferation or growth, or reduced cell death. In specific embodiments, the term "cancer" includes but is not limited to carcinomas, sarcomas, leukemias, and lymphomas. The term "cancer" also includes primary malignant tumors, e.g., those whose cells have not migrated to sites in the subject's body other than the site of the original tumor, and secondary malignant tumors, e.g., those arising from metastasis, the migration of tumor cells to secondary sites that are different from the site of the original tumor. Tumors include solid tumors (i.e., non-blood tumors) and blood tumors. Cancers include, but are not limited to, Acute Lymphoblastic Leukemia, Acute Myeloid Leukemia, Adrenocortical Carcinoma, Basal Cell Carcinoma, Bladder Cancer, Bone Cancer, Brain Tumor, Breast Cancer, Cervical Cancer, Chronic Lymphocytic Leukemia, Chronic Myelogenous Leukemia, Chronic Myeloproliferative Disorders, Colon Cancer, Colorectal Cancer, Cutaneous T-Cell Lymphoma, Esophageal Cancer, Ewing Family of Tumors, Retinoblastoma, Gastric (Stomach) Cancer, Gastrointestinal Tumors, Glioma, Head and Neck Cancer, Hepatocellular (Liver) Cancer, Hodgkin Lymphoma, Islet Cell Tumors (Endocrine Pancreas), Kidney (Renal Cell) Cancer, Laryngeal Cancer, Lung Cancer, Non-Small Cell, Lung Cancer, Small Cell, Lymphoma, Medulloblastoma, Melanoma, Pancreatic Cancer, Prostate Cancer, Renal Cancer, Rectal cancer, Thyroid Cancer.

As used herein, "isolated" or "purified" when used in reference to a polypeptide means that a naturally polypeptide or protein has been removed from its normal physiological environment (e.g., protein isolated from plasma or tissue) or is synthesized in a non-natural environment (e.g., artificially synthesized in an in vitro translation system). Thus, an "isolated" or "purified" polypeptide can be in a cell-free solution or placed in a different cellular environment (e.g., expressed in a heterologous cell type). The term "purified" does not imply that the polypeptide is the only polypeptide present, but that it is essentially free (about 90-95%, up to 99-100% pure) of cellular or organismal material naturally associated with it, and thus is distinguished from naturally occurring polypeptide. Similarly, an isolated nucleic acid is removed from its normal physiological environment. "Isolated" when used in reference to a cell means the cell is in culture (i.e., not in an animal), either cell culture or organ culture, of a primary cell or cell line. Cells can be isolated from a normal animal, a transgenic animal, an animal having spontaneously occurring genetic changes, and/or an animal having a genetic and/or induced disease or condition.

The term "stereoisomers" as used herein refers to isomeric molecules are that have the same molecular formula and sequence of bonded atoms (constitution), but that differ only in the three-dimensional orientations of their atoms in space. The structural isomers share the same molecular formula, but the bond connections and/or their order between different atoms/groups differs. In certain embodiments of the invention, stereoisomers refer to the compounds having the same order and bond connections of the constituent atoms, but different orientation in space (such as, enantiomers, and diastereomers).

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The term "label" or "detectable label" as used herein refers to any atom or molecule which can be used to provide a detectable (preferably quantifiable) signal, and which can be attached to a chemical compound, a nucleic acid or protein. Labels may provide signals detectable by fluorescence, radioactivity, colorimetry, gravimetry, X-ray diffraction or absorption, magnetism, enzymatic activity, and the like. Various methods of labeling polypeptides and glycoproteins are known in the art and may be used. Examples of labels for polypeptides include, but are not limited to, the following: radioisotopes (e.g., $^3$H), fluorescent labels (e.g., FITC, rhodamine, lanthanide phosphors), enzymatic labels (e.g., horseradish peroxidase, beta-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. In others, the label is part of the fusion protein, e.g. Green Fluorescent Protein (GFP), Yellow Fluorescent Protein (YFP).

"Library" as used herein is understood to be a chemical library. Chemical libraries include two or more compounds (10 or more, 50 or more, 100 or more, 200 or more, 500 or more, 1000 or more, 5000 or more, 10,000 or more, etc.; or any range bracketed by the noted values), preferably that have structural and/or potential functional properties. Libraries can be used, for example for screening assays to select compounds with desired activities, e.g., kinase binding, kinase stimulating, kinase inhibiting activity.

"Obtaining" is understood herein as manufacturing, purchasing, or otherwise coming into possession of.

As used herein, "oligonucleotide sequence" is understood as a non-coding nucleic acid sequence prepared by chemical synthesis methods or by transcription from a construct including an appropriate promoter sequence. A double stranded RNA oligonucleotide sequence as used herein includes a single strand forming a hairpin structure (e.g., shRNA) or joined by other non-nucleic acid linkages, or two separate strands annealed to form a double stranded structure.

An "oxime modified peptide" and the like are understood as a peptide in which at least one amino acid includes an aminooxy group, —O—NH$_2$, that will be reacted with an aldehyde to make a oxime modified peptide. In an embodiment, the aminooxy containing peptide is reacted with a library of aldehyde compounds to provide a library of oxmine modified peptides. An exemplary reaction scheme is shown:

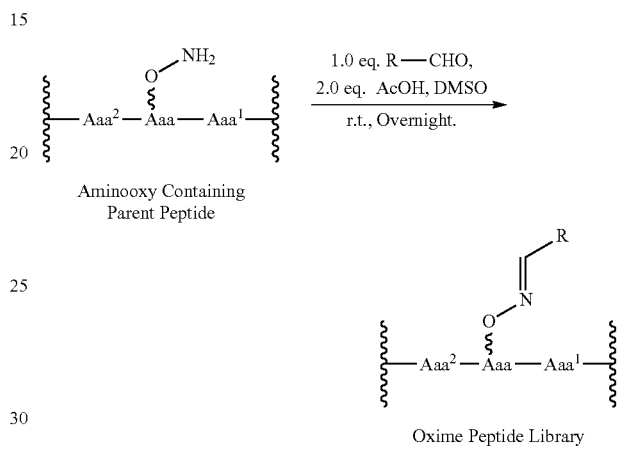

Oxime Peptide Library

A "peptide" or "peptide derivative" as used herein is understood as two or more independently selected natural or non-natural amino acids joined by a peptide bond. A peptide can include 2, 3, 4, 5, 6, 7, 8, 9, 10, 11, 12 or more natural or non-natural amino acids joined by peptide bonds.

A "peptide-peptoid hybrid" as used herein is understood as a peptide in which at least one amino acid comprises the non-natural amino acid N-alkylglycine having the below structure.

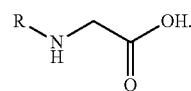

"Peptoids" are polymers of N-substituted glycine residues (NSG). These have emerged as an important class of peptide mimetic that can retain bioactivity while exhibiting resistance to proteolytic degradation. Peptide-peptoid hybrids containing both peptide and NSG residues have also shown significant utility. Examples are provided by the replacement of key Pro residues with NSG residues in WW and SH3 domain-binding peptides to achieve greater ligand selectivity and affinity (32).

As used herein, pharmaceutically acceptable salts include, without limitation, the tartrate, succinate, tartarate, bitartarate, dihydrochloride, salicylate, hemisuccinate, citrate, maleate, hydrochloride, carbamate, sulfate, nitrate, and benzoate salt forms thereof, as well as combinations thereof and the like. Any form of peptide mimentic is suitable for use in the methods of the present invention, e.g., a pharmaceutically acceptable salt of a peptide mimentic, a free base of a peptide mimentic, or a mixture thereof.

As used herein, "plurality" is understood to mean more than one. For example, a plurality refers to at least two, three, four, five, or more.

A "polo-like kinase" or "Plk" as used herein collectively refers to the proteins called Plk-1, (human sequence available as under Accession No. P53350.1 GI:1709658; mouse sequence available under Accession No. Q07832.2 GI:1709659; rat sequence available under Accession No. Q62673.1 GI:12230396; Pan troglodytes sequence available under Accession No. XP_001163585.1 GI:114661620); Plk-2 (human sequence available under Accession No. Q9NYY3.3 GI:22096374); Plk-3 (human sequence available under Accession No. Q9H4B4.2 GI:51338822); and Plk-4 (human sequence available under Accession No. O00444.3 GI:160113150), from any organism, preferably a mammalian organism, preferably from a human organism. Such proteins can be encoded by any nucleic acid that provides the appropriate translation product; however, in certain embodiments, the polo-like kinases are encoded by the native genes which can easily be identified using GenBank or any of a number of publicly available databases. All GenBank Nos. incorporated herein by reference as of the filing date of the instant application.

"Reporter construct" as used herein is understood to be an exogenously inserted gene, often present on a plasmid, with a detectable gene product, under the control of a promoter sequence. The activity of the promoter is modulated upon signaling through one or more known cellular pathways. Preferably, the gene product is easily detectable using a quantitative method. Common reporter genes include luciferase and beta-galactosidase. The reporter construct can be transiently inserted into the cell by transfection or infection methods. Alternatively, stable cell lines can be made using methods well known to those skilled in the art, or cells can be obtained from transgenic animals expressing a reporter construct. The specific reporter gene or method of detection is not a limitation of the invention.

A "sample" as used herein refers to a biological material that isolated from its environment (e.g., blood or tissue from an animal, cells, or conditioned media from tissue culture) and is suspected of containing, or known to contain an analyte, such as a tumor cell or a product from a reporter construct. A sample can also be a partially purified fraction of a tissue or bodily fluid. A reference sample can be a "normal" sample, from a donor not having the disease or condition fluid, or from a normal tissue in a subject having the disease or condition (e.g., normal tissue vs. tumor tissue). A reference sample can also be from an untreated donor or cell culture not treated with an active agent (e.g., no treatment or administration of vehicle only) and/or stimulus. A reference sample can also be taken at a "zero time point" prior to contacting the cell or subject with the agent or cell to be tested.

An agent, antibody, polypeptide, nucleic acid, or other compound "specifically binds" a target molecule, e.g., antigen, polypeptide, nucleic acid, or other compound, when the target molecule is bound with at least 100-fold, preferably at least 500-fold, preferably at least 1000-fold, preferably at least a 5000-fold, preferably at least a 10,000-fold preference as compared to a non-specific compounds, or a pool of non-specific compounds. Specifically binds can be used in relation to binding one of two or more related compounds that have physically related structures, e.g., two kinases, particularly 2 polo-like kinases. For example, an agent, antibody, polypeptide, nucleic acid, or other compound can "specifically bind" one polo-like kinase (e.g., Plk1) with at least a 10-fold, 50-fold, 100-fold, 500-fold, 1000-fold, 5000-fold, 10,000-fold or more preference over another polo-like kinase, e.g., Plk2, Plk3, or Plk4. Binding preferences and affinities, absolute or relative, can be determined, for example by determining the affinity for each pair separately or by the use of competition assays or other methods well known to those of skill in the art.

A "subject" as used herein refers to living organisms. In certain embodiments, the living organism is an animal. In certain preferred embodiments, the subject is a mammal. In certain embodiments, the subject is a domesticated mammal. Examples of subjects include humans, monkeys, dogs, cats, mice, rats, cows, horses, goats, and sheep. A human subject may also be referred to as a patient.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions such as cancer is within the ability of those in the art. Subjects suffering from, and suspected of suffering from, a specific disease, condition, or syndrome are not necessarily two distinct groups.

"Therapeutically effective amount," as used herein refers to an amount of an agent which is effective, upon single or multiple dose administration to the cell or subject, in prolonging the survivability of the patient with such a disorder beyond that expected in the absence of such treatment.

An agent can be administered to a subject, either alone or in combination with one or more therapeutic agents, as a pharmaceutical composition in mixture with conventional excipient, e.g., pharmaceutically acceptable carrier, or therapeutic treatments such as radiation.

It will be appreciated that the actual preferred amounts of active compounds used in a given therapy will vary according to e.g., the specific compound being utilized, the particular composition formulated, the mode of administration and characteristics of the subject, e.g., the species, sex, weight, general health and age of the subject. Optimal administration rates for a given protocol of administration can be readily ascertained by those skilled in the art using conventional dosage determination tests conducted with regard to the foregoing guidelines.

As used herein, "susceptible to" or "prone to" or "predisposed to" a specific disease or condition and the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

The term "transfection" as used herein refers to the introduction of a transgene into a cell. The term "transgene" as used herein refers to any nucleic acid sequence which is introduced into the genome of a cell by experimental manipulations. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e., particle bombardment) and the like.

The term "stable transfection" or "stably transfected" refers to the introduction and integration of a transgene into the genome of the transfected cell. The term "stable transfectant" refers to a cell which has stably integrated one or more transgenes into the genomic DNA.

The term "transient transfection" or "transiently transfected" refers to the introduction of one or more transgenes into a transfected cell in the absence of integration of the transgene into the host cell's genome. The term "transient transfectant" refers to a cell which has transiently integrated one or more transgenes.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

The term "disubstituted histidine" refers to a histidine residue substituted on the imidazole ring with at least two moieties such as aryl-$(C_{1-20})$alkyl (including aryl-$(C_{1-6})$alkyl-), heteroaryl-$(C_{1-20})$alkyl (including heteroaryl-$(C_{1-6})$alkyl), $(C_{1-20})$alkyl (including $(C_{1-6})$alkyl), allyl-$(C_{1-20})$alkyl (including allyl-$(C_{1-6})$alkyl), $(C_{0-20})$alkoxy-C(O)—$(C_{1-20})$alkyl, or amino$(C_{1-20})$alkyl; wherein each of the said alkyl, aryl, and heteroaryl moieties is further optionally substituted by one or more same or different substituents selected from the group of $(C_{1-6})$alkyl, carboxyl, halo, hydroxyl, amine, and $(C_{1-6})$alkoxy groups. In certain embodiments, the at least two moieties on the imidazole ring are $(C_{1-10})$alkyl, aryl-$(C_{1-10})$alkyl (including aryl-$(C_{1-6})$alkyl-), or heteroaryl-$(C_{1-10})$alkyl, allyl-$(C_{1-6})$alkyl, or $(C_{1-6})$alkyl optionally substituted by one or more carboxyl, $(C_{1-6})$alkoxyl, or hydroxyl groups. In certain embodiments, the two moieties are attached to the two nitrogen atoms of the imidazole ring.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

All oligonucleotide sequences are written from the 5'-end to the 3'-end unless otherwise specifically noted.

DETAILED DESCRIPTION OF THE INVENTION

The polo-like kinase 1 (Plk1) represents a new target for anticancer therapeutic development. Plk1 contains a C-terminal polo-box domain (PBD) that recognizes phospho-Ser (pSer)/phospho-Thr (pThr)-containing motifs, which provides sub-cellular localization that is critical for proper Plk1 function. Spatial disruption of Plk1 distribution by blocking PBD-dependent protein-protein interactions may afford an attractive alternative to kinase-directed inhibitors for the down-regulation of Plk1 function and Plk1 PBD-binding antagonists and may serve as a new class of anticancer agents.

In spite of recent discovery of peptide-based Plk PBD-binding antagonists that demonstrate good PBD-binding affinities, it has been observed some of these peptides exhibit relatively poor bioavailability in whole cell studies. The present inventors suspected that the reasons causing the poor bioavailability of these peptides are due to the di-anionic charge of phosphoryl functionalities in their structures.

To overcome the "charge problem" associated with peptide-based Plk PBD-binding antagonists, the parent dianionic phosphoryl species have previously been converted to singly charged mono-esters (see, e.g., PCT Patent Publication No. WO2012142245 A2). Generally, although not always, these mono-esters exhibit reduced potency and levels of mitotic block than the di-anionic species.

In one aspect, the present invention provides a phosphoryl derivatization protocol for the design and synthesis of peptide therapeutics wherein the net overall anionic charge is neutralized.

One aspect of the invention provides a novel class of compounds (or peptide derivatives) that are useful as anticancer therapeutics. In certain embodiments, the compounds of the invention include uncharged peptides or peptide derivatives that contain high affinity mono-ester bio-cleavable protecting groups. Such bio-cleavable protecting groups include, for example, a pivaloyloxymethyl (POM) group. In certain embbodiments, these peptides archieve neutralization of net anionic charge through inclusion of cationic bis-alkyl His residues. While retaining good efficacy, several peptide derivatives of the invention have also achieved enhanced bioavailability in cellular studies.

Without wishing to be bound by any theory, it is believed that the compounds of the invention act through a novel anticancer mode: the compounds down-regulate oncogenic Plk1 through spatial dis-regulation by blocking the function of its PBD.

The compounds, compositions and methods provided herein represent new approaches to the design and synthesis of peptides or peptide derivatives. The invention can lead to the development of additional therapeutically relevant PBD-directed agents.

The invention can also lead to peptide derivatives that are useful in unrelated therapeutic areas.

Compounds

The invention provides high affinity compounds bearing non-natural amino acids as well as peptide-peptoid hybrids (containing N-alkylglycine residues). The compounds of the invention contain a protected phosphoryl amino acid residue. In certain embbodiments, the compound of the invention is a peptide/peptide derivative containing a pThr, pSer, or Pmab residue.

In certain embodiments, the compounds of the invention have achieved good bioavailability as well as good efficacy.

In one aspect, the invention provides a compound of Formula (I):

Formula (I)

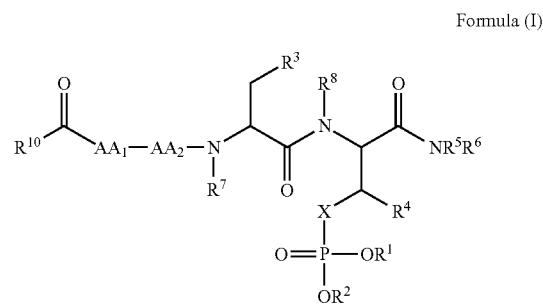

or a pharmaceutically acceptable salt, solvate, hydrate, or stereoisomer thereof;

wherein

R$^{10}$ is

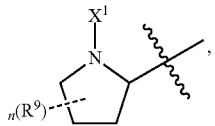

($C_{1-6}$)alkyl, amino, ($C_{2-6}$)alkenyl, cycloalkyl, heterocyclic, aryl-($C_{0-6}$)alkyl, or heretoaryl-($C_{0-6}$)alkyl, wherein each of said alkyl, cycloalkyl, heterocyclic, aryl and heteroaryl moieties is optionally substituted by one or more same or different substituents selected from the group of aryl, heteroaryl, hydroxyl, hydrosulfide, alkyl, alkoxy, alkenyl, halogen, nitro, cyano, ester, amine, amide, carboxyl, and alkylcarbonyl groups;

n is 0, 1, 2, or 3;

X is O, —($C_{1-6}$)alkyl-, or —C(Y)$_2$—; wherein Y, for each occurrence independently, is F, Cl, or Br;

X$^1$ is H, ($C_{1-6}$)alkyl-C(O)—, or a polyethylene glycol moiety or a derivative thereof;

R$^1$ and R$^2$, each independently, are selected from the group of H, ($C_{1-6}$)alkyl-C(O)O—($C_{1-6}$)alkyl-, ($C_{1-20}$)alkyl, allyl-($C_{1-20}$)alkyl, aryl-($C_{1-20}$)alkyl-, heteroaryl-($C_{1-20}$)alkyl, X$^2$O—C(O)—($C_{1-6}$)alkyl-, and amino($C_{1-6}$)alkyl, wherein each alkyl moiety that appears at the R$^1$ and R$^2$ positions is further optionally substituted by one or more carboxyl, hydroxyl, or alkoxy groups;

X$^2$ is H or ($C_{1-6}$)alkyl; wherein the ($C_{1-6}$)alkyl is optionally substituted by one or more hydroxyl, halo, or alkoxy groups;

R$^3$ is H, —OH, ($C_{1-6}$)alkyl, ($C_{1-6}$)alkyl-C(O)O—, or ($C_{1-6}$)alkoxy;

R$^4$ is H, acyl, ($C_{1-6}$)alkyl, ($C_{1-6}$)alkyl-OC(O)O—, or ($C_{1-6}$)alkyl-O—C(S)—O—;

R$^5$ and R$^6$, each independently, are selected from the group of H, ($C_{1-6}$)alkyl, ($C_{1-6}$)alkyl-C(O)—, ($C_{1-6}$)alkoxy-($C_{1-6}$)alkyl, X$^3$=N—O—($C_{1-6}$)alkyl, and a glycine moiety; wherein X$^3$ is derived from a sugar moiety;

R$^7$ and R$^8$, each independently, are selected from the group of H, ($C_{1-20}$)alkyl, and ($C_{1-20}$)alkyl-C(O)—;

R$^9$ each independently, is R', R'—($C_{1-6}$)alkyl-O—, R'—C(O)—NH—O—, R'—($C_{1-6}$)alkyl-S—, or R'—($C_{1-6}$)alkyl;

R' is H, ($C_{1-6}$)alkyl, halo, amino-O—, ($C_{1-6}$)alkyl-C(O)—, ($C_{2-6}$)alkenyl, cycloalkyl, heterocyclic, aryl-($C_{0-6}$)alkyl, or heretoaryl-($C_{0-6}$)alkyl, wherein each of said alkyl, cycloalkyl, heterocyclic, aryl and heteroaryl moieties is optionally substituted by one or more same or different substituents selected from the group of aryl, heteroaryl, hydroxyl, hydrosulfide, alkyl, alkoxy, alkenyl, halogen, nitro, cyano, ester, amine, amide, carboxyl, and alkyl-carbonyl groups;

AA$_1$ is an amino acid moiety selected from the group of Cys, Asp, Glu, Phe, Gly, His, Ile, Lys, Leu, Met, Asn, Pro, Gln, Arg, Ser, Thr, Val, Trp, and Tyr; and AA$_2$ is absent or an amino acid moiety selected from the group of His, Gln, Ala, Cys, Glu, Phe, Ile, Met, Asn, Ser, Thr, Val, and Tyr;

wherein each of the amino acid moieties for AA$_1$ or AA$_2$ is optionally substituted by halo, ($C_{1-20}$)alkyl, allyl-($C_{1-20}$)alkyl, ($C_{0-20}$)alkoxy-C(O)—($C_{1-20}$)alkyl, amino($C_{1-20}$)alkyl, aryl-($C_{1-20}$)alkyl, heteroaryl-($C_{1-20}$)alkyl, aryl-($C_{1-20}$)alkyl-CH=N—O—, aryl-($C_{1-20}$)alkoxy, aryl-($C_{1-20}$)alkyl-S—, aryl-($C_{1-20}$)alkyl-C(O)—NH—O—, heteroaryl-($C_{1-20}$)alkyl-C(O)—NH—O—, and wherein each of the said alkyl, aryl and heteroaryl moieties is further optionally substituted by one or more same or different subtituents selected from the group of aryl, heteroaryl, alkenyl, alkoxy, alkyl, halo, hydroxyl, amine, amide, carboxyl, ester groups.

In certain embodiments of Formula (I):

a) R$^1$, R$^2$ and R$^3$ cannot be all H at the same time;

b) when n is 0 and R$^3$ is H, AA$_2$ is a substituted amino acid moiety; and c) when R$^3$ is —OH, at least one of R$^1$ and R$^2$ must be ($C_{1-6}$)alkyl-C(O)O—($C_{1-6}$)alkyl.

In another aspect, the invention provides a compound of Formula (II):

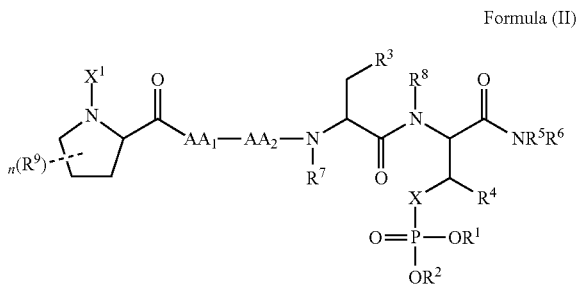

Formula (II)

wherein n is 0, 1, 2, or 3;

X is O, —($C_{1-6}$)alkyl-, or —C(Y)$_2$—; wherein Y, for each occurrence independently, is F, Cl, or Br;

X$^1$ is H, ($C_{1-6}$)alkyl-C(O)—, or a polyethylene glycol moiety or a derivative thereof;

R$^1$ and R$^2$, each independently, are selected from the group of H, ($C_{1-6}$)alkyl-C(O)O—($C_{1-6}$)alkyl-, ($C_{1-20}$)alkyl, allyl-($C_{1-20}$)alkyl, aryl-($C_{1-20}$)alkyl-, heteroaryl-($C_{1-20}$)alkyl, X$^2$O—C(O)—($C_{1-6}$)alkyl-, and amino($C_{1-6}$)alkyl, wherein each alkyl moiety that appears at the R$^1$ and R$^2$ positions is further optionally substituted by one or more carboxyl, hydroxyl, or alkoxy groups;

X$^2$ is H or ($C_{1-6}$)alkyl; wherein the ($C_{1-6}$)alkyl is optionally substituted by one or more hydroxyl, halo, or alkoxy groups;

R$^3$ is H, —OH, ($C_{1-6}$)alkyl, ($C_{1-6}$)alkyl-C(O)O—, or ($C_{1-6}$)alkoxy;

R$^4$ is H, acyl, ($C_{1-6}$)alkyl, ($C_{1-6}$)alkyl-OC(O)O—, or ($C_{1-6}$)alkyl-O—C(S)—O—;

R$^5$ and R$^6$, each independently, are selected from the group of H, ($C_{1-6}$)alkyl, ($C_{1-6}$)alkyl-C(O)—, ($C_{1-6}$)alkoxy-($C_{1-6}$)alkyl, X$^3$=N—O—($C_{1-6}$)alkyl, and a glycine moiety; wherein X$^3$ is derived from a sugar moiety;

R$^7$ and R$^8$, each independently, are selected from the group of H, ($C_{1-20}$)alkyl, and ($C_{1-20}$)alkyl-C(O)—;

R$^9$ each independently, is R', R'—CH=N—O—, R'—($C_{1-6}$)alkyl-O—, R'—C(O)—NH—O—, R'—($C_{1-6}$)alkyl-S—, or R'—($C_{1-6}$)alkyl;

R' is H, ($C_{1-6}$)alkyl, halo, amino-O—, ($C_{1-6}$)alkyl-C(O)—, ($C_{2-6}$)alkenyl, cycloalkyl, heterocyclic, aryl-($C_{0-6}$)alkyl, or heretoaryl-($C_{0-6}$)alkyl, wherein each of said alkyl, cycloalkyl, heterocyclic, aryl and heteroaryl moieties is optionally substituted by one or more same or different substituents selected from the group of aryl, heteroaryl, hydroxyl, hydrosulfide, alkyl, alkoxy, alkenyl, halogen, nitro, cyano, ester, amine, amide, carboxyl, and alkyl-carbonyl groups;

AA₁ is an amino acid moiety selected from the group of Cys, Asp, Glu, Phe, Gly, His, Ile, Lys, Leu, Met, Asn, Pro, Gln, Arg, Ser, Thr, Val, Trp, and Tyr; and AA₂ is absent or an amino acid moiety selected from the group of His, Gln, Ala, Cys, Glu, Phe, Ile, Met, Asn, Ser, Thr, Val, and Tyr;

wherein each of the amino acid moieties for AA₁ or AA₂ is optionally substituted by halo, $(C_{1-20})$alkyl, allyl-$(C_{1-20})$alkyl, $(C_{0-20})$alkoxy-C(O)—$(C_{1-20})$alkyl, amino$(C_{1-20})$alkyl, aryl-$(C_{1-20})$alkyl, heteroaryl-$(C_{1-20})$alkyl, aryl-$(C_{1-20})$alkyl-CH=N—O—, aryl-$(C_{1-20})$alkoxy, aryl-$(C_{1-20})$alkyl-S—, aryl$(C_{1-20})$alkyl-C(O)—NH—O—, heteroaryl-$(C_{1-20})$alkyl-C(O)—NH—O—, and wherein each of the said alkyl, aryl and heteroaryl moieties is further optionally substituted by one or more same or different subtituents selected from the group of aryl, heteroaryl, alkenyl, alkoxy, alkyl, halo, hydroxyl, amine, amide, carboxyl, ester groups;

or a pharmaceutically acceptable salt, solvate, hydrate, or stereoisomer thereof.

In certain embodiments of Formula (II):

a) $R^1$, $R^2$ and $R^3$ cannot be all H at the same time;

b) when n is 0 and $R^3$ is H, AA₂ is a substituted amino acid moiety; and c) when $R^3$ is —OH, at least one of $R^1$ and $R^2$ must be $(C_{1-6})$alkyl-C(O)O—$(C_{1-6})$alkyl.

In certain embodiments, AA₁ is Leu that is optionally substituted.

In certain embodiments, AA₂ is a disubstituted histidine.

In one embodiment of the invention, at least one of $R^1$ and $R^2$ is H, $(C_{1-6})$alkyl-C(O)O—$(C_{1-6})$alkyl, or $(C_{1-6})$alkyl, wherein each alkyl moiety is optionally substituted by one or more carboxyl, hydroxyl, or alkoxy groups.

Certain embodiments of the invention provide that n is 1, and $R^9$ is R', R'—CH=N—O—, R'—$(C_{1-6})$alkyl-O—, R'—C(O)—NH—O—, R'—$(C_{1-6})$alkyl-S—, or R'—$(C_{1-6})$alkyl.

For example, R' can be one of the following:

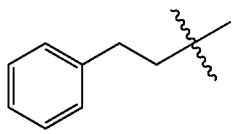

A-1

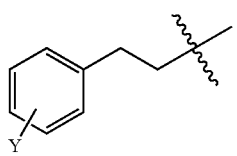

A-2

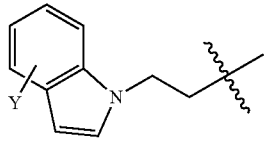

A-3

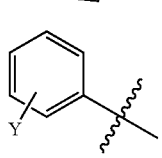

A-4

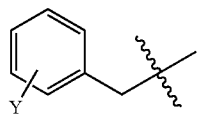

A-5

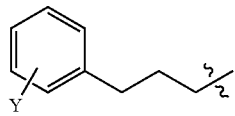

A-6

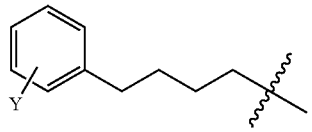

A-7

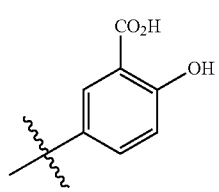

A-8

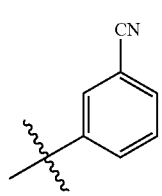

A-9

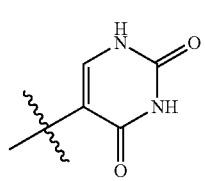

A-10

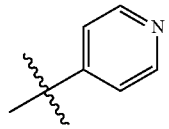

A-11

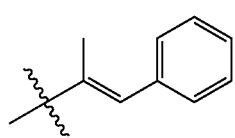

A-12

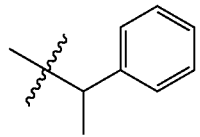

A-13

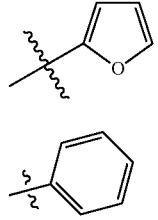

A-14

A-15

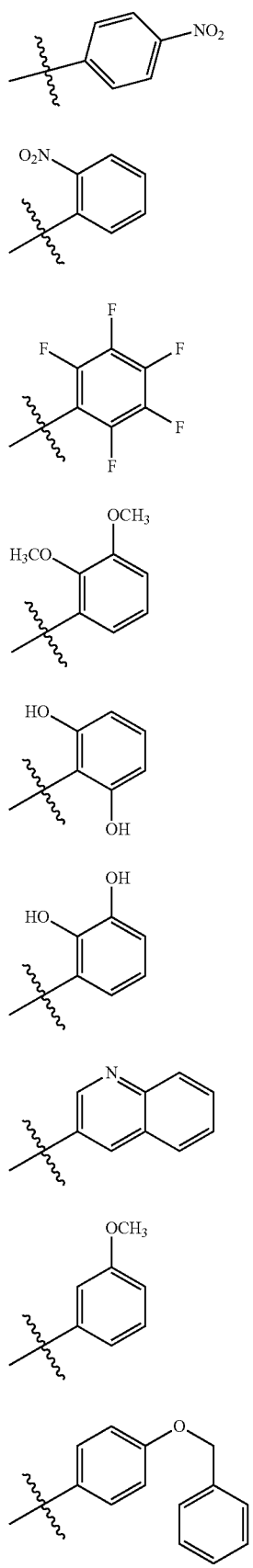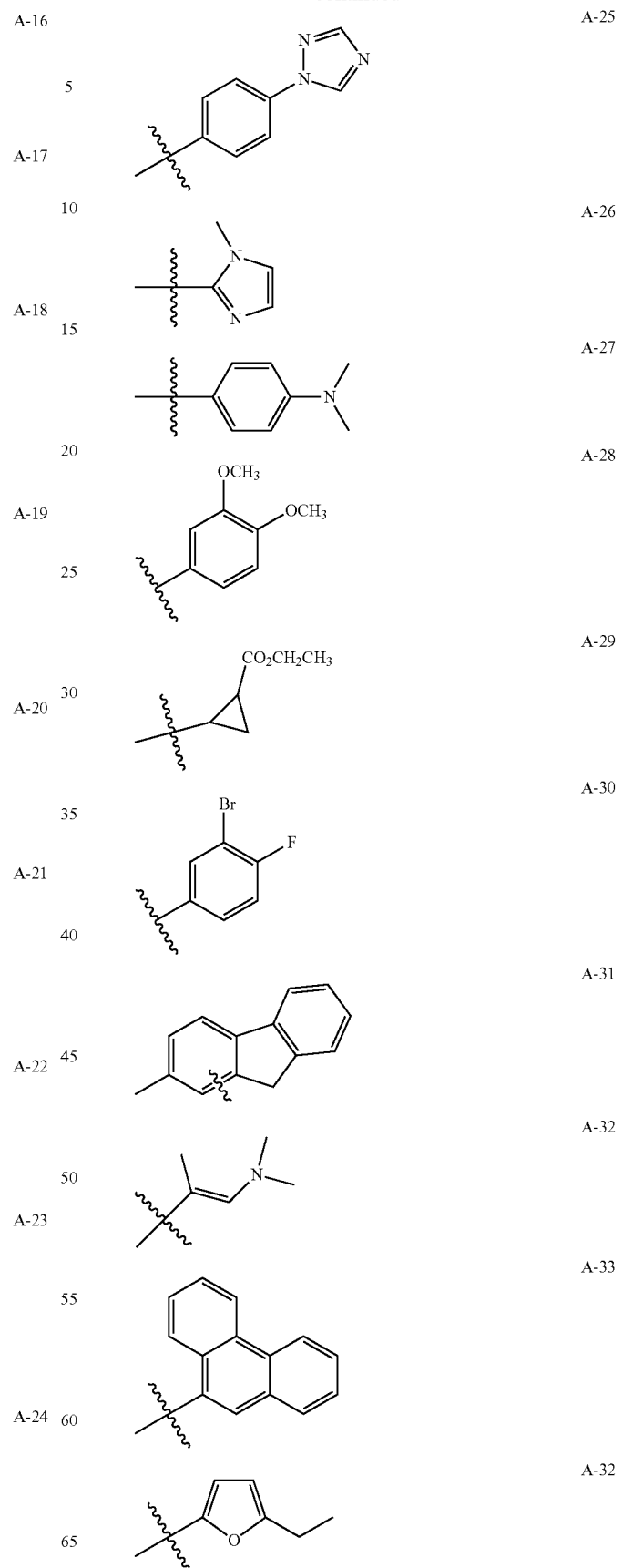

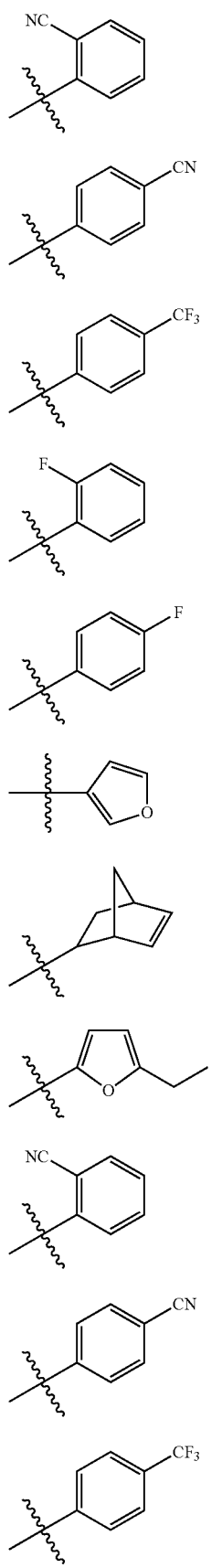
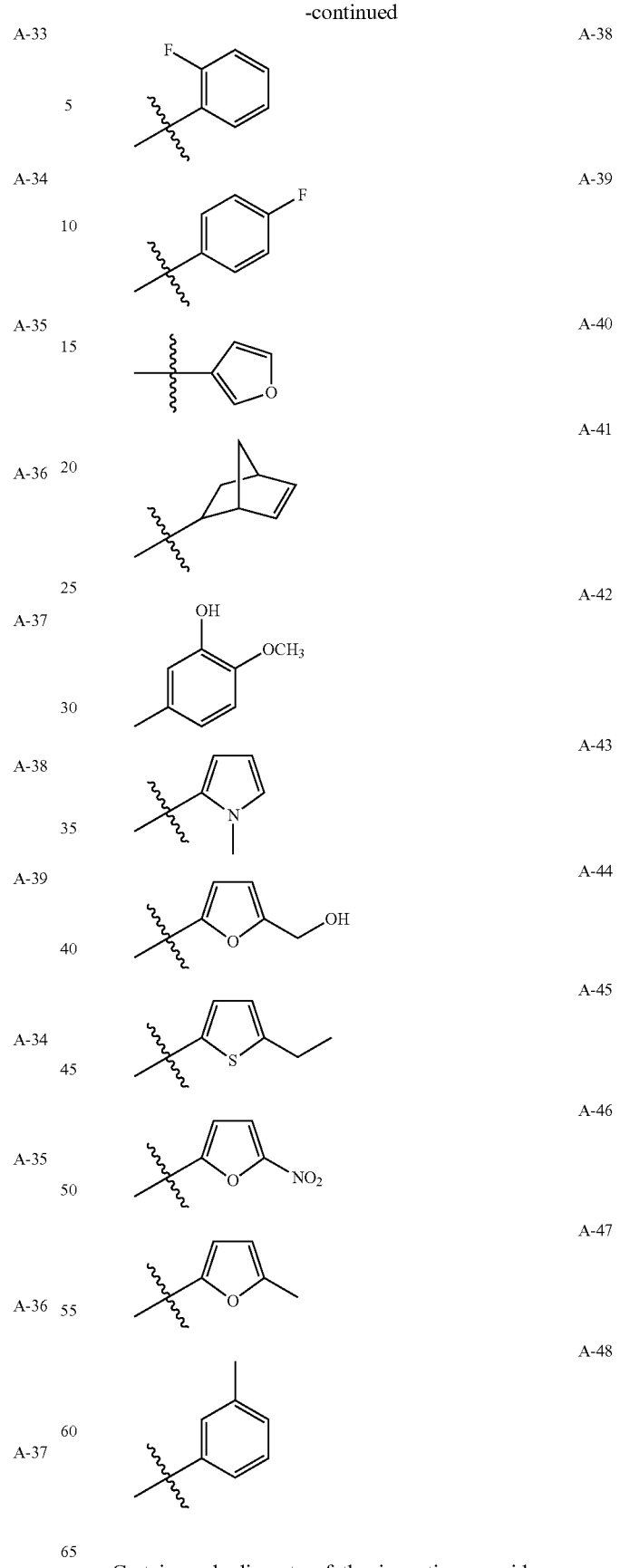
Certain embodiments of the invention provide a compound of Formula (I) according to Formula (A) or (A'):

(A)

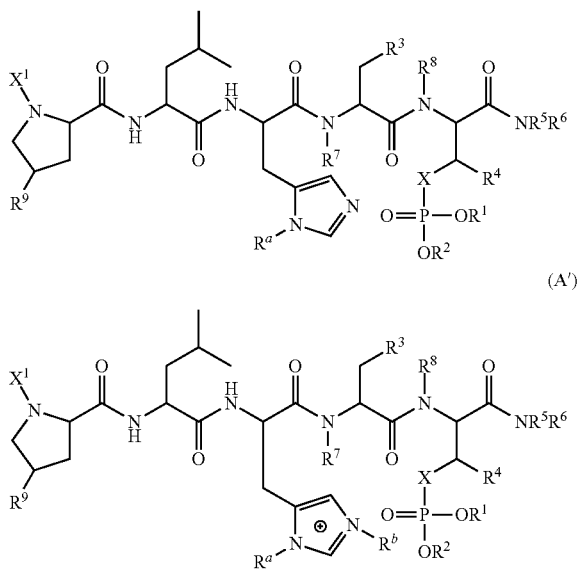

(A')

Wherein

X is O, CH$_2$, or CF$_2$;

X$^1$ is H or (C$_{1-6}$)alkyl-C(O)—;

R$^1$ and R$^2$, each independently, are selected from the group of H, (C$_{1-6}$)alkyl-C(O)O—(C$_{1-6}$)alkyl-, (C$_{1-20}$)alkyl, allyl-(C$_{1-20}$)alkyl, aryl-(C$_{1-20}$)alkyl-, heteroaryl-(C$_{1-20}$)alkyl, X$^2$O—C(O)—(C$_{1-6}$)alkyl-, and amino (C$_{1-6}$)alkyl, wherein each alkyl moiety that appears at the R$^1$ and R$^2$ positions is further optionally substituted by one or more carboxyl, hydroxyl, or alkoxy groups;

R$^3$ is H, —OH, (C$_{1-6}$)alkyl, (C$_{1-6}$)alkyl-C(O)O—, or (C$_{1-6}$)alkoxy;

R$^4$ is H, acyl, or (C$_{1-6}$)alkyl;

R$^5$ and R$^6$, each independently, are selected from the group of H, (C$_{1-6}$)alkyl, (C$_{1-6}$)alkyl-C(O)—, and (C$_{1-6}$)alkoxy-(C$_{1-6}$)alkyl;

R$^a$ is H, aryl-(C$_{1-20}$)alkyl, heteroaryl-(C$_{1-20}$)alkyl, (C$_{1-20}$)alkyl, allyl-(C$_{1-20}$)alkyl, (C$_{0-20}$)alkoxy-C(O)—(C$_{1-20}$)alkyl, or amino(C$_{1-20}$)alkyl; wherein each of the said alkyl, aryl, and heteroaryl moieties is further optionally substituted by one or more same or different substituents selected from the group of (C$_{1-6}$)alkyl, carboxyl, halo, hydroxyl, amine, and (C$_{1-6}$)alkoxy groups;

R$^b$ is selected from the group of allyl-(C$_{1-6}$)alkyl, aryl-(C$_{1-6}$)alkyl-, heteroaryl-(C$_{1-6}$)alkyl, and (C$_{1-6}$)alkyl optionally substituted by one or more carboxyl, (C$_{1-6}$)alkoxyl, or hydroxyl groups;

R$^7$ and R$^8$, each independently, are selected from the group of H, (C$_{1-6}$)alkyl, and (C$_{1-6}$)alkyl-C(O)—; and R$^9$ is H, halo, (C$_{2-6}$)alkenyl-(C$_{1-6}$)alkyl-O—, aryl-(C$_{1-6}$)alkyl-CH=N—O—, heteroaryl-(C$_{1-6}$)alkyl-CH=N—O—, or (C$_{1-6}$)alkyl; wherein each of said alkyl, aryl and heteroaryl moieties is optionally substituted by one or more same or different substituents selected from the group of aryl, heteroaryl, hydroxyl, alkyl, alkoxy, alkenyl, halogen, nitro, cyano, ester, amine, amide, carboxyl, and alkyl-carbonyl groups;

or a pharmaceutically acceptable salt, solvate, hydrate, or stereoisomer thereof.

In one embodiment of the invention, X$^1$ is CH$_3$C(O)—. Another embodiment provides that R$^7$ and R$^8$ are both H.

In certain embodiments, the invention provides a compound of Formula (I) according to Formula (B) or (B'):

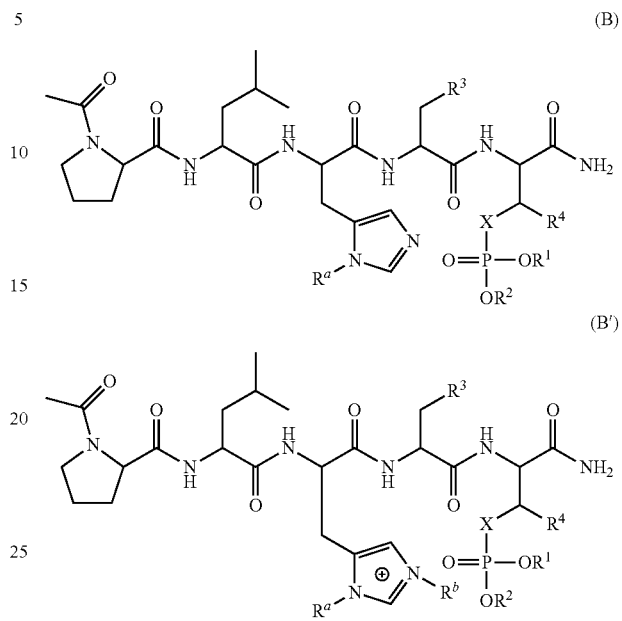

wherein

X is O or CH$_2$;

one of R$^1$ and R$^2$ is (C$_{1-6}$)alkyl-C(O)O—(C$_{1-6}$)alkyl- or H, and the other is selected from the group of H, (C$_{1-6}$)alkyl, allyl-(C$_{1-6}$)alkyl-, aryl-(C$_{1-6}$)alkyl-, (C$_{1-6}$)alkyl-C(O)O—(C$_{1-6}$)alkyl-, and heteroaryl-(C$_{1-6}$)alkyl-; wherein each alkyl moiety is further optionally substituted by one or more carboxyl, hydroxyl, or (C$_{1-6}$)alkoxy groups;

R$^3$ is H, —OH, (C$_{1-6}$)alkyl, (C$_{1-6}$)alkyl-C(O)O—, or (C$_{1-6}$)alkoxy;

R$^4$ is H or (C$_{1-6}$)alkyl; and

R$^a$ is H, (C$_{1-10}$)alkyl, aryl-(C$_{1-10}$)alkyl, or heteoaryl-(C$_{1-10}$)alkyl; wherein each of the said alkyl, aryl, and heteroaryl moieties is further optionally substituted by one or more same or different substituents selected from the group of carboxyl, hydroxyl, and (C1-6)alkoxy;

R$^b$ is selected from the group of allyl-(C$_{1-6}$)alkyl, aryl-(C$_{1-6}$)alkyl-, heteroaryl-(C$_{1-6}$)alkyl, and (C$_{1-6}$)alkyl optionally substituted by one or more carboxyl, (C$_{1-6}$)alkoxyl, or hydroxyl groups;

or a pharmaceutically acceptable salt, solvate, hydrate, or stereoisomer thereof.

In certain embodiments, R$^1$ is selected from the group of H, (C$_{1-6}$)alkyl-C(O)O—(C$_{1-6}$)alkyl-, aryl-(C$_{1-6}$)alkyl-, and (C$_{1-6}$)alkyl optionally substituted by one or more hydroxyl groups. For example, R$^1$ can be, without limitation, t-Bu-C(O)O—CH$_2$— ("POM").

In one embodiment, R$^3$ is H. In another embodiment, R$^3$ is —OH.

In certain embodiments, R$^a$ is phenyl-(C$_{1-10}$)alkyl.

In yet another embodiment, R$^4$ is (C$_{1-6}$)alkyl.

Certain exemplified compounds of the invention include, but are not limited to, the compounds of Table 1 as follows:

TABLE 1

| Comp. No. | X | R¹ | R² | R³ | Rᵃ | Rᵇ |
|---|---|---|---|---|---|---|
| A1 | O | t-Bu—C(O)O—CH₂— (or "POM") | POM | OH | H | absent |
| A2 | O | POM | POM | H | H | absent |
| A3 | CH₂ | POM | POM | OH | H | absent |
| A4 | CH₂ | POM | POM | H | H | absent |
| A5 (Qian108) | O | POM | POM | OH | Ph(CH₂)₈— | absent |
| A6 | O | POM | POM | H | Ph(CH₂)₈— | absent |
| A7 (Qian107) | O | POM | H | OH | Ph(CH₂)₈— | absent |
| A8 | O | POM | H | H | Ph(CH₂)₈— | absent |
| A9 (Qian109) | CH₂ | POM | POM | OH | Ph(CH₂)₈— | absent |
| A10 (Qian110) | O | POM | H | OH | Ph(CH₂)₈— | ⁀⁀⁀C(CH₃)₂CH₂OH |
| A11 (Qian115) | O | POM | H | H | Ph(CH₂)₈— | ⁀⁀⁀C(CH₃)₂CH₂OH |
| A12 | O | POM | H | OH | H | ⁀⁀⁀C(CH₃)₂CH₂OH |
| A13 | O | POM | H | OH | H | absent |

Other embodiments of the invention provides that one of R¹ and R² in any of the above formulae is H, and the other is selected from the group of allyl-($C_{1-6}$)alkyl, aryl-($C_{1-6}$) alkyl-, heteroaryl-($C_{1-6}$)alkyl.

Each of the ($C_{1-6}$)alkyl moieties at the R¹ and R² positions can be optionally substituted by one or more carboxyl or hydroxyl groups.

In one embodiment of the compounds according to any of the above formulae, R³ is H. In other embodiments, Rᵃ is aryl-($C_{1-10}$)alkyl.

By way of example, the invention further includes the following compounds:

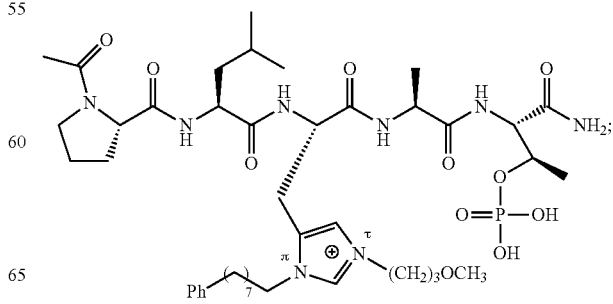

Compound No. A14

Compound No. A15

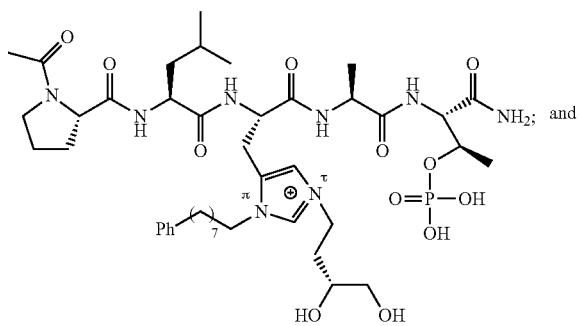

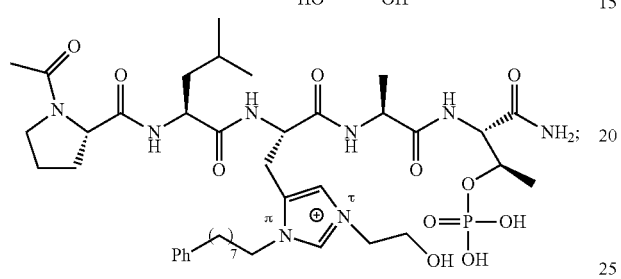

or a pharmaceutically acceptable salt, solvate, hydrate, or stereoisomer thereof.

In certain embodiments, the invention excludes individual compounds disclosed in WO2012/142245 and US 2012/0065146 A1.

In another aspect, the invention provides compounds listed in Table 2 as follows:

TABLE 2

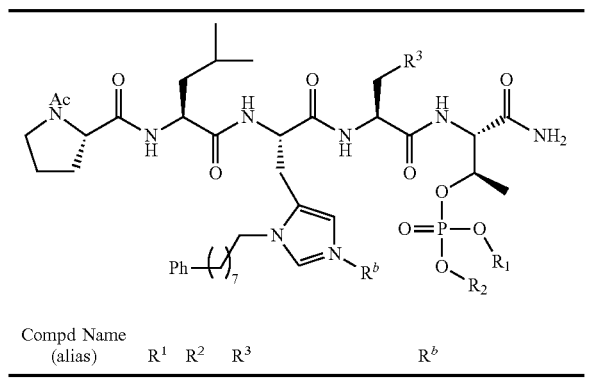

| Compd Name (alias) | $R^1$ | $R^2$ | $R^3$ | $R^b$ |
|---|---|---|---|---|
| Compound 4j (Qian30) | H | H | OH | absent |
| Qian48 | H | H | OH | ~~~CH₂CH₂CH₂OH |
| Compd. No. A16 (Qian113) | H | H | H | ~~~CH₂CH₂CH₂OH |
| Qian49 | H | H | OH | ~~~CH₂CH₂CH(OH)CH₂OH |
| Qian50 | H | H | OH | ~~~CH₂CH₂CH₂OCH₃ |
| Compd. No. A14 (Qian62) | H | H | H | ~~~CH₂CH₂CH₂OCH₃ |
| Qian51 | H | H | OH | ~~~CH₂CH₂CH₂COOH |
| Qian52 | H | H | OH | ~~~(CH₂)₄CH=CH₂ |
| Qian53 | H | H | OH | ~~~CH₂CH₂-(2-thienyl) |
| Qian54 | H | H | OH | ~~~CH₂CH₂-(2-furyl) |
| Qian55 | H | H | OH | ~~~C(Me)₃ |
| Qian63 | H | H | OH | ~~~(CH₂)₇Ph |
| Qian74 | H | H | OH | ~~~CH₂CH₂CH(OH)CH₂OH |
| Compd. No. A15 (Qian114) | H | H | H | ~~~CH₂CH₂CH(OH)CH₂OH |
| Qian75 | H | H | OH | ~~~CH₂CH₂CH(OH)CH₂OH |

TABLE 2-continued

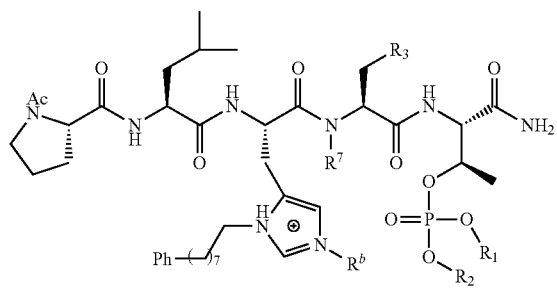

| Compd Name (alias) | R¹ | R² | R³ | R^b |
|---|---|---|---|---|
| Qian76 | H | H | OH | (structure with HO, OH) |
| Qian77 | H | H | OH | (structure with HO, OH) |

In some compounds of Table 2, the imidazole ring may have a positive charge; thus, the structure may be represented:

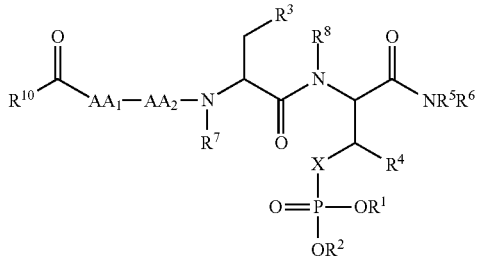

Another aspect is any compound delineated herein tagged with a HIV Tat sequence.

In another aspect, the invention provides a compound of Formula (I'):

Formula (I')

(structure shown)

or a pharmaceutically acceptable salt, solvate, hydrate, or stereoisomer thereof;

wherein
$R^{10}$ is

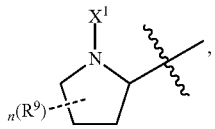

$(C_{1-6})$alkyl, amino, $(C_{2-6})$alkenyl, cycloalkyl, heterocyclic, aryl-$(C_{0-6})$alkyl, or heteroaryl-$(C_{0-6})$alkyl, wherein each of said alkyl, cycloalkyl, heterocyclic, aryl and heteroaryl moieties is optionally substituted by one or more same or different substituents selected from the group of aryl, heteroaryl, hydroxyl, hydrosulfide, alkyl, alkoxy, alkenyl, halogen, nitro, cyano, ester, amine, amide, carboxyl, and alkyl-carbonyl groups;

n is 0, 1, 2, or 3;

X is O, —$(C_{1-6})$alkyl-, or —$C(Y)_2$—; wherein Y, for each occurrence independently, is F, Cl, or Br;

$X^1$ is $(C_{1-6})$alkyl-C(O)—, or a polyethylene glycol moiety or a derivative thereof;

$R^1$ and $R^2$, each independently, are selected from the group of H, $(C_{1-6})$alkyl-C(O)O—$(C_{1-6})$alkyl-, $(C_{1-20})$alkyl, aryl-$(C_{1-20})$alkyl-, heteroaryl-$(C_{1-20})$alkyl, $X^2$O—C(O)—$(C_{1-6})$alkyl-, and amino$(C_{1-6})$alkyl, wherein each alkyl moiety that appears at the $R^1$ and $R^2$ positions is further optionally substituted by one or more carboxyl, hydroxyl, or alkoxy groups;

$X^2$ is H or $(C_{1-6})$alkyl; wherein the $(C_{1-6})$alkyl is optionally substituted by one or more hydroxyl, halo, or alkoxy groups;

$R^3$ is H, —OH, $(C_{1-6})$alkyl, $(C_{1-6})$alkyl-C(O)O—, or $(C_{1-6})$alkoxy;

$R^4$ is H, acyl, $(C_{1-6})$alkyl, $(C_{1-6})$alkyl-OC(O)O—, or $(C_{1-6})$alkyl-O—C(S)—O—;

$R^5$ and $R^6$, each independently, are selected from the group of H, $(C_{1-6})$alkyl, $(C_{1-6})$alkyl-C(O)—, $(C_{1-6})$alkoxy-$(C_{1-6})$alkyl, $X^3$=N—O—$(C_{1-6})$alkyl, and a glycine moiety; wherein $X^3$ is derived from a sugar moiety;

$R^7$ and $R^8$, each independently, are selected from the group of H, $(C_{1-20})$alkyl, and $(C_{1-20})$alkyl-C(O)—;

$R^9$ each independently, is R', R'—CH=N—O—, R'—$(C_{1-6})$alkyl-C(O)—, R'—C(O)—NH—O—, R'—$(C_{1-6})$alkyl-S—, or R'—$(C_{1-6})$alkyl;

R' is H, $(C_{1-6})$alkyl, halo, amino-O—, $(C_{1-6})$alkyl-C(O)—, $(C_{2-6})$alkenyl, cycloalkyl, heterocyclic, aryl-$(C_{0-6})$alkyl, or heteroaryl-$(C_{0-6})$alkyl, wherein each of said alkyl, cycloalkyl, heterocyclic, aryl and heteroaryl moieties is optionally substituted by one or more same or different substituents selected from the group of aryl, heteroaryl, hydroxyl, hydrosulfide, alkyl, alkoxy, alkenyl, halogen, nitro, cyano, ester, amine, amide, carboxyl, and alkyl-carbonyl groups;

$AA_1$ is an amino acid moiety selected from the group of Cys, Asp, Glu, Phe, Gly, His, Ile, Lys, Leu, Met, Asn, Pro, Gln, Arg, Ser, Thr, Val, Trp, and Tyr; and $AA_2$ is absent or an amino acid moiety selected from the group of His, Gln, Ala, Cys, Glu, Phe, Ile, Met, Asn, Ser, Thr, Val, and Tyr;

wherein each of the amino acid moieties for $AA_1$ or $AA_2$ is optionally substituted by halo, $(C_{1-20})$alkyl, allyl-$(C_{1-20})$alkyl, $(C_{0-20})$alkoxy-C(O)—$(C_{1-20})$alkyl, amino$(C_{1-20})$alkyl, aryl-$(C_{1-20})$alkyl, heteroaryl-$(C_{1-20})$alkyl, aryl-$(C_{1-20})$alkyl-CH=N—O—, aryl-$(C_{1-20})$alkoxy, aryl-$(C_{1-20})$alkyl-S—, aryl-$(C_{1-20})$alkyl-C(O)—NH—O—, heteroaryl-$(C_{1-20})$alkyl-C(O)—NH—O—, and wherein each of the said alkyl, aryl and heteroaryl moieties is further optionally substituted by one or more same or different substituents selected from the group of aryl, heteroaryl, alkenyl, alkoxy, alkyl, halo, hydroxyl, amine, amide, carboxyl, ester groups;
provided that
a) when $R^1$, $R^2$ and $R^3$ cannot be all H at the same time;
b) when n is 0 and $R^3$ is H, $AA_2$ is a substituted amino acid moiety; and
c) when $R^3$ is —OH, at least one of $R^1$ and $R^2$ must be $(C_{1-6})$alkyl-C(O)O—$(C_{1-6})$alkyl.

In certain embodiments, the compound is of Formula (II'):

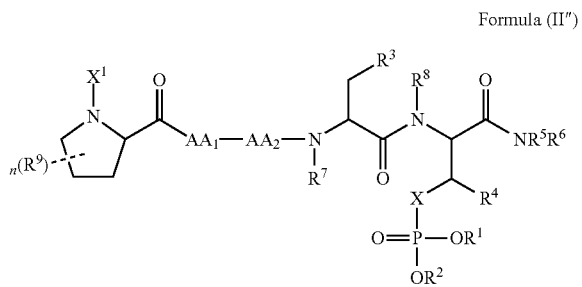

Formula (II'')

or a pharmaceutically acceptable salt, solvate, hydrate, or stereoisomer thereof;
wherein
n is 0, 1, 2, or 3;
X is O, —$(C_{1-6})$alkyl-, or —$C(Y)_2$—; wherein Y, for each occurrence independently, is F, Cl, or Br;
$X^1$ is $(C_{1-6})$alkyl-C(O)—, or a polyethylene glycol moiety or a derivative thereof;
$R^1$ and $R^2$, each independently, are selected from the group of H, $(C_{1-6})$alkyl-C(O)O—$(C_{1-6})$alkyl-, $(C_{1-20})$alkyl, allyl-$(C_{1-20})$alkyl, aryl-$(C_{1-20})$alkyl-, heteroaryl-$(C_{1-20})$alkyl, $X^2$O—C(O)—$(C_{1-6})$alkyl-, and amino$(C_{1-6})$alkyl, wherein each alkyl moiety that appears at the $R^1$ and $R^2$ positions is further optionally substituted by one or more carboxyl, hydroxyl, or alkoxy groups;
$X^2$ is H or $(C_{1-6})$alkyl; wherein the $(C_{1-6})$alkyl is optionally substituted by one or more hydroxyl, halo, or alkoxy groups;
$R^3$ is H, —OH, $(C_{1-6})$alkyl, $(C_{1-6})$alkyl-C(O)O—, or $(C_{1-6})$alkoxy;
$R^4$ is H, acyl, $(C_{1-6})$alkyl, $(C_{1-6})$alkyl-OC(O)O—, or $(C_{1-6})$alkyl-O—C(S)—O—;
$R^5$ and $R^6$, each independently, are selected from the group of H, $(C_{1-6})$alkyl, $(C_{1-6})$alkyl-C(O)—, $(C_{1-6})$alkoxy-$(C_{1-6})$alkyl, $X^3$=N—O—$(C_{1-6})$alkyl, and a glycine moiety; wherein $X^3$ is derived from a sugar moiety;
$R^7$ and $R^8$, each independently, are selected from the group of H, $(C_{1-20})$alkyl, and $(C_{1-20})$alkyl-C(O)—;
$R^9$ each independently, is R', R'—CH=N—O—, R'—$(C_{1-6})$alkyl-O—, R'—C(O)—NH—O—, R'—$(C_{1-6})$alkyl-S—, or R'—$(C_{1-6})$alkyl;
R' is H, $(C_{1-6})$alkyl, halo, amino-O—, $(C_{1-6})$alkyl-C(O)—, $(C_{2-6})$alkenyl, cycloalkyl, heterocyclic, aryl-$(C_{0-6})$alkyl, or heretoaryl-$(C_{0-6})$alkyl, wherein each of said alkyl, cycloalkyl, heterocyclic, aryl and heteroaryl moieties is optionally substituted by one or more same or different substituents selected from the group of aryl, heteroaryl, hydroxyl, hydrosulfide, alkyl, alkoxy, alkenyl, halogen, nitro, cyano, ester, amine, amide, carboxyl, and alkyl-carbonyl groups;
$AA_1$ is an amino acid moiety selected from the group of Cys, Asp, Glu, Phe, Gly, His, Ile, Lys, Leu, Met, Asn, Pro, Gln, Arg, Ser, Thr, Val, Trp, and Tyr; and $AA_2$ is absent or an amino acid moiety selected from the group of His, Gln, Ala, Cys, Glu, Phe, Ile, Met, Asn, Ser, Thr, Val, and Tyr;
wherein each of the amino acid moieties for $AA_1$ or $AA_2$ is optionally substituted by halo, $(C_{1-20})$alkyl, allyl-$(C_{1-20})$alkyl, $(C_{0-20})$alkoxy-C(O)—$(C_{1-20})$alkyl, amino$(C_{1-20})$alkyl, aryl-$(C_{1-20})$alkyl, heteroaryl-$(C_{1-20})$alkyl, aryl-$(C_{1-20})$alkyl-CH=N—O—, aryl-$(C_{1-20})$alkoxy, aryl-$(C_{1-20})$alkyl-S—, aryl-$(C_{1-20})$alkyl-C(O)—NH—O—, heteroaryl-$(C_{1-20})$alkyl-C(O)—NH—O—, and wherein each of the said alkyl, aryl and heteroaryl moieties is further optionally substituted by one or more same or different substituents selected from the group of aryl, heteroaryl, alkenyl, alkoxy, alkyl, halo, hydroxyl, amine, amide, carboxyl, ester groups;
provided that
a) when $R^1$, $R^2$ and $R^3$ cannot be all H at the same time;
b) when n is 0 and $R^3$ is H, $AA_2$ is a substituted amino acid moiety; and
b) when $R^3$ is —OH, at least one of $R^1$ and $R^2$ must be $(C_{1-6})$alkyl-C(O)O—$(C_{1-6})$alkyl.

In certain embodiments of Formula (I') or (II'), $AA_1$ is Leu, and $AA_2$ is His or Gln, wherein each of $AA_1$ and $AA_2$ is optionally substituted.

In certain embodiments, at least one of $R^1$ and $R^2$ is H, $(C_{1-6})$alkyl-C(O)O—$(C_{1-6})$alkyl-, or $(C_{1-6})$alkyl, wherein each alkyl moiety is optionally substituted by one or more carboxyl, hydroxyl, or alkoxy groups.

In certain embodiments, the compound is a compound of Formula (AA):

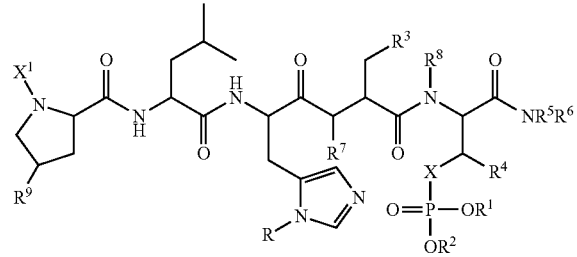

(AA)

Wherein
X is O, $CH_2$, or $CF_2$;
$X^1$ is $(C_{1-6})$alkyl-C(O)—;
one of $R^1$ and $R^2$ is $(C_{1-6})$alkyl-C(O)O—$(C_{1-6})$alkyl- or H, the other is selected from the group of H, $(C_{1-6})$alkyl, allyl-$(C_{1-6})$alkyl, aryl-$(C_{1-6})$alkyl-, $(C_{1-6})$alkyl-C(O)O—$(C_{1-6})$alkyl-, and heteroaryl-$(C_{1-6})$alkyl-; wherein each alkyl moiety is further optionally substituted by one or more carboxyl, hydroxyl, or $(C_{1-6})$alkoxy groups;
$R^3$ is H, —OH, $(C_{1-6})$alkyl, $(C_{1-6})$alkyl-C(O)O—, or $(C_{1-6})$alkoxy;
$R^4$ is H, acyl, or $(C_{1-6})$alkyl;
$R^5$ and $R^6$, each independently, are selected from the group of H, $(C_{1-6})$alkyl, $(C_{1-6})$alkyl-C(O)—, and $(C_{1-6})$alkoxy-$(C_{1-6})$alkyl;
R is H, aryl-$(C_{1-20})$alkyl, heteroaryl-$(C_{1-20})$alkyl, $(C_{1-20})$alkyl, allyl-$(C_{1-20})$alkyl, $(C_{0-20})$alkoxy-C(O)—$(C_{1-20})$alkyl, or amino$(C_{1-20})$alkyl; wherein each of the said alkyl, aryl, and heteroaryl moieties is further optionally substituted by one or more same or different substituents selected from the group of $(C_{1-6})$alkyl, carboxyl, halo, hydroxyl, amine, and $(C_{1-6})$alkoxy groups;

$R^7$ and $R^8$, each independently, are selected from the group of H, $(C_{1-6})$alkyl, and $(C_{1-6})$alkyl-C(O)—; and $R^9$ is H, halo, $(C_{2-6})$alkenyl-$(C_{1-6})$alkyl-O—, aryl-$(C_{1-6})$alkyl-CH=N—O—, heteroaryl-$(C_{1-6})$alkyl-CH=N—O—, or $(C_{1-6})$alkyl; wherein each of said alkyl, aryl and heteroaryl moieties is optionally substituted by one or more same or different substituents selected from the group of aryl, heteroaryl, hydroxyl, alkyl, alkoxy, alkenyl, halogen, nitro, cyano, ester, amine, amide, carboxyl, and alkyl-carbonyl groups;

or a pharmaceutically acceptable salt, solvate, hydrate, or stereoisomer thereof.

In certain embodiments, $X^1$ is $CH_3C(O)$—, and $R^1$ and $R^8$ are both H.

In certain embodiments, the compound is a compound of Formula (B):

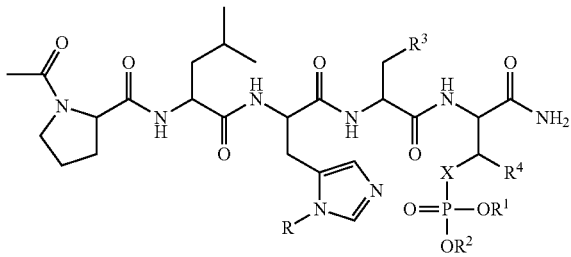

(B)

Wherein
X is O or $CH_2$;
one of $R^1$ and $R^2$ is $(C_{1-6})$alkyl-C(O)O—$(C_{1-6})$alkyl- or H, and the other is selected from the group of H, $(C_{1-6})$alkyl, allyl-$(C_{1-6})$alkyl-, aryl-$(C_{1-6})$alkyl-, $(C_{1-6})$alkyl-C(O)O—$(C_{1-6})$alkyl-, and heteroaryl-$(C_{1-6})$alkyl-; wherein each alkyl moiety is further optionally substituted by one or more carboxyl, hydroxyl, or $(C_{1-6})$alkoxy groups;
$R^3$ is H, —OH, $(C_{1-6})$alkyl, $(C_{1-6})$alkyl-C(O)O—, or $(C_{1-6})$alkoxy;
$R^4$ is H or $(C_{1-6})$alkyl; and
R is H, aryl-$(C_{1-10})$alkyl, aryl-$(C_{1-10})$alkyo, or heteoaryl-$(C_{1-10})$alkyl; wherein each of the said alkyl, aryl, and heteroaryl moieties is further optionally substituted by one or more same or different substituents selected from the group of carboxyl, hydroxyl, and $(C_{1-6})$alkoxy;
or a pharmaceutically acceptable salt, solvate, hydrate, or stereoisomer thereof.

In certain embodiments, one of $R^1$ and $R^2$ is $(C_{1-6})$alkyl-C(O)O—$(C_{1-6})$alkyl-, and the other is selected from the group of H, $(C_{1-6})$alkyl-C(O)O—$(C_{1-6})$alkyl-, aryl-$(C_{1-6})$alkyl-, and $(C_{1-6})$alkyl optionally substituted by one or more hydroxyl groups.

In certain embodiments, one of $R^1$ and $R^2$ is t-Bu-C(O)O—$CH_2$— ("POM"), and the other is selected from the group of H, t-Bu-C(O)O—$CH_2$—, —$(CH_2)_2$OH, and benzyl.

In certain embodiments, $R^3$ is H or —OH.

In certain embodiments, R is H or phenyl-$(C_{1-10})$alkyl.

In certain embodiments, $R^4$ is $(C_{1-6})$alkyl.

In certain embodiments, the compound is selected from Compound Nos. A1-A13 provided in Table 1, or a pharmaceutically acceptable salt, solvate, hydrate, or stereoisomer thereof.

In certain embodiments, one of $R^1$ and $R^2$ is H, and the other is selected from the group of allyl-$(C_{1-6})$alkyl, aryl-$(C_{1-6})$alkyl-, heteroaryl-$(C_{1-6})$alkyl, and $(C_{1-6})$alkyl optionally substituted by one or more carboxyl or hydroxyl groups.

In certain embodiments, $R^3$ is H.

In certain embodiments, R is aryl-$(C_{1-10})$alkyl.

In another aspect, the invention provides a compound of Formula (IA):

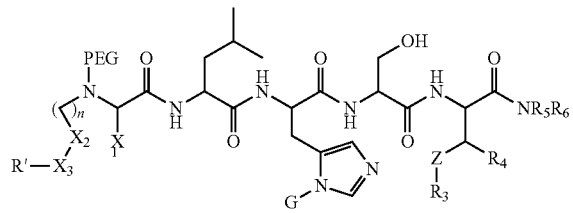

Formula (IA)

wherein
Z is O, $CH_2$, or $CF_2$;
n is 0, 1 or 2;
$X_1$ is H; and $X_2$ is a bond or $CH_2$; or $X_1$ and $X_2$, taken together with the bonds they are connected to, form a 5-membered heterocyclic ring;
$R_3$ is H or $(X_4O)_2P(O)$—;
$R_4$ is H, or $(C_{1-6})$alkyl;
$R_5$ and $R_6$ are both H; or one of $R_5$ and $R_6$ is H, the other is $X_5$—O—$(C_{1-6})$alkyl or a glycine moiety; wherein $X_5$ is —N=$R_9$, and $R_9$ is derived from a sugar moiety;
R'—$X_3$ is R', R'—CH=N—O—, R'—$(C_{1-6})$alkyl-O—, R'—C(O)—NH—O—, R'—$(C_{1-6})$alkyl-S—, or R'—$(C_{1-6})$alkyl-;
R' is H, amino-O—, $(C_{1-6})$alkyl-C(O)—, cycloalkyl, heterocyclic, aryl-$(C_{0-6})$alkyl, or heretoaryl-$(C_{0-6})$alkyl, wherein each of said cycloalkyl, heterocyclic, aryl and heteroaryl moieties is optionally substituted by one or more same or different substituents selected from the group of aryl, heteroaryl, hydroxyl, hydrosulfide, alkyl, alkoxy, alkenyl, halogen, nitro, cyano, ester, amine, amide, carboxyl, and alkyl-carbonyl groups; and
G is H, alkenyl-$(C_{1-20})$alkyl, $(C_{1-6})$alkoxy-carbonyl-$(C_{1-20})$alkyl, hydroxyl-carbonyl-$(C_{1-20})$alkyl, amino$(C_{1-20})$alkyl, aryl-$(C_{1-20})$alkyl, $(C_{1-20})$alkyl, or heretoaryl-$(C_{1-20})$alkyl, wherein each of alkyl, aryl and heretoaryl moieties is optionally substituted by one or more halogen, hydroxyl or alkoxy groups;
or a pharmaceutically acceptable salt, solvate, hydrate, or stereoisomer thereof;
provided that the compound is not a compound disclosed in PCT/US2012/033259 (WO2012/142245) or US 2012/0065146.

In one embodiment of the compounds of Formula (IA), PEG is

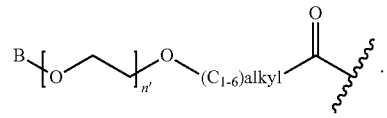

One embodiment provides that B is H, $(C_{1-6})$alkyl, or hydrosulfide-$(C_{1-6})$alkyl-C(O)—NH—$(C_{1-6})$alkyl, wherein each $(C_{1-6})$alkyl moiety as appears herein, independently, is further optionally substituted by an amino or N-Fmoc-amino group; and n' is an integer selected from 5-200.

In another embodiment, $X_1$ and $X_2$, taken together with the bonds they are connected to, form a 5-membered heterocyclic ring. In still another embodiment, $R_5$ and $R_6$ are both H.

In another aspect, the invention provides compounds of Formula (a):

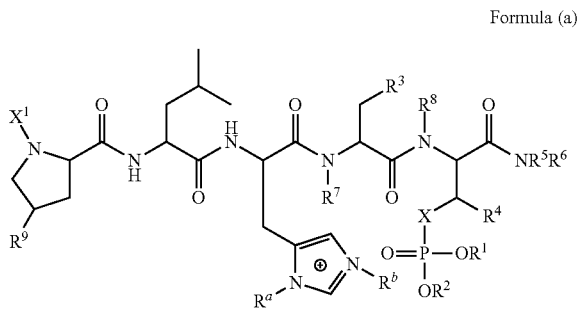

Formula (a)

wherein
X is O, $CH_2$, or $CF_2$;
$X_1$ is

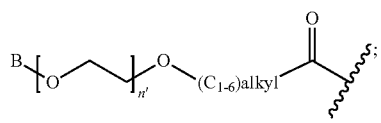

B is H, $(C_{1-6})$alkyl, or hydrosulfide-$(C_{1-6})$alkyl-C(O)—NH—$(C_{1-6})$alkyl, wherein each $(C_{1-6})$alkyl moiety, independently, is further optionally substituted by an amino or N-Fmoc-amino group;
n' is an integer selected from 5-100;
$R_1$, $R_2$, $R_5$, $R_6$, $R_7$ and $R_8$ are each H;
$R_3$ is OH;
$R_4$ is —$CH_3$;
$R_9$ is R'—$X_3$;
R'—$X_3$ is R', R'—CH=N—O—, R'—$(C_{1-6})$alkyl-O—, R'—C(O)—NH—O—, R'—$(C_{1-6})$alkyl-S—, or R'—$(C_{1-6})$alkyl;
R' is H, $H_2$NO—, $(C_{2-6})$alkenyl, phenyl-$(C_{0-6})$alkyl, furanyl-$(C_{0-6})$alkyl, thiophenyl-$(C_{0-6})$alkyl, N-indolyl-$(C_{1-6})$alkyl, fluorenyl, $(C_{3-8})$cycloalkyl, imidazolyl, quinolinyl, pyridinyl, pyrimidinyl, dioxo-pyrimidinyl, phenanthrenyl, or bicyclo[12.2.1]hept-2-enyl, wherein $R_3$ is further optionally substituted by one or more substituents selected from the group of halogen, $(C_{6-10})$aryl, heteroaryl, $(C_{1-6})$alkyl, $(C_{1-6})$alkoxy, hydroxyl, hydrosulfide, $(C_{1-6})$alkoxy-carbonyl, cyano, $(C_{6-10})$aryl-$(C_{1-6})$alkoxy, hydroxyl$(C_{1-6})$alkyl, trifluoromethyl, amino, and nitro; and
$R_a$ is H, aryl-$(C_{1-20})$alkyl, heteroaryl-$(C_{1-20})$alkyl, $(C_{1-20})$alkyl, allyl-$(C_{1-20})$alkyl, $(C_{0-20})$alkoxy-C(O)—$(C_{1-20})$alkyl, or amino$(C_{1-20})$alkyl; wherein each of the said alkyl, aryl, and heteroaryl moieties is further optionally substituted by one or more same or different substituents selected from the group of $(C_{1-6})$alkyl, carboxyl, halo, hydroxyl, amine, and $(C_{1-6})$alkoxy groups;
$R^b$ is selected from the group of allyl-$(C_{1-6})$alkyl, aryl-$(C_{1-6})$alkyl-, heteroaryl-$(C_{1-6})$alkyl, and $(C_{1-6})$alkyl optionally substituted by one or more carboxyl, $(C_{1-6})$alkoxyl, or hydroxyl groups;
or a pharmaceutically acceptable salt, solvate, hydrate, or stereoisomer thereof;

provided that the compound is not a compound disclosed in PCT/US2012/033259 (WO2012/142245) or US 2012/0065146.

In certain embodiments of Formula (a), Z is O or $CH_2$; and n' is an integer between 5 and 20.

In one embodiment, B is $(C_{1-6})$alkyl or hydrosulfide-$(C_{1-6})$alkyl-C(O)—NH—$(C_{1-6})$alkyl, wherein each $(C_{1-6})$ alkyl moiety as appears herein, independently, is further optionally substituted by an amino or N-Fmoc-amino group. For example, B is methyl,

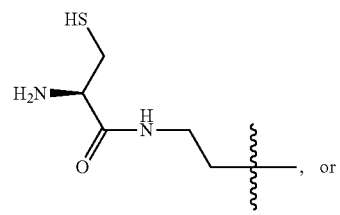

, or

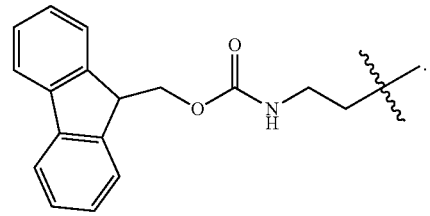

.

In one embodiment, R'—$X_3$ is R', R'—CH=N—O—, R'—C(O)—NH—O—, or R'—$(CH_2)_2$—O—, wherein R' is H, $H_2$NO—, or phenyl-$(C_{1-6})$alkyl.

For example, R' is selected from the group of

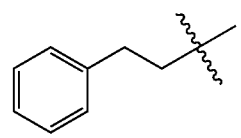
A-1

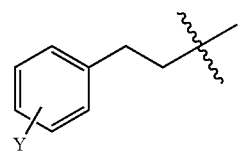
A-2

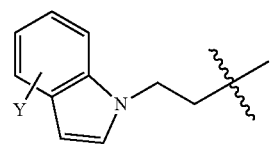
A-3

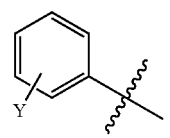
A-4

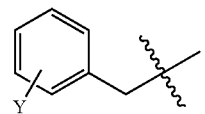
A-5

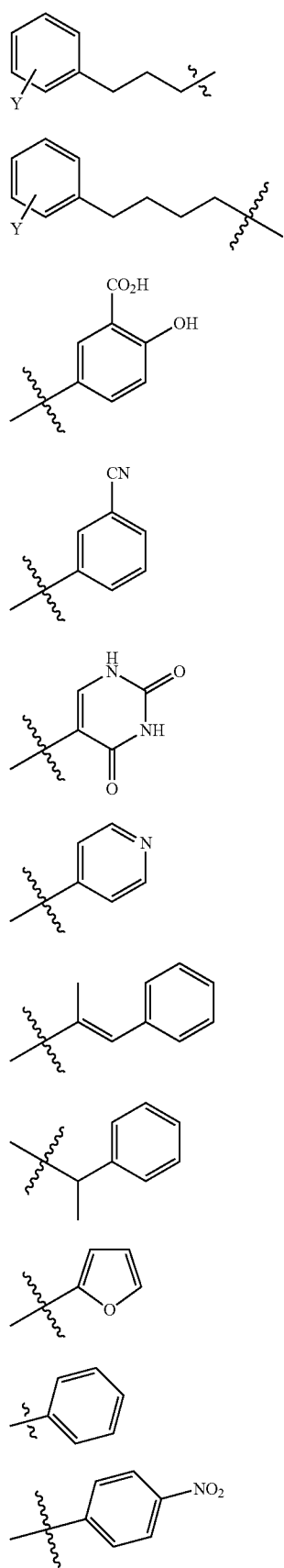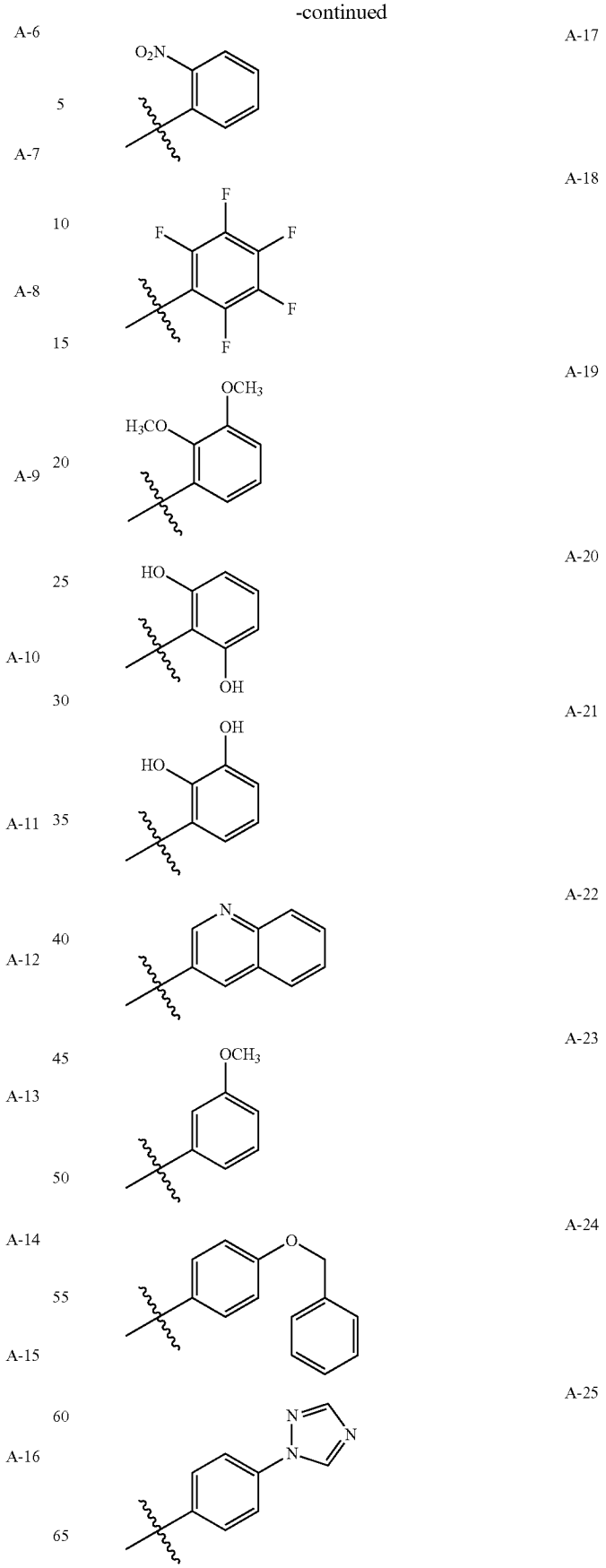

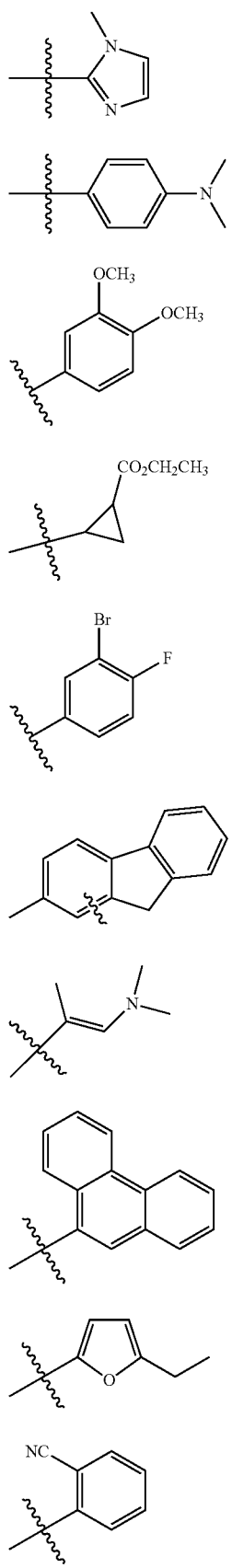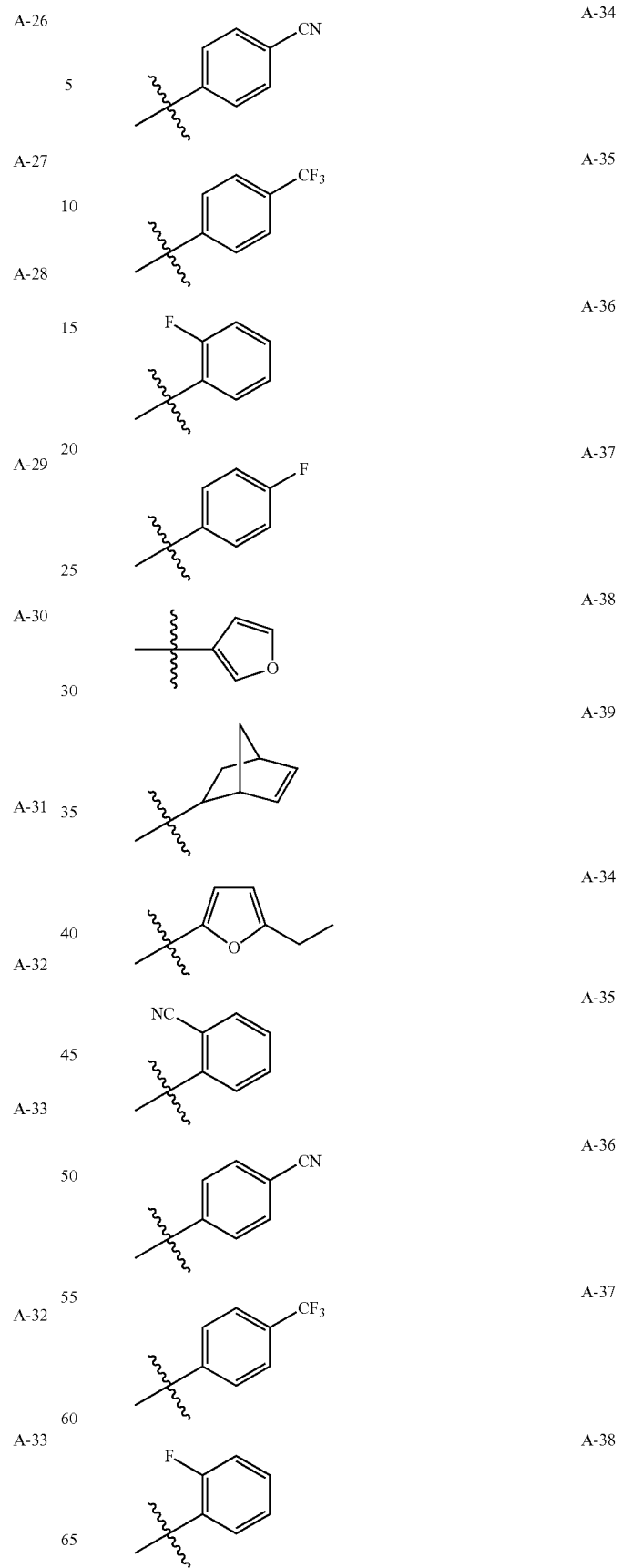

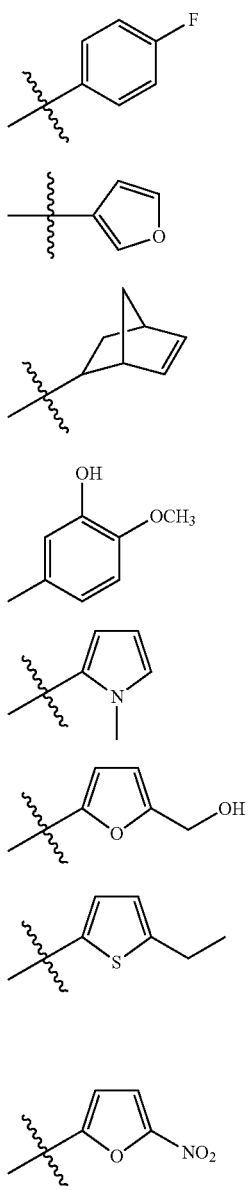

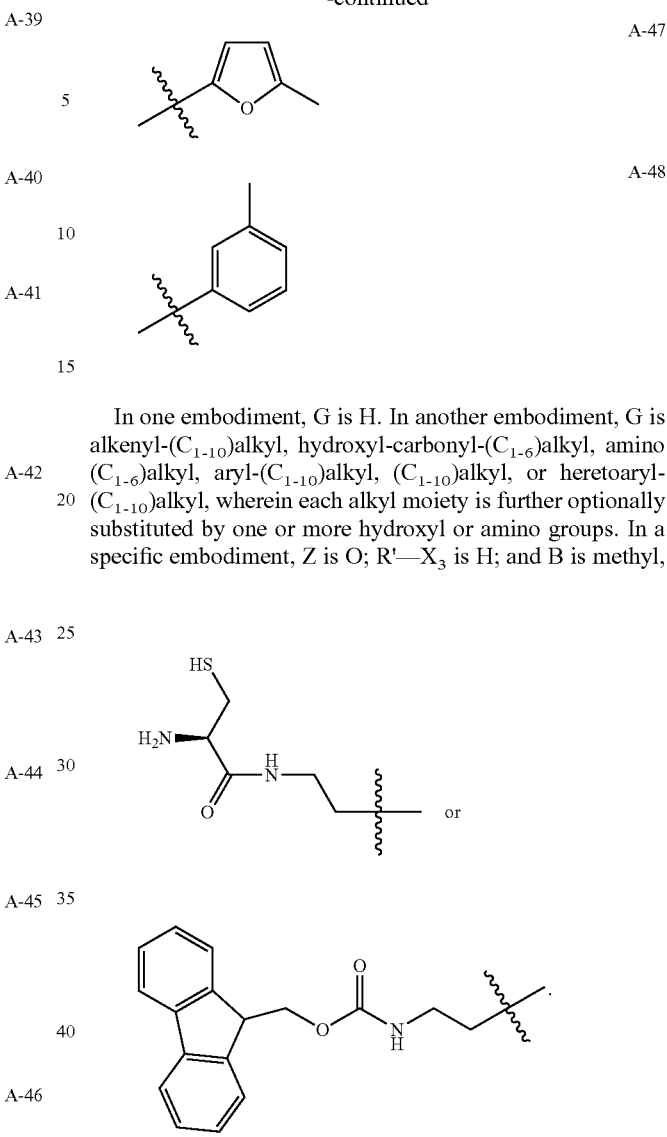

In one embodiment, G is H. In another embodiment, G is alkenyl-($C_{1-10}$)alkyl, hydroxyl-carbonyl-($C_{1-6}$)alkyl, amino ($C_{1-6}$)alkyl, aryl-($C_{1-10}$)alkyl, ($C_{1-10}$)alkyl, or heteroaryl-($C_{1-10}$)alkyl, wherein each alkyl moiety is further optionally substituted by one or more hydroxyl or amino groups. In a specific embodiment, Z is O; R'—$X_3$ is H; and B is methyl, In certain embodiments, the compound is not a compound represented by any of the following structures:

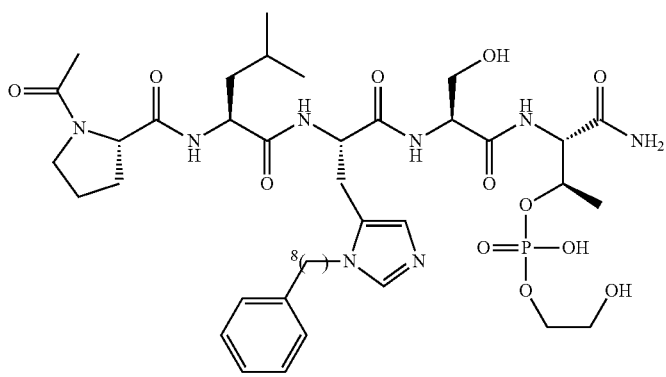

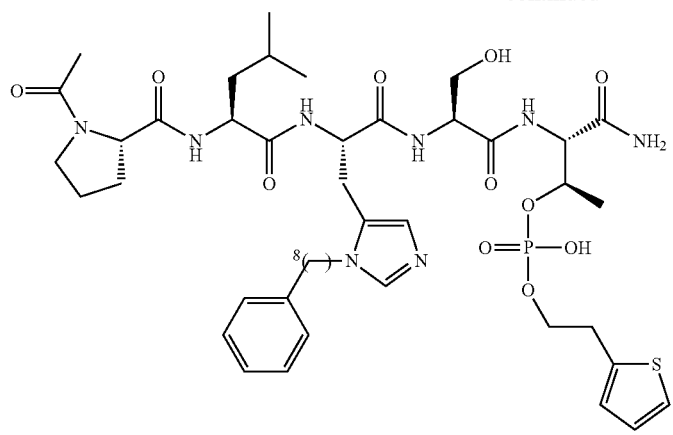
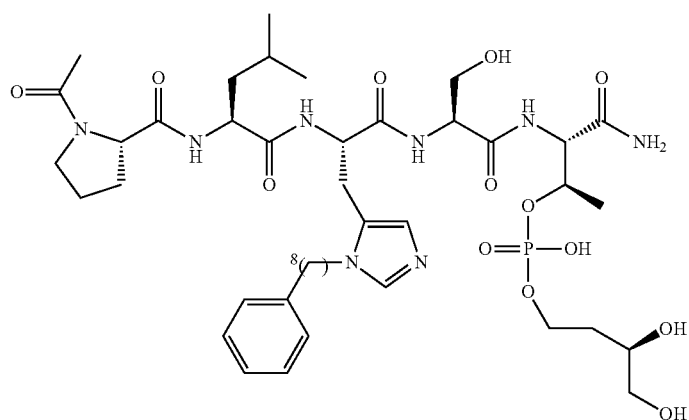
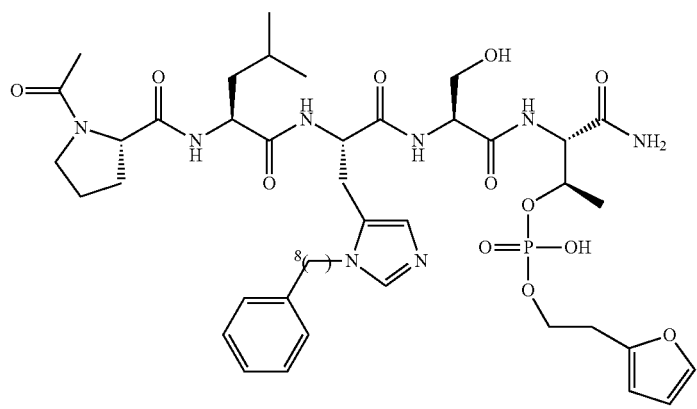
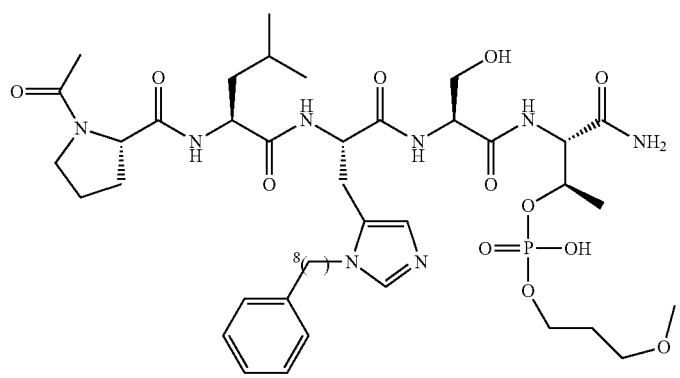

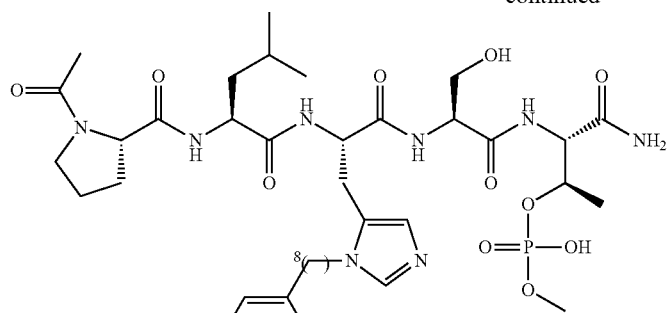
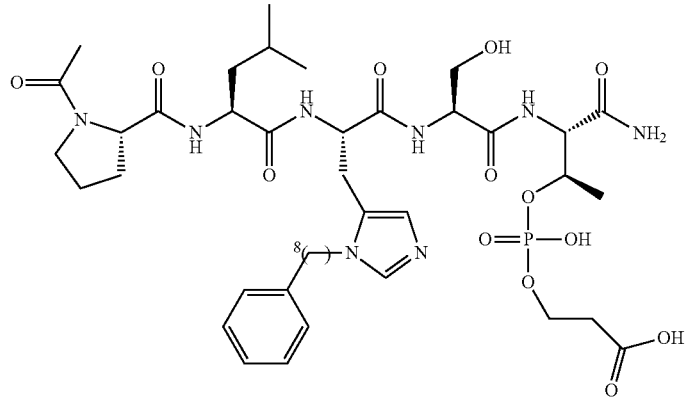
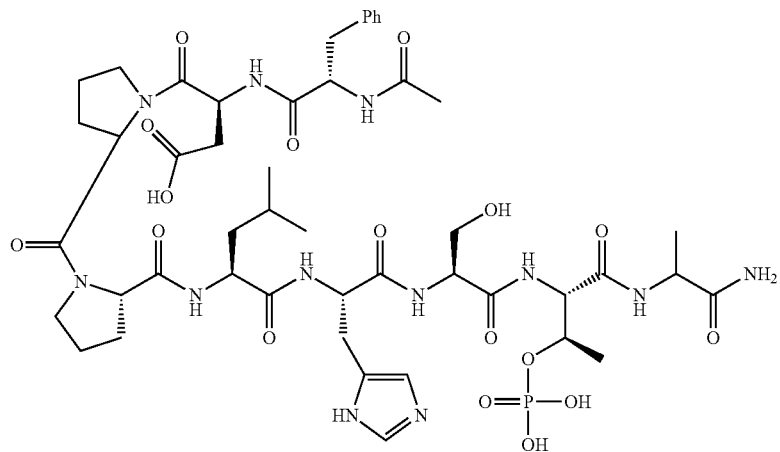
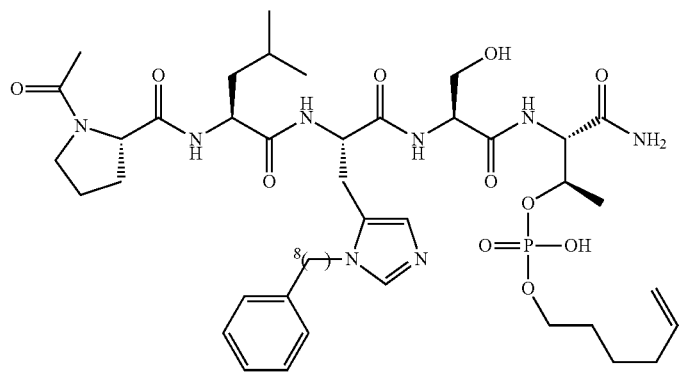

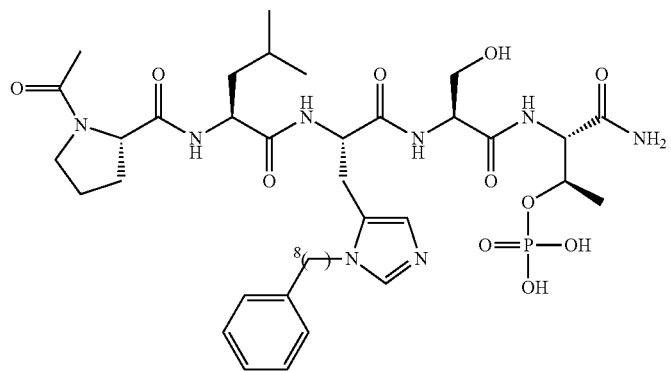
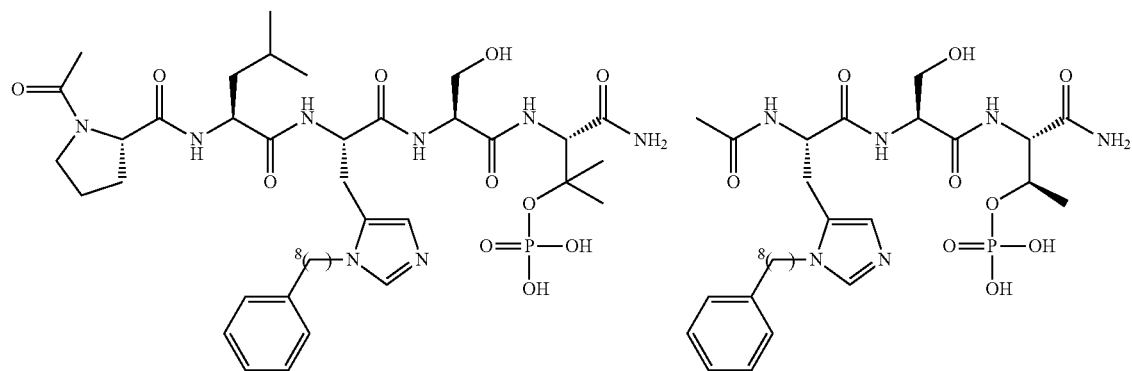
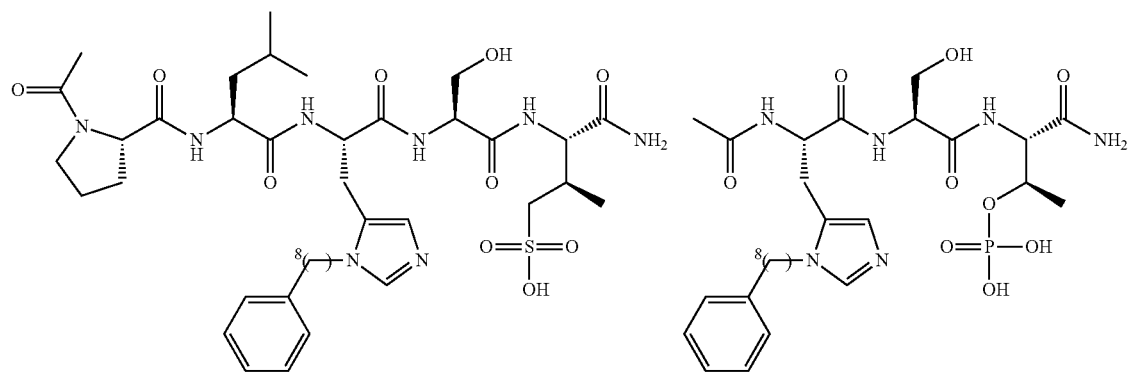
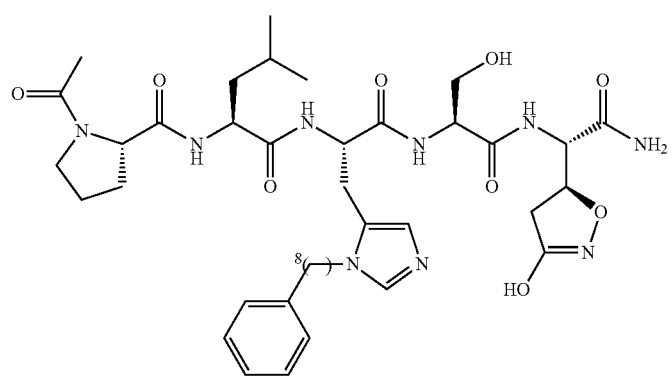

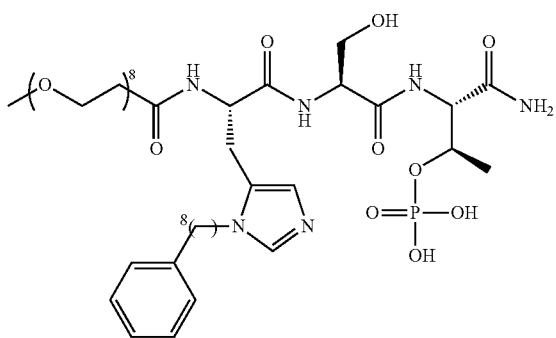
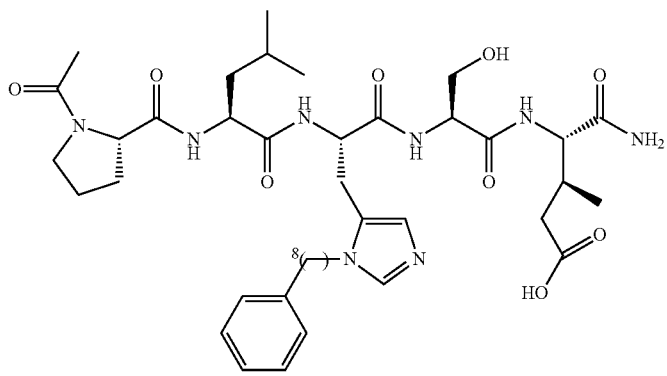
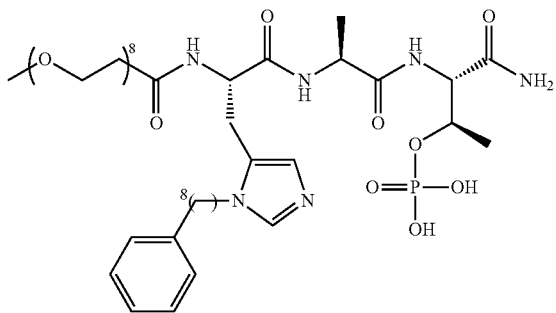
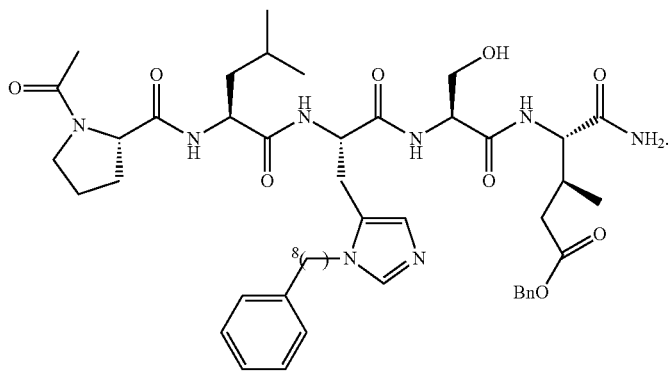

In certain embodiments, the compound is not a compound represented by any of the following structures:
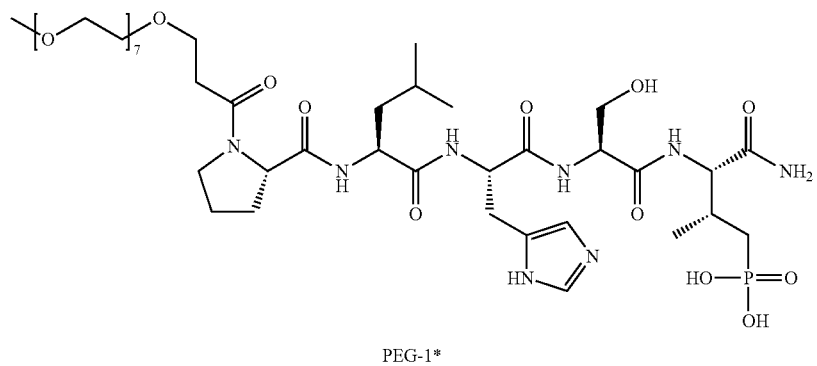
PEG-1*
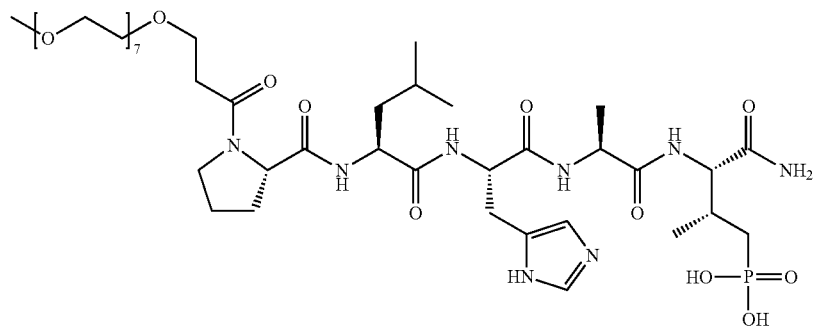
PEG-1*(S/A)
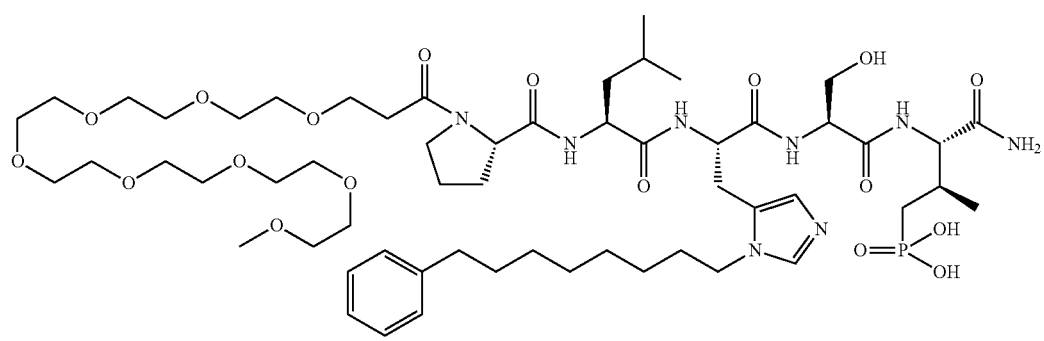
PEG-4j*
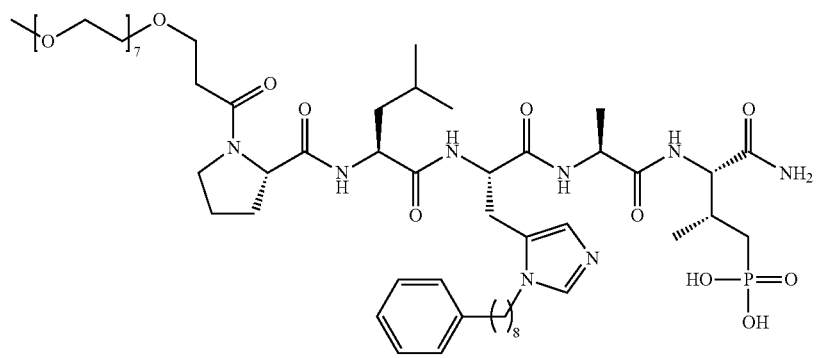
PEG-4j*(S/A)

-continued
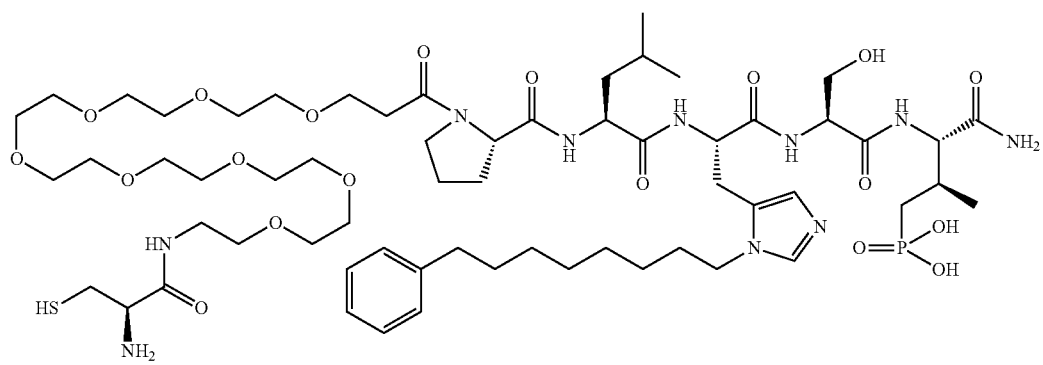
Cys-PEG-4j*
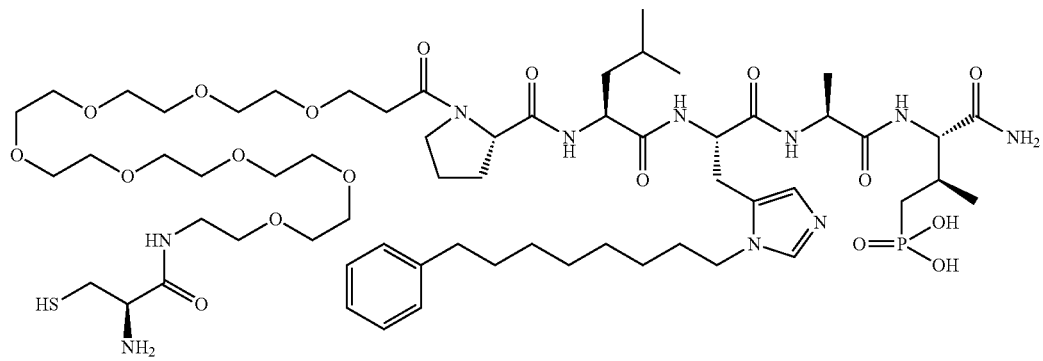
Cys-PEG-4j*(S/A)
TABLE 4
| | | Expected ESI (M + H)+ | Observed ESI (M + H)+ |
|---|---|---|---|
| Cys-PEG-4j* (S/A) | | 1329.7 | 1329.6 |
| PEG-1* (S/A) | | 1009.5 | 1009.2 |

TABLE 4-continued
| | | Expected ESI (M + H)+ | Observed ESI (M + H)+ |
|---|---|---|---|
| PEG-4j* (S/A) | 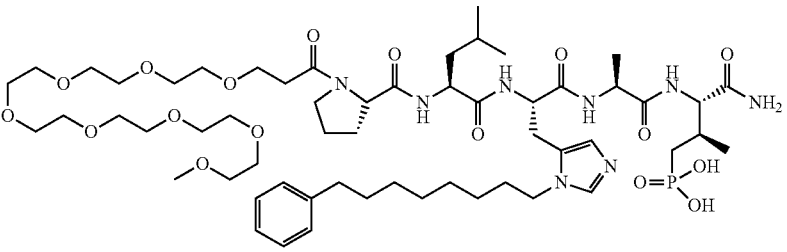 | 1197.7 | 1197.4 |
| d-1 | 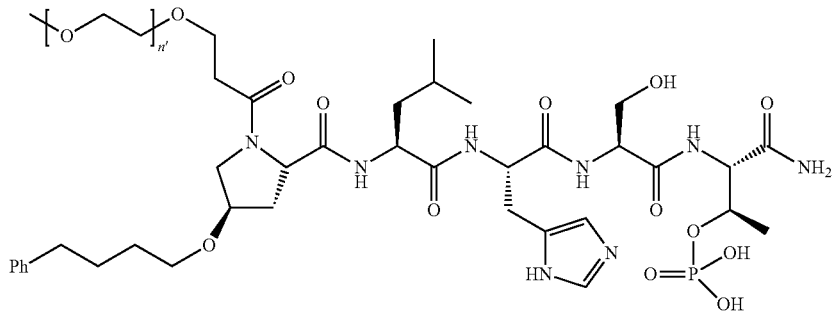 d-1 n' is an integer from 5-8 | | |
| d-1A | 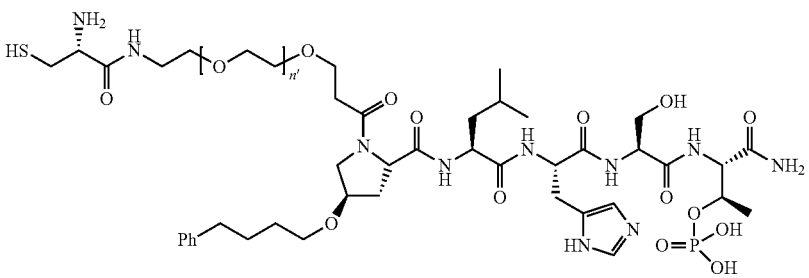 d-1A n' is an integer from 5-8 | | |
| d-2 | 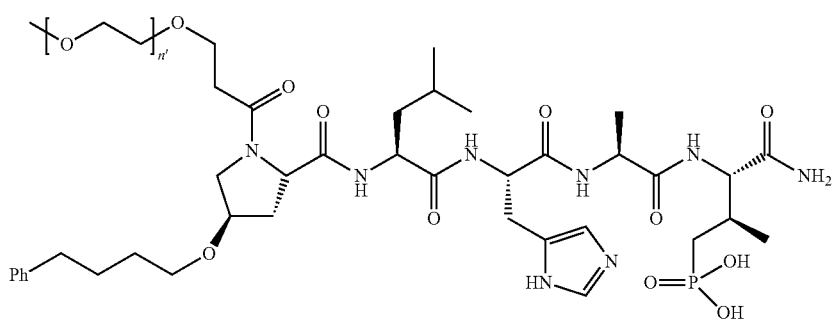 d-2 n' is an integer from 5-8 | | |

TABLE 4-continued
|  | Expected ESI (M + H)+ | Observed ESI (M + H)+ |
|---|---|---|
d-2A
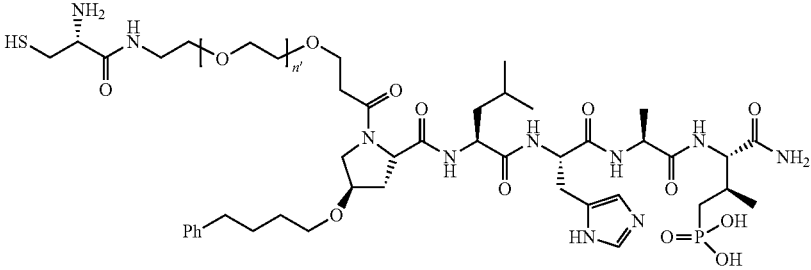
d-2A
n' is an integer from 5-8
d-3
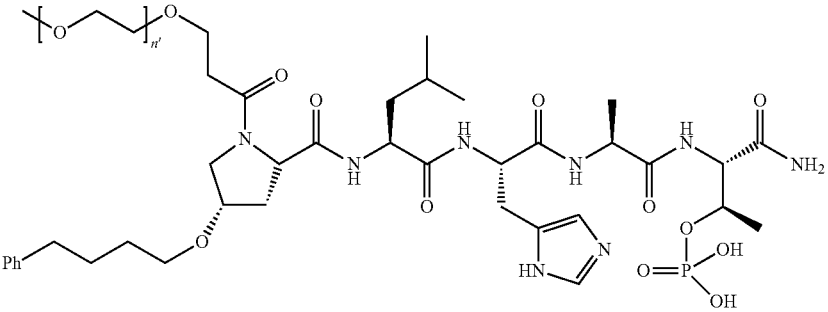
d-3
n' is an integer from 5-8
d-3A
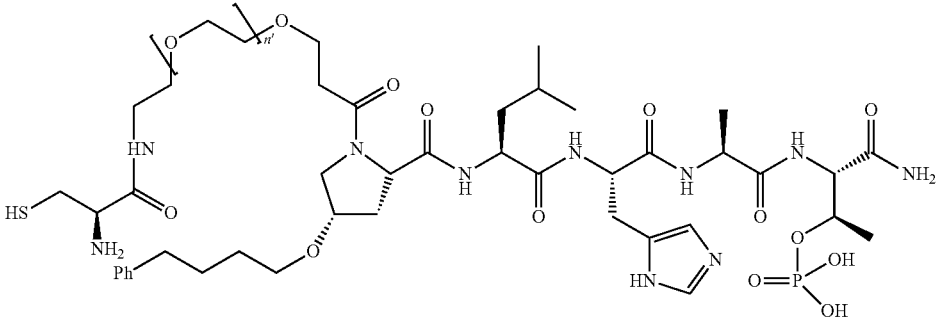
d-3A
n' is an integer from 5-8
4j
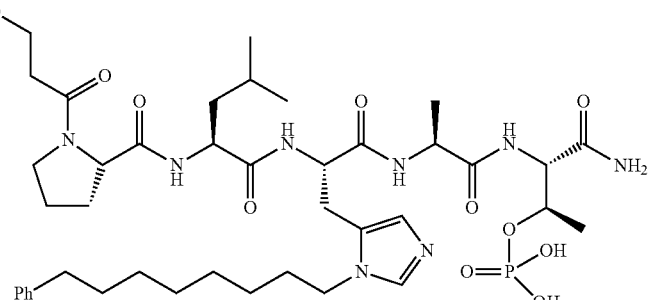
4j
n' is an integer from 5-8

TABLE 4-continued

|  | Expected ESI (M + H)+ | Observed ESI (M + H)+ |
|---|---|---|

4j-A

*[structure of compound 4j-A]*

4j-A
n' is an integer from 5-8

3j

*[structure of compound 3j]*

3j
n' is an integer from 5-8

3j-A

*[structure of compound 3j-A]*

3j-A
n' is an integer from 5-8

In another aspect, the invention relates to a pharmaceutical composition comprising any compound of the invention in a pharmaceutically acceptable carrier.

In another aspect, the invention provides a method for the prevention, amelioration, or treatment of a subject for a hyperproliferative disorder comprising administration of a composition comprising any of the compounds according to the invention.

In certain embodiments, the method further includes identification of a subject suffering from or suspected of suffering from a hyperproliferative disorder.

In certain embodiments, the method further comprises monitoring the subject for prevention, amelioration, or treatment of a hyperproliferative disorder. In certain embodiments, the hyperproliferative disorder comprises cancer. In certain embodiments, the cancer is selected from the group consisting of Acute Lymphoblastic Leukemia, Acute Myeloid Leukemia, Adrenocortical Carcinoma, Basal Cell Carcinoma, Bladder Cancer, Bone Cancer, Brain Tumor, Breast Cancer, Cervical Cancer, Chronic Lymphocytic Leukemia, Chronic Myelogenous Leukemia, Chronic Myeloproliferative Disorders, Colon Cancer, Colorectal Cancer, Cutaneous T-Cell Lymphoma, Esophageal Cancer, Ewing Family of Tumors, Retinoblastoma, Gastric (Stomach) Cancer, Gastrointestinal Tumors, Glioma, Head and Neck Cancer, Hepatocellular (Liver) Cancer, Hodgkin Lymphoma, Islet Cell Tumors (Endocrine Pancreas), Kidney (Renal Cell) Cancer, Laryngeal Cancer, Non-Small Cell Lung Cancer, Small Cell Lung Cancer, Lymphoma, Medulloblastoma, Melanoma, Pancreatic Cancer, Prostate Cancer, Renal Cancer, Rectal Cancer, and Thyroid Cancer.

In another aspect, the invention provides a kit comprising at least one compound of the invention and instructions for use.

In certain aspect, the invention provides a chemical library including two or more compounds of the invention.

In another embodiment, the invention provides a method for the preparation of peptide derivatives comprising using a pivaloyloxymethyl ("POM")-protected amino acid analogue as an intermediate or a building block, wherein said amino acid analogue is pThr, pSer, or Pmab, or a salt, solvate, hydrate, or stereoisomer thereof, and wherein said amino acid analogue is further optionally protected by one or more protecting groups that are same or different from POM.

In certain embodiments, wherein the POM-protected amino acid analogue is a mono- or di-POM-protected pThr or Pmab, and said POM-protected amino acid analogue is further optionally protected by a protecting group that is different from POM.

In certain embodiments, the POM-protected amino acid analogue is

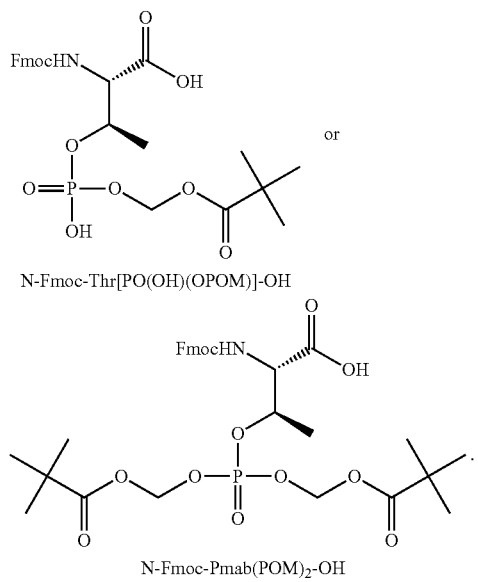

N-Fmoc-Thr[PO(OH)(OPOM)]-OH

N-Fmoc-Pmab(POM)$_2$-OH

In certain aspects, the invention relates to a peptide derivative prepared from any method described herein, including the methods described and shown in Schemes 1-9.

The invention also provides an isotopically labeled compound of any of the formulae delineated herein. Such compounds have one or more isotope atoms which may or may not be radioactive (e.g., $^3$H, $^2$H, 14C, $^{13}$C, $^{35}$S, $^{32}$P, $^{125}$I, and $^{131}$I) introduced into the compound. Such compounds are useful for drug metabolism studies and diagnostics, as well as therapeutic applications.

The structures of the compounds of the invention may include asymmetric carbon atoms. Accordingly, the isomers arising from such asymmetry (e.g., racemates, racemic mixtures, single enantiomers, individual diastereomers, diastereomeric mixtures) are included within the scope of this invention, unless indicated otherwise. Other stereoisomeric forms may be defined, in terms of absolute stereochemistry, as (R)- or (S)-, or as (D)- or (L)- for amino acids.

Such isomers can be obtained in substantially pure form by classical separation techniques and/or by stereochemically controlled synthesis. For example, optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products).

In addition, some of the compounds of this invention may have one or more double or triple bonds. Such compounds can occur as cis- or trans- or E- or Z— double isomeric forms, which are included within the scope of this invention. Further, the configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

All crystal forms of the compounds described herein are also expressly included in the present invention.

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example, a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Prodrug derivatives of the compounds of the invention can be prepared by methods known to those of ordinary skill in the art (e.g., for further details see Saulnier et al., (1994), *Bioorganic and Medicinal Chemistry Letters*, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Design of the Compounds of the Invention

The invention also provides methods of design and/or synthesis of a novel class of compounds that act as kinase-directed inhibitors. It is contemplated that these compounds down-regulate Plk1 function and Plk1 PBD-binding antagonists and may serve as anticancer agents. The invention also provides methods of use thereof. In certain embodiments, the compounds of the invention are uncharged prodrug-protected peptides that combine high affinity mono-esters with bio-cleavable protecting groups (e.g., pivaloyloxymethyl: "POM"). In certain embodiments, the compounds of the invention achieve enhanced efficacy in cellular studies.

The polo-like kinase 1 (Plk1) represents a new target for anticancer therapeutic development. Plk1 contains a C-terminal polo-box domain (PBD) that recognizes phospho-Ser (pSer)/phospho-Thr (pThr)-containing motifs, which recruits Plk1 to specific sub-cellular sites. This event is critical for proper Plk1 function.

Over-expression of Plk1 induces neoplastic transformation of human cells, whereas interference with Plk1 function induces apoptosis in tumor cells but not in normal cells. Moreover, Plk1 over-expression is associated with aggressive disease stage and poor patient survival in various types of cancers (Elia et al., *Modular Protein Domains*, 2005, 163-179). Over the years, efforts have been made to generate anti-Plk1 inhibitors, resulting in several compounds (BI 2536, GSK Compound 1, Cyclapolin 1, DAP81, and TAL) developed to competitively inhibit the kinase activity or substrate recognition of Plk1 (Strebhardt, K. et al., Nat. Rev. Cancer 6, 321-330. (2006)). However, largely because of the structural similarities among the catalytic domains of all Plks and other related kinases, it has been difficult to generate Plk1-specific inhibitors. Thus, since the non-catalytic PBD is found only in the members of the Plk subfamily, development of novel inhibitors that target the PBD of Plk1 may prove to be an alternative strategy for selectively targeting Plk1.

While conducting studies on the interaction between Plk1 and its physiological binding target PBIP1, a minimal phosphopeptide derived from the Thr78 region of PBIP1 was identified that exhibits a high level of affinity and specificity for the Plk1 PBD. Testing of a non-hydrolyzable p-T78 mimetic peptide demonstrated that inhibition of the Plk1 PBD function results in a chromosome congression defect that leads to mitotic arrest and apoptotic cell death, as observed previously in cells expressing a dominant-negative PBD (Seong, Y. S. et al. J. Biol. Chem. 277, 32282-32293 (2002); & Hanisch, A. et al., Mol. Biol. Cell 17, 448-459 (2006)). Since interference with Plk1 function induces apoptosis in most tumor cells but not in normal cells, these findings demonstrate that inhibition of the PBD function is sufficient to interfere with cell proliferation activity of tumor cells. Furthermore, data presented here directly provide the proof-of-principle that specific inhibition of Plk1 PBD is achievable by a small mimetic peptide or its relevant compounds.

It has been demonstrated that SpT-dependent electrostatic interactions with His538 and Lys540 residues are critical for the interaction between optimal peptides (PMQSpTPL and MQSpTPL) and the Plk1 PBD12,13. Comparative in vitro binding studies and analyses of the phosphopeptide-binding pockets of PBDS+G and PBDS with PBDPL, PBDPP, and PBDLH revealed that, in addition to the SpT motif of the phosphopeptide that acts as a high affinity anchor, the N-terminal residues provide additional binding affinity and specificity to the Plk1 PBD through three distinct interactions. First, the polar contact between the carbonyl oxygen N-terminal to the Leu-3 of PLHSpT or LHSpTA and the guanidinium moiety of Arg516 of Plk1 PBD provides a molecular basis for a high affinity and specificity interaction. Second, docking of the N-terminal Pro-4 side chain into the pocket generated by the surrounding Trp414 and Phe535 offers additional affinity and likely another level of specificity to the interaction. Notably, the PBDs from both Plk2 and Plk3 possess Lys and Tyr residues at positions analogous to the Plk1 Arg516 and Phe535 residues, respectively, in Plk1, and, as a consequence, may fail to generate as favorable an environment to accommodate the N-terminal Pro residue. Third, peptide pull-down assays demonstrate that the His-2 residue adds another layer of Plk1 PBD specificity.

Besides each amino acid residue of the p-T78 peptide involved in defining the Plk1 binding affinity and specificity, the positions of the phosphopeptide and glycerol in the pocket, along with the network of water molecules that mediate contacts between the phosphopeptide and the PBD, suggest that both the glycerol and the network of water molecules surrounding the phosphopeptide could be important elements of the PBD recognition by phosphopeptides. Furthermore, the structures of the $PBD^{S+G}$, $PBD^S$, and $PBD^{PL}$ were remarkably similar, hinting that the other glycerol molecule and the sulfate anion occupying the phosphopeptide-binding cleft may substitute the role of the SpT dipeptide.

The collected data demonstrate that the Plk1 PBD-binding pocket accommodates (i) the core SpT motif, (ii) the N-terminal hydrophobic residue, (iii) glycerol, and (iv) a network of contacting water molecules. A combination of some or all of these four elements could be potentially used for targeted drug design. Better understanding of the PBD interaction as well as further isolation and development of PBD-binding agents would greatly facilitate the discovery of a new class of Plk1-specific anti-cancer therapeutic agents.

To unambiguously identify the site of the histidine alkylation and to understand the basis for the high binding affinity of Compound 4j:

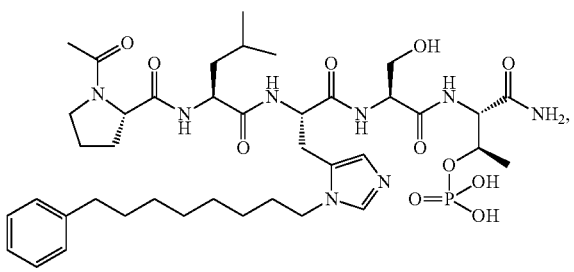 [SMILES: CC(=O)N1CCC[C@H]1C(=O)N[C@@H](CC(C)C)C(=O)N[C@@H](Cc1cncn1CCCCCCCCc1ccccc1)C(=O)N[C@@H](CO)C(=O)N[C@H](C(N)=O)[C@@H](C)OP(=O)(O)O]

the co-crystal structure of Plk1 PBD in complex with Compound 4j was solved. This structure confirmed the earlier tandem MS results, showing that alkylation had occurred on the histidine residue. It also showed that the $C_6H_5(CH_2)_8$— group was attached to the $\delta^1$ nitrogen (N3) on the imidazole ring.

The inventors have recently discovered high affinity peptide-based Plk1 PBD-binding antagonists (see, e.g., those disclosed in WO2012/142245 A2 and US 2012/0065146 A). However, despite high PBD-binding affinities, some of the compounds exhibit unacceptably poor bioavailability in whole cell studies, due to the di-anionic charge of their phosphoryl functionalities. It is believed that a significant factor contributing to low bioavailability arise from poor membrane transport, which may be due in part to the di-anionic charge of the phosphoryl group.

The inventors have made efforts to design and synthesize low nanomolar-affinity bioavailable Plk1 PBD binding inhibitors with reduced anionic charge. The "charge problem" was partially overcome in WO2012142245 A2, in which the parent dianionic phosphoryl moieties contained in peptides containing an "alkyl-His" residue are converted to singly charged mono-esters. As used herein, the "alkyl-His" refers to a histidine residue having a long-chain alkyl-phenyl group attached to the N3 position of the imidazole side chain. The effects of minimizing phosphoryl charge were examined within the context of alkyl-His-containing platform.

In certain embodiments, the inventors appended a POM group to one pThr phosphoryl hydroxyl and introduced a cationic bis-alkyl His residue. This neutralized the net charge of the peptide (no net positive or negative charge). These compounds are able to achieve greater levels of mitotic block than the di-anionic species. This suggests better cellular uptake.

The invention provides the design, synthesis and biological evaluation of anticancer therapeutics, which act through down-regulation of oncogenic Plk1 through spatial disregulation achieved by blocking the function of its PBD. Specifically, the invention provides uncharged prodrug-protected peptides that combine high affinity bio-cleavable protecting group (e.g., pivaloyloxymethyl; POM) with cationic bis-alkyl His residues. It has been observed that the compounds of the invention achieve enhanced efficacy in cellular studies.

Compositions, Methods, and Kits

The invention provides compositions including any of the compounds of the invention in a pharmaceutically acceptable carrier, for use, for example, for the preparation of a medicament. The medicament can be, for example, a medicament for the prevention, amelioration, or treatment of a hyperproliferative disorder such as cancer.

In still other embodiments, such compositions are labeled for the treatment of a hyperproliferative disorder such as cancer. In a further embodiment, the effective amount is effective to treat or prevent a hyperproliferative disorder such as cancer in a subject, as described herein.

In certain embodiments, the hyperproliferative disorder is cancer. Cancers can be characterized as solid tumors and non-solid tumors. Cancers include, but are not limited to Acute Lymphoblastic Leukemia, Acute Myeloid Leukemia, Adrenocortical Carcinoma, Basal Cell Carcinoma, Bladder Cancer, Bone Cancer, Brain Tumor, Breast Cancer, Cervical Cancer, Chronic Lymphocytic Leukemia, Chronic Myelogenous Leukemia, Chronic Myeloproliferative Disorders, Colon Cancer, Colorectal Cancer, Cutaneous T-Cell Lymphoma, Esophageal Cancer, Ewing Family of Tumors, Retinoblastoma, Gastric (Stomach) Cancer, Gastrointestinal Tumors, Glioma, Head and Neck Cancer, Hepatocellular (Liver) Cancer, Hodgkin Lymphoma, Islet Cell Tumors (Endocrine Pancreas), Kidney (Renal Cell) Cancer, Laryngeal Cancer, Non-small Cell Lung Cancer, Small Cell Lung Cancer, Lymphoma, Medulloblastoma, Melanoma, Pancreatic Cancer, Prostate Cancer, Renal Cancer, Rectal cancer, Thyroid Cancer.

The compounds of the invention can also be used in methods for the prevention, amelioration, or treatment of a subject for acquired immunodeficiency syndrome (AIDS). In certain embodiments, the compounds of the invention can be tagged with a HIV Tat-sequence for inhibition of HIV budding.

In an embodiment, the compound is administered to the subject using a pharmaceutically-acceptable formulation. In certain embodiments, these pharmaceutical compositions are suitable for oral or parenteral administration to a subject. In still other embodiments, as described in detail below, the pharmaceutical compositions of the present invention may be specially formulated for administration in solid or liquid form, including those adapted for the following: (1) oral administration, for example, drenches (aqueous or nonaqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound. In certain embodiments, the subject is a mammal, e.g., a primate, e.g., a human.

The methods of the invention further include administering to a subject a therapeutically effective amount of a compound in combination with a pharmaceutically acceptable excipient. The phrase "pharmaceutically acceptable" refers to those compounds of the invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable excipient" includes pharmaceutically-acceptable material, composition or vehicle, such as a liquid or solid filler, diluent, carrier, solvent or encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these compositions include the step of bringing into association a compound(s) with the carrier and, optionally, one or more accessory ingredients. In general, the formulations are prepared by uniformly and intimately bringing into association a compound with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants, such as wetting agents, emulsifying and suspending agents, sweetening, flavoring, coloring, perfuming and preservative agents.

Suspensions, in addition to the active compound(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound(s) include powders, sprays, ointments, pastes, creams, lotions, gels, solutions, patches and inhalants. The active compound(s) may be mixed under sterile conditions with a pharmaceutically-acceptable carrier, and with any preservatives, buffers, or propellants which may be required.

The ointments, pastes, creams and gels may contain, in addition to compound(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound(s), excipients, such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids, such as glycine, buffers, salts, sugars or sugar alcohols. Aerosols generally are prepared from isotonic solutions.

Transdermal patches have the added advantage of providing controlled delivery of a compound(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compound(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound(s) in biodegradable polymers, such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compound(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic to the patient. An exemplary dose range is from about 0.1 µg to 20 milligram per kilogram of body weight per day (mg/kg/day) (e.g., 0.1 µg/kg to 2 mg/kg, 0.3-3 µg/kg, 0.18-0.54 mg/kg). In other embodiments, the amount varies from about 0.1 mg/kg/day to about 100 mg/kg/day. In still other embodiments, the amount varies from about 0.001 µg to about 100 µg/kg (e.g., of body weight). Ranges intermediate to the above-recited values are also intended to be part of the invention.

The invention also provides methods including identification of a subject suffering from or suspected of suffering from a hyperproliferative disorder and/or monitoring the subject for prevention, amelioration, or treatment of a hyperproliferative disorder.

The invention provides kits for the treatment or prevention of a hyperproliferative disorder such as cancer. The kits contain at least one compound of the inventions and instructions for use. In one embodiment, the kit includes a therapeutic or prophylactic composition containing an effective amount of a compound of the invention in unit dosage form. The invention also provides kits having 2, 3, 4, 5, 6, 7, 8, 9, or 10 compounds of the invention.

As used herein, "kits" are generally understood to contain at least the non-standard laboratory reagents for use in the methods of the invention. For example, a kit can include at least one of, preferably at least two of at least one peptide for modification, one or more aldehyde molecules for modification of peptides, and instructions for use, all in appropriate packaging. The kit can further include any other components required to practice the method of the invention, as dry powders, concentrated solutions, or ready to use solutions. In some embodiments, the kit comprises one or more containers that contain reagents for use in the methods of the invention; such containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

In some embodiments, a compound of the invention is provided in combination with a conventional therapeutic agent. In other embodiments, the kit comprises a sterile container which contains a therapeutic or prophylactic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired a compound of the invention is provided together with instructions for administering the compound to a subject having or at risk of developing neoplasia. The instructions will generally include information about the use of the composition for the treatment or prevention of neoplasia. In other embodiments, the instructions include at least one of the following: description of the therapeutic agent; dosage schedule and administration for treatment or prevention of ischemia or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The invention further provides libraries including at least two compounds of the invention. "Library" as used herein is understood to be a chemical library. Chemical libraries include two or more compounds (10 or more, 50 or more, 100 or more, 200 or more, 500 or more, 1000 or more, 5000 or more, 10,000 or more, etc.; or any range bracketed by the noted values), preferably that have structural and/or potential functional properties. Libraries can be used, for example for screening assays to select compounds with desired activities, e.g., kinase binding, kinase stimulating, kinase inhibiting activity.

Any compositions or methods provided herein can be combined with one or more of any of the other compositions and methods provided herein.

Design and Synthesis of POM-Protected Amino Acid Analogues and Peptide Derivatives Protein phosphorylation is a fundamental form of post-translational modification that affects approximately one third of all proteins. The presence of phosphothreonine (pThr), phosphoserine (pSer) and phosphotyrosine (pTyr) containing sequences can introduce unigue recognition features, which often facilitate specific protein-protein interactions (PPIs). Synthetic phosphopeptides modeled on recognition sequences can serve as useful pharmacological tools for studying these PPIs. However, in cellular systems the bioavailability of phosphopeptides may be limited by the enzymatic lability of the phosphoryl ester bond and poor membrane transport of the phosphoryl di-anionic species. While replacement of the phosphoryl ester oxygen by methylene or fluoromethylenes has addressed issues related to enzymatic stability for pTyr, pSer and pThr, bioavailability can still be limited by the di-anionic charge of the resulting phosphonic acids.

A general strategy for increasing the bioavailability of phosphates and phosphonates is to mask their acidic functionality with "prodrug" groups that can be removed enzymatically once the agent is within the cell. In this regard, POM protection is known to have been used in a variety of phosphoryl species, including nucleotides.

The present inventors have designed and/or synthesized amino acid analogues that contain mono-ester POM residues as well as bis-POM esters. In certain embodiments, the amino acid analogues include, for example, pThr and Pmab-containing peptides with their phosphoryl groups in POM-protected ester forms combined with a cationic bis-alkyl His residue that renders the total peptide charge as neutral. Esterase cleavage of the first POM group would liberate the bioactivebis-alkyl His containing peptide.

The invention thus provides a novel class of POM-protected amino acid analogues, or a salt, solvate, hydrate, or stereoisomer thereof. In certain embodiments, the POM-protected amino acid analogue of the invention is a POM-protected pThr, pSer, or Pmab residue, which is further optionally protected by one or more additional protecting groups that are same or different from POM.

For example, the POM-protected amino acid analogues of the invention include the following:

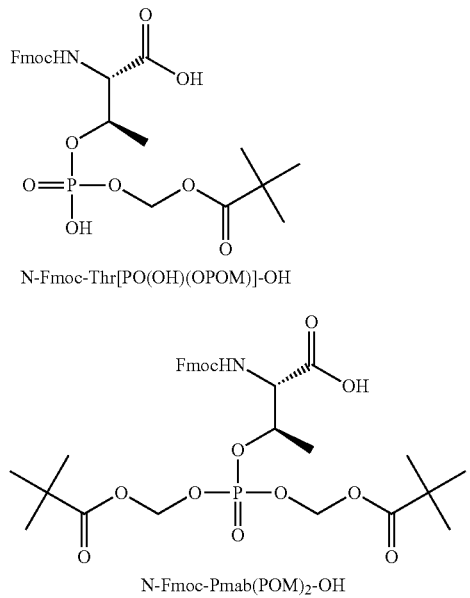

1

N-Fmoc-Thr[PO(OH)(OPOM)]-OH

2

N-Fmoc-Pmab(POM)$_2$-OH

Design and Use of POM-Protected Amino Acid Analogues of the Invention:

Solid-phase synthesis of pTyr-containing peptides can be achieved in the absence of phosphoryl protection using N-Fmoc-Tyr(PO$_3$H$_2$)—OH (Ottinger et al. 1993, 32, 4354-4361). It was contemplated that one potential route to the synthesis of Thr(PO$_3$POM$_2$)-containing peptides could involve using N-Fmoc-Thr(P O$_3$H$_2$)—OH, which would result in resin-bound peptides bearing full side chain protection except for a free pThr phosphoryl group. In this methodology, in situ introduction of phosphoryl POM-protection would be done immediately prior to cleavage of the peptide from the resin. Although an initial coupling of unprotected N-Fmoc-Thr(PO$_3$H$_2$)—OH occurred cleanly, further peptide synthesis through the introduction of additional amino acid residues followed by resin cleavage, lead to very low yields of isolated pThr-containing peptides. This indicated that peptide chain elongation in the presence of unprotected Thr(PO$_3$H$_2$) was problematic.

In further studies, it was observed that treatment of resin-bound N-Fmoc-Thr(PO$_3$H$_2$) with excess pivaloyloxymethyl iodide (POM-I) and diisopropylethylamine (DIEA) followed by resin cleavage (1% TFA in CH$_2$Cl$_2$) cleanly provided N-Fmoc-Thr(PO$_3$POM$_2$)-amide. This demonstrated both the ability to perform on-resin POM-protection of the phosphoryl group and the stability of the resulting Thr(PO$_3$POM$_2$) residue to the conditions of resin cleavage. However, piperidine-mediated Fmoc-deprotection of resin-bound N-FmocThr(PO$_3$POM$_2$) followed by 1% TFA resin cleavage gave the Thr[PO(OH)(OPOM)] containing peptide, indicating that mono-POM deprotection had occurred in the presence of piperidine.

This is consistent with the reported ability of piperidine to selectively cleave a single POM group from the triester PO(OPOM)$_3$ to yield PO(OH)(POM)$_2$ (Hwang et al. Org. Lett. 2004, 6, 1555). The instability of pThr phosphoryl bis-esters to piperidine treatment is one reason why solid-phase peptide incorporation of pThr and pSer residues on acid-labile resin is normally done using commercially-available N-Fmoc derivatives bearing mono-benzyl-protection of the phosphoryl group [N-Fmoc-Thr[PO(OH)(OBn)]—OH and N-Fmoc-Ser[PO(OH)(OBn)]—OH, respectively) (McMurray et al., Biopolymers 2001, 60, 3-31; Attard et al., Int. J. Pept. Res. Ther., 2007, 13, 447; and Toth et al. Curr. Org. Chem. 2007, 11, 409).

In order to demonstrate the applicability of N-Fmoc-Thr [PO(OH)(OPOM)]—OH (1) for the synthesis of Thr (PO$_3$POM$_2$)-containing peptides, the present inventors chose as a target the pentapeptide "PLHSpT", which has been reported as a high affinity ligand of the polo-like kinase 1 (Plk) polo box domain (PBD). The synthesis of Ac-Pro-Leu-His-Ser-Thr[PO(OH)(OPOM)]-amide was accomplished on NovaSyn TG Siber resin using reagent Fmoc-Thr(PO(OH)(OPOM))—OH and standard Fmoc protocols. Following peptide formation and acetylation of the amino-terminal Pro residue, the resin was treated with POMI (10 equivalents) and DIPEA (10 equivalents) in DMF for 4 h. After purification, the two peptides having the correct molecular weight (depending on the mass spectra) were obtained. Tandem MS-MS analyses were performed on these two peptides. The data show that the less polarity one in HPLC is the desire product, another one is the peptide Ac-Pro-Leu-His(N(π)-POM)-Ser-Thr[PO(OH)(OPOM)]-amide.

Based on these results, it was concluded that synthesis of Thr(PO$_3$POM$_2$)-containing peptides could be achieved using N-FmocThr[PO(OH)(OPOM)]—OH as a reagent, with conversion of Thr[PO(OH)(OPOM)] to the desired fully-protected Thr(PO$_3$POM$_2$) form by POM-I/DIEA treatment immediately prior to final resin cleavage. It is also believed that, the late-stage POMylation could alkylate Histidine residue too.

In one aspect, the invention provides a phosphoryl derivatization protocol that eliminates all anionic charge in a peptide. Specifically, the protocol involves bio-reversible protection of the phosphonic moiety. It is believed that the resulting peptide derivatives will retain good efficacy and have enhanced bioavailability.

In another aspect, the invention provides methods for preparing peptide derivatives, wherein a POM-protected amino acid analogue, or a salt, solvate, hydrate, or stereoisomer thereof is used as an intermediate or a building block.

Further, the invention provides peptide derivatives prepared according to the above methods.

The practice of the present invention employs, unless otherwise indicated, conventional techniques that are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology"

"Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). Particularly useful techniques for particular embodiments will be discussed in the sections that follow.

The following non-limiting examples are illustrative of the invention.

I. Synthesis and Chemical Analysis of the Compounds of the Invention

A. Synthesis and Preparation

Compounds of the invention can be synthesized and/or prepared by methods described in this section, the examples, and the chemical literature.

1. General Procedures:

General Methods.

All experiments involving moisture-sensitive compounds were conducted under anhydrous conditions (positive argon pressure) using standard syringe, cannula, and septa apparatus. Fmoc-Ser(Trt)-OH, Fmoc-His(Mtt)-OH and Fmoc-Thr[PO(OH)((OBn)]—OH were purchased from Nova-ChioChem. All solvents were purchased in anhydrous form (Aldrich) and used directly. HPLCgrade hexanes, EtOAc, $CH_2Cl_2$, and MeOH were used in chromatography. Analytical TLCs were performed using Analtech precoated plates (Uniplate, silica gel GHLF, 250 nm) containing a fluorescence indicator. NMR spectra were recorded using a Varian Inova 400 MHz spectrometer. Coupling constants are reported in Hertz, and peak shifts are reported in 5 (ppm) relative to TMS. Low-resolution mass spectra (ESI) were measured with an Agilent 260 1200 LC/MSD-SL system. High resolution mass spectra (HRMS) were obtained by positive ion, ESI analysis on a Thermo Scientific LTQ-XL Orbitrap mass spectrometer with HPLC sample introduction using a short narrow-bore C1s reversed-phase column with CH3CN—H2O gradients. Reported m/z values are the average of eight or more scans over the chromatographic peak of interest.

A) Solid-Phase Peptide Synthesis

Fmoc-Thr(PO(OBzl)OH)—OH and other Fmoc protected amino acids were purchased from Novabiochem. Peptides were synthesized on NovaSyn®TGR resin (Novabiochem, cat. no. 01-64-0060) using standard Fmoc solid-phase protocols in N-Methyl-2-pyrrolidone (NMP). 1-O-Benzotriazole-N,N,N',N'-tetramethyl-uronium-hexafluoro-phosphate (HBTU) (5.0 eq.), hydroxybenzotriazole (HOBT) (5.0 eq.) and N,N-diisopropylethylamine (DIPEA) (10.0 eq.) were used as coupling reagents. Amino terminal acetylation was achieved using 1-acetylimidazole. Finished resins were washed with N,N-dimethylforamide (DMF), methanol, dichloromethane and diethyl ether and then dried under vacuum (overnight). For the synthesis of Pmab-containing peptides, (2S,3R)-4-[di-(tert-butyl)-oxyphosphinyl]-N-Fmoc-L-valine was used in place Fmoc-Thr(PO(OBzl)OH)—OH (Liu, F. et al., Tetrahedron 65, 9673-9679 (2009)).

B) Derivatization on Solid-Phase Using Mitsunobu Reaction Conditions

Crude peptide resins (200 mg, 0.04 mmol) were swelled in dichloromethane (15 minutes) and then treated with triphenylphosphine (262 mg, 1.0 mmol), diethyl azidodicarboxylate (DEAD) (0.46 mL, 40% solution in toluene, 1.0 mol) and alcohols (for example, alcohols a-1; see below) (1.0 mmol) in dry dichloromethane at room temperature (2 h), then washed (dichloromethane), dried under vacuum (2 h) and cleaved by treatment with trifluoroacetic acid.

Alcohols a-1

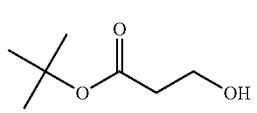

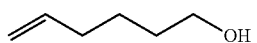

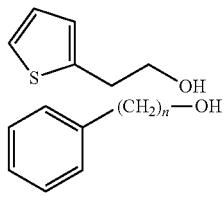

f (n = 4); g (n = 5);
h (n = 6); i (n = 7);
j (n = 8); k (n = 9);
l (n = 10)

C) Peptide Cleavage and Purification

Peptide resins (200 mg) were cleaved by treatment with trifluoroacetic acid:triisbutylsilane:$H_2O$ (90:5:5) (5 mL, 4 h). The resin was removed by filtrations and the filtrate was concentrated under vacuum, then peptide was precipitated by the addition of precipitated with diethyl ether and the precipitate washed with ether. The resulting solid was dissolved in 50% aqueous acetonitrile (5 mL) and purified by reverse phase preparative HPLC using a Phenomenex $C_{18}$ column (21 mm diax250 mm, cat. no: 00G-4436-P0) with a linear gradient from 0% aqueous acetonitrile (0.1% trifluoroacetic acid) to 100% acetonitrile (0.1% trifluoroacetic acid) over 30 minutes at a flow rate of 10.0 mL/minute. Lyophilization gave the products as white powders.

D) X-Ray Crystallography

Protein Purification and Crystallization.

Plk1 PBD protein (residues 371-603) was purified as previously described (Yun, S.-M. et al. Nat. Struct. Mol. Biol. 16, 876-882 (2009)). Crystals were grown using the hanging drop vapor diffusion method. PBD protein at 12 mg/mL in 10 mM Tris pH 8, 0.5 M NaCl, 10 mM DTT, 2% DMSO and 2 mM compound peptide 4j was mixed with an equal volume of reservoir solution consisting of 15% (w/v) PEG 3350, 0.1 M glycine pH 9, and 300 mM NaCl. Crystals appeared overnight and reached maximum size over several days.

Data Collection, and Structure Determination and Refinement.

Crystals were cryo-protected in 33.3% (w/v) PEG 3350, 500 mM NaCl, 0.1 M glycine pH 9, 2 mM peptide 4j, 2% DMSO and 10 mM DTT, and data were collected at 100 K on a Mar345 image plate detector with a Rigaku RU-300 home X-ray source. The data were processed with the HKL (Minor, W. et al. Acta Crystallogr. D Biol. Crystallogr. 62, 859-66 (2006)) and CCP4 software suites (*Acta Crystallogr. D Biol. Crystallogr.* 50, 760-3 (1994)). The structure was solved by molecular replacement using AmoRe (Navaza, J. *Acta Crystallogr. D Biol. Crystallogr.* 57, 1367-72 (2001)) using chain A of structure 3FVH (Yun, S.-M. et al. *Nat. Struct. Mol. Biol.* 16, 876-882 (2009)). (RCSB accession code) as a search model, and refined using PHENIX (Adams, P. D. et al. *Acta Crystallogr. D Biol. Crystallogr.* 66, 213-21) with manual fitting in XtalView (McRee, D. E. *J. Struct. Biol.* 125, 156-65 (1999)). The figure was created using Molscript (Kraulis, P. J. *J. Appl. Crystallogr.* 24, 946-950 (1991)) and PyMOL.

SUPPLEMENTARY TABLE 1

Data Collection and Refinement Statistics

| | |
|---|---|
| PDB ID | 3RQ7 |
| Space group | $P2_1$ |
| a (Å) | 35.3 |
| b (Å) | 51.2 |
| c (Å) | 58.0 |
| β | 101.0° |
| Resolution range (Å) | 15-1.55 |
| Average redundancy | 6.2 |
| Completeness[a] | 99.8% (98.3%) |
| $R_{sym}$[a] | 4.8 (19.7) |
| Average I/σ[a] | 31.7 (4.2) |
| $R/R_{free}$ (%) | 15.1/18.3 |

[a]Values for the highest resolution shell are shown in parentheses.

2. Synthetic Schemes and Example

1) Synthesis of N-Fmoc-Thr[PO(OH)(OPOM)]—OH

Scheme 1.

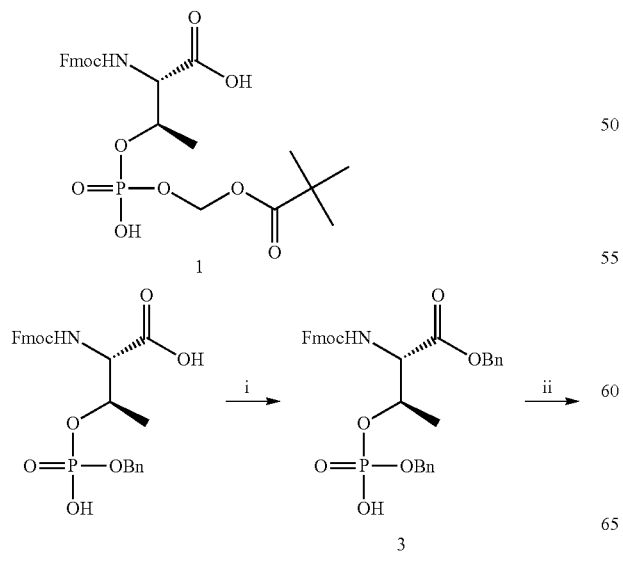

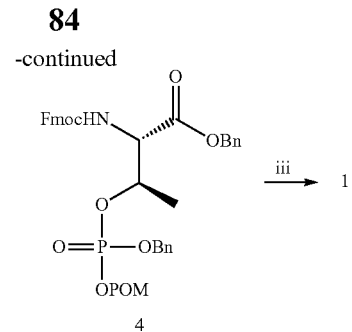

Reagents and conditions: (i) BnOH (1.5 equiv), DMAP (1.0 equiv), EDCI (2.5 equiv), $CH_2Cl_2$, 0° C. to rt, 2 h, 70% yield; (ii) iodomethylpivalate (2.0 equiv), DIPEA (2.0 equiv), DMF, rt, 12 h, 60% yield; (iii) 10% Pd•C, MeOH, rt, 1 h, 68% yield.

Scheme 1:

Benzyl esterification of the carboxylic acid of commercially available N-Fmoc-Thr[PO(OH)(OBn)]—OH was achieved by treatment with benzyl alcohol and 1-(3-dimethylaminopropyl)-3-ethylcarbodiimide hydrochloride (EDCI) in the presence of DMAP. Reaction of the resulting N-Fmoc-Thr[PO(OH)(OBn)]-OBn (3) with excess POMI and DIPEA resulted in esterification of the free phosphoryl hydroxyl to yield N-Fmoc-Thr[PO(OBn)(OPOM)]-OBn (4) as a 1:1 mixture of phosphoryl diastereomers. Subsequent hydrogenolytic cleavage of all benzyl groups cleanly yielded the desired reagent, N-Fmoc-Thr[PO(OH)(OPOM)]—OH (1).

N-[(9H-Fluoren-9-ylmethoxy)carbonyl]-L-threonine [Phenylmethyl Hydrogen Phosphate (Ester)]Phenylmethyl Ester (3)

Commercially available Fmoc-Thr[PO(OH)((OBn)]—OH (1.0 g, 1.96 mmol), BnOH (0.30 mL, 2.93 mmol), and DMAP (0.24 g, 1.96 mmol) were dissolved in $CH_2Cl_2$ (20 mL) and the mixture were cooled to 0° C. To the cold solution was added EDCI (0.94 g, 4.89 mmol) and the solution was warm to room temperature and stirred (2 h). The reaction was quenched by the addition of aqueous 1N HCl (10 mL) and extracted with $CH_2Cl_2$. The combined organic layer was washed with 1 N HCl and brine, dried ($MgSO_4$), concentrated and the residue was purified by silica gel column chromatography ($CH_2Cl_2$/MeOH from 20/1 to 4/1) to afford 3 as a white semisolid (0.82 g, 70% yield). [a]D 24.8 (c 1.65, $CHCl_3$); $^1H$ NMR (400 MHz, $CDCl_3$) δ 8.81 (brs, 1H), 7.78 (d, J=8.0 Hz, 2H), 7.62 (dd, J1=12.0 Hz, J2=8.0 Hz, 2H), 7.41 (t, J=8.0 Hz, 2H), 7.38-7.27 (m, 12H), 5.91 (d, J=8.0 Hz, 1H), 5.26 (d, J=12.0 Hz, 1H), 5.11-4.94 (m, 4H), 4.54 (d, J=12.0 Hz, 1H), 4.44-4.33 (m, 2H), 4.22 (t, J=8.0 Hz, 1H), 1.38 (d, J=8.0 Hz, 3H); $^{13}C$ NMR (100 MHz, CDCl3) δ 169.7, 156.9, 144.1, 143.7, 141.4, 135.74, 135.68, 135.1, 128.8, 128.7, 128.0, 127.9, 127.3, 125.3, 120.1, 75.6, 69.5, 68.1, 67.6, 58.7, 47.2, 18.7; ESI-HRMS m/z calcd for $C_{33}H_{31}NO_8P$ (M−H)⁻: 600.1787. found: 600.1782.

N-[(9H-Fluoren-9-ylmethoxy)carbonyl]-L-threonine [(2,2-Dimethyl-1 oxopropoxy)methyl Phenylmethyl Phosphate (Ester)]Phenylmethyl Ester (4)

N-[(9H-Fluoren-9-ylmethoxy)carbonyl]-L-threonine [Phenylmethyl Hydrogen Phosphate (Ester)]Phenylmethyl Ester (2) (0.3 g, 0.5 mmol) in DMF (5.0 mL) under argon was treated with DIPEA (0.174 mL, 1.00 mmol) followed by iodomethylpivalate (0.241 g, 1.00 mmol) and the mixture was stirred at room temperature (overnight). The reaction mixture was partitioned ($H_2O$/EtOAc) and the organic layer was washed with H$_2$O and brine, dried (MgSO$_4$), concentrated and the residue was purified by silica gel column chromatography (EtOAc: hexanes from 1/2 to 2/1) to afford 4 as a white semisolid (0.21 g, 60% yield) as a mixture of two diastereomers (ratio 1:1 as determined by $^1$H NMR).

N-[(9H-Fluoren-9-ylmethoxy)carbonyl]-L-threonine [(2,2-Dimethyl-1-oxopropoxy)methyl Hydrogen Phosphate (Ester)][N-FmocThr[PO(OH)(OPOM)]—OH] (1)

A solution of 4 (45 mg, 0.063 mmol) in MeOH (1.25 mL) was hydrogenated over 10% Pd—C (5 mg, 1 h), then filtered and concentrated and the residue was purified by silica gel column chromatography (CH$_2$Cl$_2$/MeOH=10/1 to 4/1) to afford 1 as a colorless oil (23 mg, 68% yield). [a]D 4.98 (c 0.34, MeOH); $^1$H NMR (400 MHz, CD$_3$OD) δ 7.80 (d, J=8.0 Hz, 2H), 7.70 (t, J=8.0 Hz, 2H), 7.39 (t, J=8.0 Hz, 2H), 7.31 (tt, J1=8.0 Hz, J2=4.0 Hz, 2H), 5.58 (d, J=16.0 Hz, 2H), 5.04-4.96 (m, 1H), 4.43-4.35 (m, 3H), 4.26 (t, J=4.0 Hz, 1H), 1.39 (d, J=8.0 Hz, 3H), 1.23 (s, 9H); $^{13}$C NMR (100 MHz, CD$_3$OD) δ 178.4, 172.7, 159.1, 145.4, 142.7, 128.9, 128.3, 126.4, 121.1, 84.0, 76.4, 68.4, 60.1, 60.0, 39.9, 27.4, 19.0; ESI-HRMS m/z calcd for C$_{25}$H$_{29}$NO$_{10}$P (M−H)$^-$: 534.1529. found: 534.1524.

2) Synthesis of Ac-Pro-Leu-His-Ser-Thr (PO$_2$POM$_2$)-amide (5)

Peptide 5 was synthesized on NovaSyn®TG Siber resin (Novabiochem, cat. no. 01-64-0092) using reagent 1 under standard Fmoc-based protocols employing N-methyl-2-pyrrolidone (NMP) as solvent and 1-O-benzotriazole-N,N,NUP-tetramethyl-uronium-hexafluorophosphate (HBTU) (5.0 equivalents), hydroxybenzotriazole (HOBT) (5.0 equivalents) and N,N-diisopropylethylamine (DIPEA) (10.0 eq) as coupling reagents Amino terminal acetylation was achieved using 1-acetylimidazole. Following acetylation the resin (0.1 mmol) was treated with POMI (242 mg, 1.0 mmol) and DIPEA (0.174 mL, 1.0 mL) in DMF (3 mL) for 4 hours. The finished resin was washed with DMF, MeOH, CH$_2$Cl$_2$ and diethyl ether and then dried under vacuum (overnight).

The peptide was cleaved from the resin using 1% TFA in CH$_2$Cl$_2$ (10 min) Resin was removed by filtration, the filtrate was concentrated under vacuum; precipitated with cold ether and the precipitate was washed with cold ether. The resulting solid was dissolved in 50% aqueous acetonitrile (5 mL) and purified by reverse phase preparative HPLC using a Phenomenex C18 column (21 mm dia×250 mm, cat. no: 00G-4436-P0) with a linear gradient from 0% aqueous acetonitrile (0.1% trifluoroacetic acid) to 100% acetonitrile (0.1% trifluoroacetic acid) over 30 minutes at a flow rate of 10.0 mL/minute. Lyophilization provided 5 as a white powder (>99% pure by HPLC-MS). ESI-HRMS m/z calcd for C$_{38}$H$_{64}$N$_8$O$_{15}$P (M+H)$^+$: 903.4229. found: 903.4227.

Scheme 2: Synthesis of bis-POM-protected peptide 5 using reagent 1.

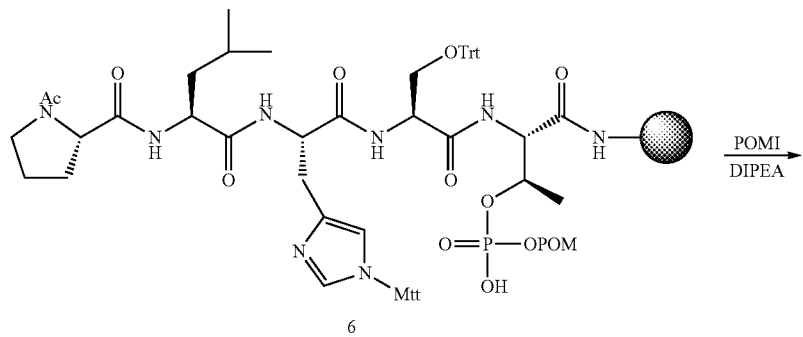

6

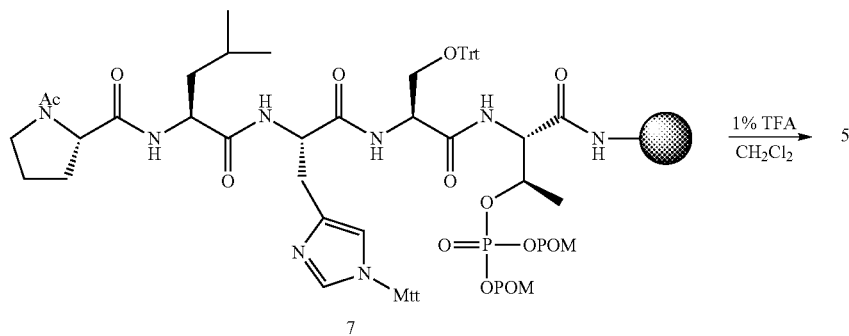

7

3) Synthesis of Compound 2
(N-Fmoc-Pmab(POM)$_2$-OH)

COMPOUND 2 (or Reagent 2)

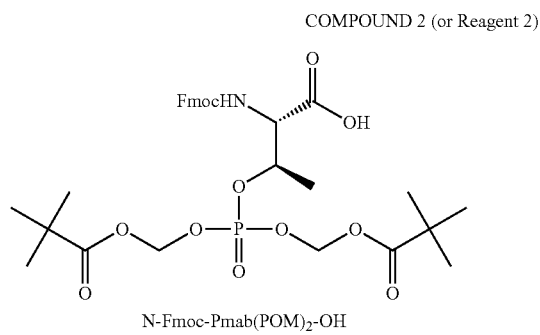

N-Fmoc-Pmab(POM)$_2$-OH

Scheme 3: Reagents and conditions: (i) 1. LiOH·H$_2$O, THF—H$_2$O, 0° C. - rt, (2 h); 2. BnBr, NaHCO$_3$, DMF, rt, (12 h) (80% yield for two steps). (ii) 1. TFA:CH$_2$Cl$_2$ (1:10; v/v) (1 h); 2. POMI, DIPEA, DMF, rt, (12 h). (iii) 1. 10% Pd/C, H$_2$, MeOH (1 h); 2. Fmoc—OSu, NaHCO$_3$, 1-6-dioxane:H$_2$O (1:1, v/v) (12 h) (55% for 4 steps).

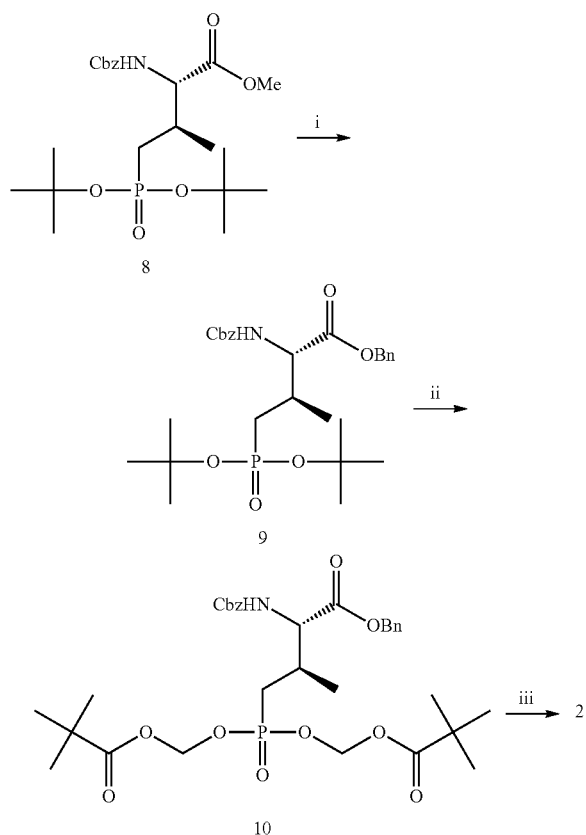

Preparation of reagent 2 began with N-Cbz-Pmab(Bu$^t_2$)—OMe. Benzyl trans-esterification of 8 to 9 was accomplished by initial LiOH-catalyzed hydrolysis of the methyl ester followed by reaction of the free acid with benzyl bromide (NaHCO$_3$ in DMF, 80% yield for two steps, Scheme 3). Subsequent treatment of 9 with pivaloyloxymethyl iodide (POMI) and diisopropylethyl amine (DIPEA) in DMF provided the corresponding bis-POM-protected intermediate (10). Hydrogenolytic removal of amino and carboxyl protecting groups and introduction of N-Fmoc-protection by treatment with 9-fluorenylmethyl succinimidyl carbonate (Fmoc-OSu) in aqueous THF with NaHCO$_3$, gave the desired reagent 2 (55% yield from 9).

Synthesis of Compound 9

To a solution of compound 8 (Liu et al. Tetrahedron 2009, 65, 9673-9679) (0.26 g, 0.57 mmol) in THF—H$_2$O (4/1; 5 mL) at 0° C. was added a solution of LiOH.H$_2$O (48 mg, 1.14 mmol) and the mixture was stirred at room temperature until all starting material was consumed as indicated by TLC. The solution pH was adjusted to 2-3 by the addition of 1N aqueous HCl and THF was removed by evaporation. The residue was extracted (EtOAc) and the combined organic phase was washed with brine, dried (MgSO$_4$), filtered and concentrated. To a solution of the crude residue in DMF (5.0 mL) were added sequentially, NaHCO$_3$ (95 mg, 1.14 mmol) and BnBr (0.10 mL, 0.85 mmol) at room temperature under argon and the mixture was stirred until the starting material was consumed as indicated by TLC. The mixture was diluted with EtOAc and washed with H$_2$O and brine, dried (MgSO$_4$) and filtered and concentrated. Purification by silica gel column chromatography (CH$_2$Cl$_2$: MeOH from 100:1 to 30:1) afforded 9 as a colorless oil (0.25 g, 80% for two steps). $[a]D^{21.6}$ −0.59 (c 1.0, CHCl3); $^1$H NMR (400 MHz, CDCl3) δ 7.40-7.28 (m, 10H), 5.91 (d, J=8.0 Hz, 1H), 5.20-5.06 (m, 4H), 4.38-4.31 (m, 1H), 2.42 (brs, 1H), 1.84-1.69 (m, 1H), 1.57-1.48 (m, 1H), 1.47-1.45 (m, 18H), 1.10 (d, J=8.0 Hz, 3H) ppm; $^{13}$C NMR (100 MHz, CDCl3) δ 171.7, 156.4, 136.5, 135.4, 128.8, 128.7, 128.6, 128.3, 82.4, 82.3, 82.2, 67.4, 67.2, 59.8, 59.7, 34.0, 32.6, 30.59, 30.56, 17.6 ppm; ESI-HRMS m/z calcd for C$_{28}$H$_{41}$NO$_7$P (M+H)$^+$: 534.2621. found: 534.2594.

Synthesis of Compound 10

Compound 9 (0.27 g, 0.5 mmol) in 10% TFA (CH$_2$Cl$_2$) was stirred at room temperature (1 h), then volatiles were removed under vacuum and the residue was taken up in DMF with POMI (0.32 mL, 2.0 mmol) and DIPEA (0.35 mL, 2.0 mmol) and stirred at room temperature under argon (overnight). The solution was stirring overnight. The mixture was diluted with H$_2$O, extracted with EtOAc and the combined organic extracts were washed with H$_2$O, and brine, dried (MgS$_{O4}$), filtered and concentrated. Purification by silica gel chromatography (EtOAc:hexanes from 1:4 to 1:1) afforded 10 as a white semi-solid (0.24 g, 74% yield for two steps). $[a]D^{21.9}$ 2.88 (c 0.7, CHCl$_3$); $^1$H NMR (400 MHz, CDCl3) δ 7.42-7.18 (m, 10H), 5.70-5.60 (m, 4H), 5.56 (d, J=12.0 Hz, 1H), 5.19 (s, 2H), 5.11 (s, 2H), 4.42-4.34 (m, 1H), 2.45 (brs, 1H), 2.04-1.91 (m, 1H), 1.78-1.67 (m, 1H), 1.22 (s, 9H), 1.21 (s, 9H), 1.08 (d, J=4.0 Hz, 3H) ppm; $^{13}$C NMR (100 MHz, CDCl$_3$) δ 177.1, 171.1, 156.3, 136.3, 135.2, 128.9, 128.8, 128.7, 128.44, 128.35, 81.7, 81.5, 67.6, 67.4, 59.2, 59.1, 38.9, 31.9, 30.3, 29.9, 28.9, 27.0, 17.5 ppm; ESI-MS m/z calcd for C$_{32}$H$_{45}$NO$_H$P (M+H)$^+$: 650.3. found: 650.3.

Synthesis of Compound 2

A solution of 10 (0.18 g, 0.28 mmol) in MeOH was hydrogenated over 10% Pd/C (30 mg) until the reaction was complete as indicated by TLC. The mixture was filtered, evaporated to dryness and reacted with Fmoc-OSu (0.19 g, 0.55 mmol) and NaHCO3 (70 mg, 0.83 mmol) in dioxane: H$_2$O (1:1, 5.5 mL) at room temperature (overnight). The mixture was acidified with 1N HCl, extracted with EtOAc and the combined organic phases were washed with brine, dried (MgSO$_4$), filtered and the filtrate concentrated. Purification by silica gel column chromatography (CH$_2$Cl$_2$:MeOH from 20:1 to 4:1) provided 2 as a colorless oil (0.14 g, 75% yield for two steps). [a]D$^{21.0}$ 12.8 (c 0.66, CHCl3); $^1$H NMR (400 MHz, CDCl3) δ 7.77 (d, J=8.0 Hz, 2H), 7.60 (d, J=8.0 Hz, 2H), 7.40 (t, J=8.0 Hz, 2H), 7.32 (td, J1=8.0 Hz, J2=4.0 Hz, 2H), 5.78-5.64 (m, 5H), 4.51-4.44 (m, 1H), 4.40 (d, J=8.0 Hz, 2H), 4.22 (t, J=8.0 Hz, 1H), 2.54 (brs 1H), 2.18-2.03 (m, 1H), 1.97-1.83 (m, 1H), 1.24 (s, 9H), 1.23 (s, 9H), 1.13 (d, J=8.0 Hz, 3H) ppm; $^{13}$C NMR (100 MHz, CDCl3) δ 177.2, 172.8, 156.4, 144.0, 143.8, 141.5, 128.0, 127.3, 125.3, 120.2, 82.0, 67.5, 58.3, 58.2, 47.3, 39.0, 31.4, 30.1, 28.7, 27.0, 17.62, 17.55 ppm; ESI-HRMS m/z calcd for C$_{32}$H$_{42}$NO$_{11}$PNa (M+Na)$^+$: 670.2393. found: 670.2376.

4) Solid-Phase Synthesis of Peptide 11

Scheme 4. Synthesis of bis-POM-protected peptide 11 using compound 2

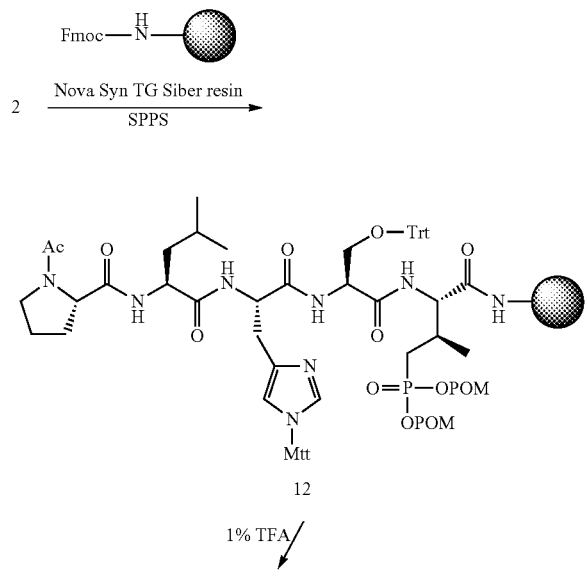

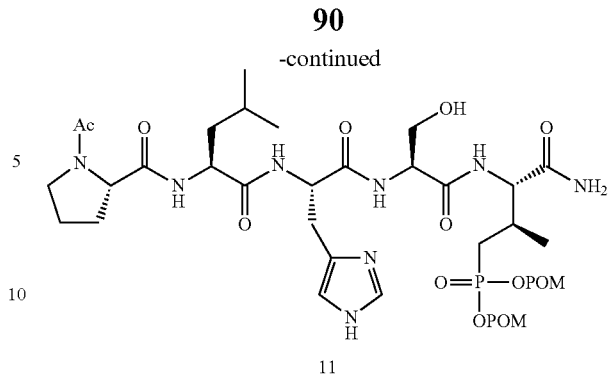

11

Standard Fmoc-protected amino acids were purchased from Novabiochem. Peptides were synthesized on NovaSyn® TG Siber resin (Novabiochem, cat. no. 01-64-0092) using Fmoc-based solid-phase protocols in N-methyl-2-pyrrolidone (NMP). 1-O-Benzotriazole-N,N,N',N'-tetramethyl-uronium-hexafluoro-phosphate (HBTU) (5.0 eq.), hydroxybenzotriazole (HOBT) (5.0 eq.) and N,N-diisopropylethylamine (DIPEA) (10.0 eq.) were used as coupling reagents Amino terminal acetylation was achieved using 1-acetylimidazole. The finished resin (12) was washed with DMF, MeOH, CH$_2$Cl$_2$ and diethyl ether and then dried under vacuum (overnight). Peptide 11 was cleaved from the resin using 1% TFA in CH2Cl2. The resin was removed by filtration and the filtrate was concentrated under vacuum, then precipitated with cold ether and the precipitate washed with cold ether. The resulting solid was dissolved in 50% aqueous acetonitrile (5 mL) and purified by reverse phase preparative HPLC using a Phenomenex C18 column (21 mm dia×250 mm, cat. no: 00G-4436-P0) with a linear gradient from 0% aqueous acetonitrile (0.1% trifluoroacetic acid) to 100% acetonitrile (0.1% trifluoroacetic acid) over 30 minutes at a flow rate of 10.0 mL/minute. Lyophilization gave peptide 11 as a white powder (>99% pure by HPLC). ESI-MS m/z calcd for C$_{39}$H$_{66}$N$_8$O$_{14}$P (M+H)$^+$: 901.4. found: 901.4.

5) Synthetic Scheme for the Preparation of Peptide Derivatives of the Invention

Scheme 5

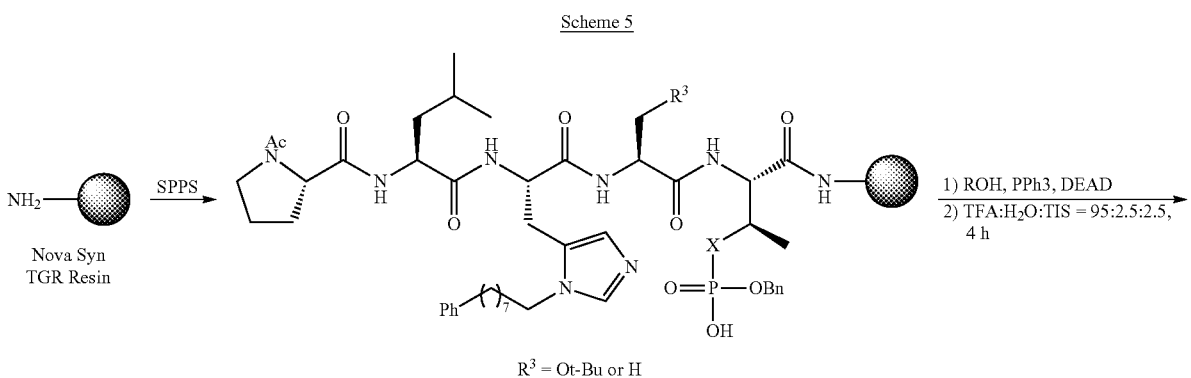

R$^3$ = Ot-Bu or H

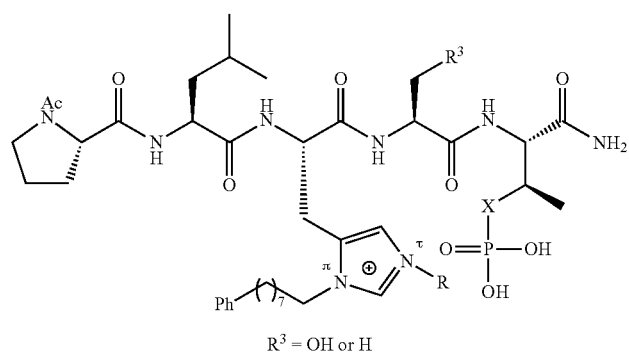
R³ = OH or H
Compounds of Table 2 were prepared according to Scheme 5.
Scheme 6
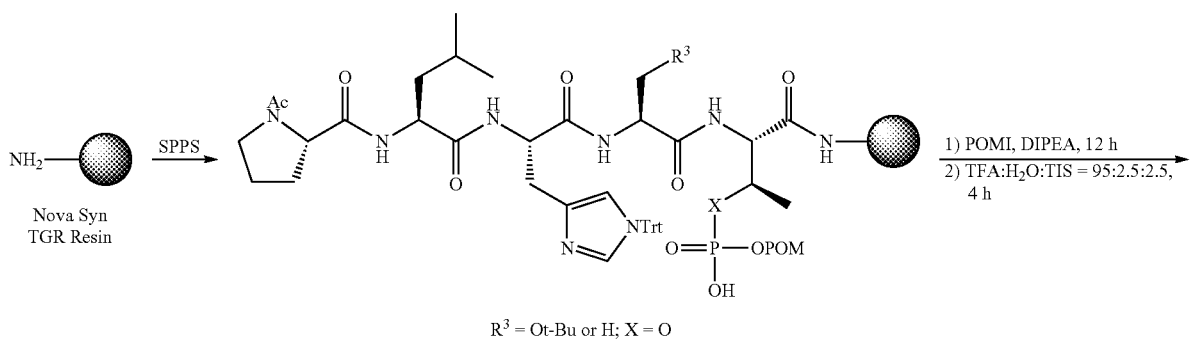
R³ = Ot-Bu or H; X = O
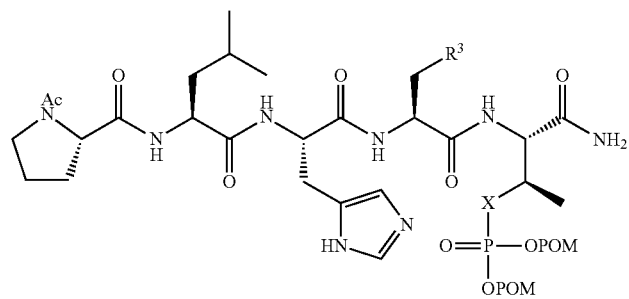
R³ = OH or H; X = O Compound Nos. A1 and A2 (Table 1) were prepared according to Scheme 6.
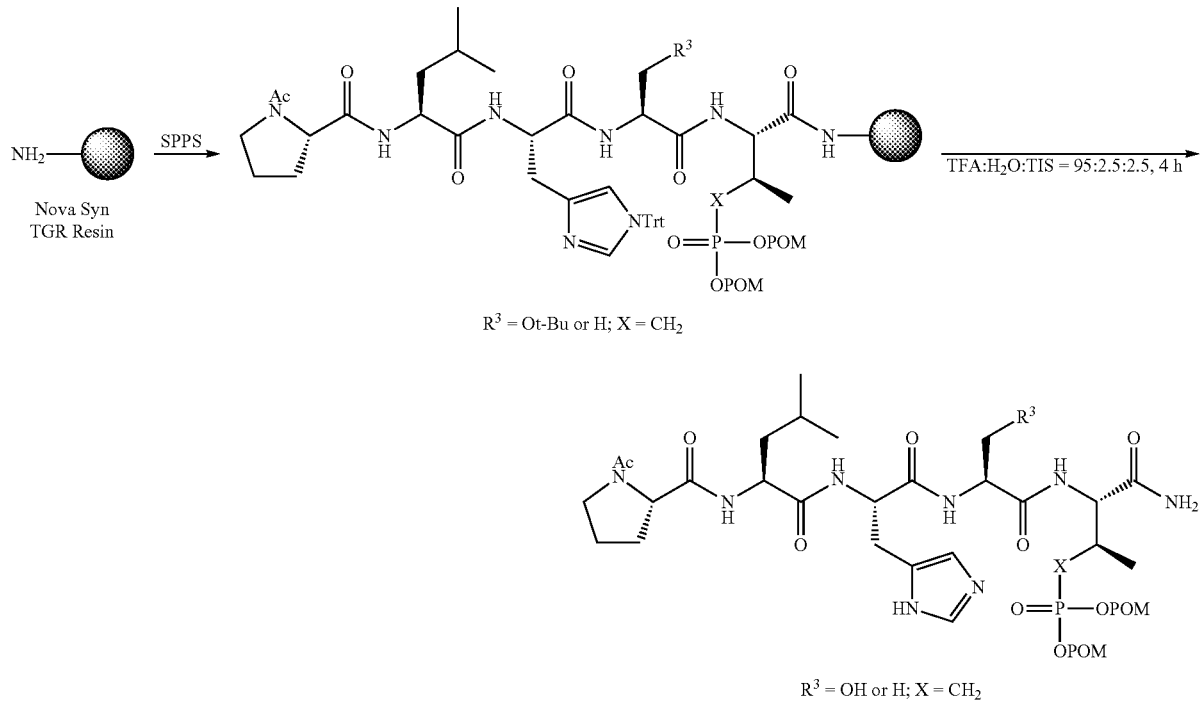
Compound Nos. A3 and A4 (Table 1) were prepared according to Scheme 7.
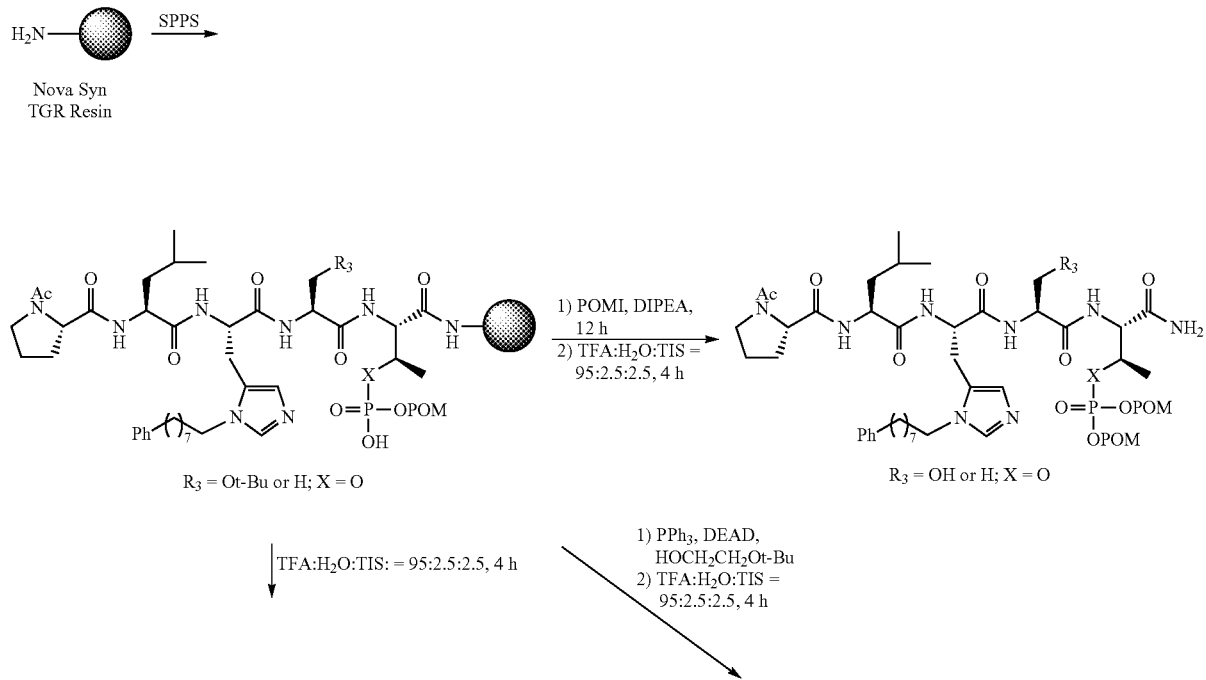

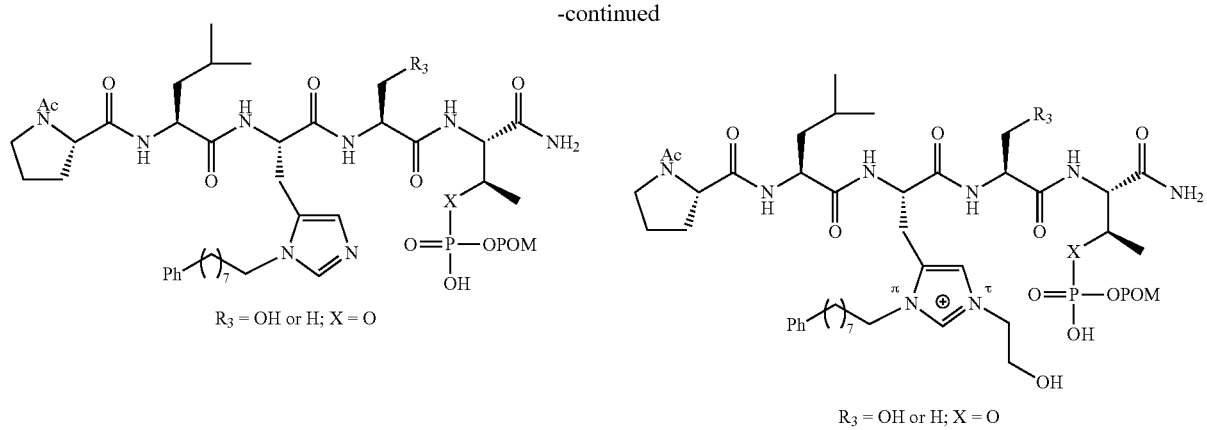

R₃ = OH or H; X = O

Compound Nos. A5-A8, A10, and A11 (Table 1) were prepared according to Scheme 8.

5-carboxyfluorescein-Ahx-GPLATS-pT-PKNG for Plk3 PBD) were incubated, at the final concentration of 2 nM, Scheme 9

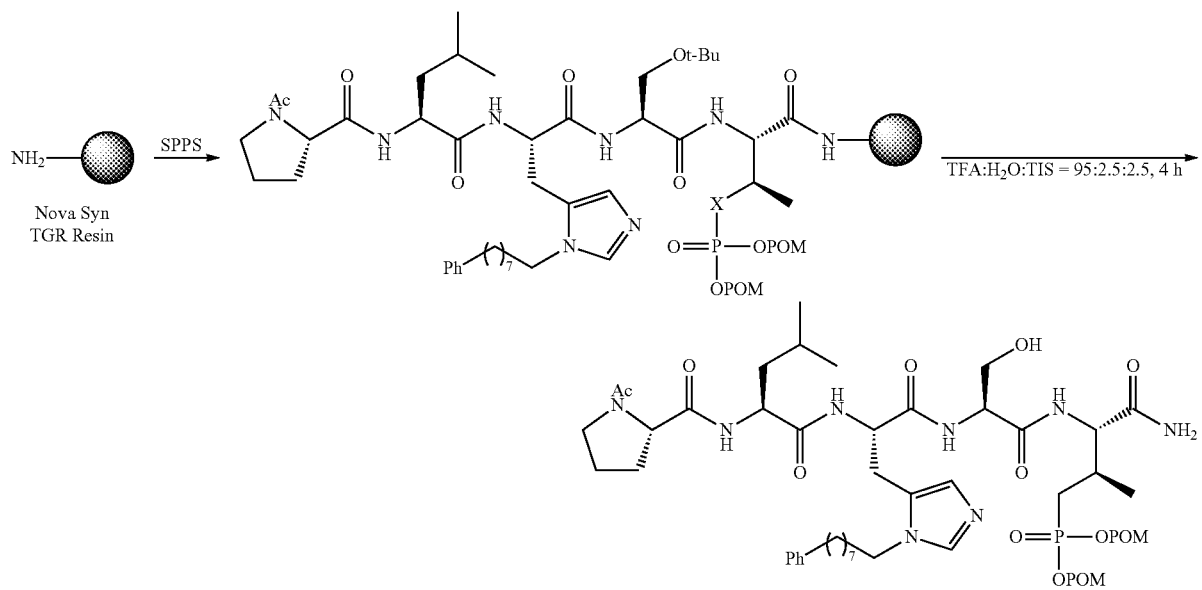

Compound No. A9 (Table 1) was prepared according to Scheme 9.

II. Biological Examples

Materials and Methods
Methods

Peptide-binding, GST-PBD pull-down, and ELISA-based PBD-binding inhibition assays. Peptide binding and GST-PBD pull-down assays were performed as described previously (15). An ELISA-based PBD-binding inhibition assay was carried out using an immobilized biotinylated 9-mer p-T78 peptide {Biotin-C—(CH2)6-(CH2)6-DPPLHSpTAI-NH2} and the cellular lysates expressing HA-EGFP-Plk1.

Fluorescence polarization assays. Indicated 5-carboxy-fluorescein-labeled peptides (5-carboxyfluorescein-Ahx-DPPLHS-pT-AI-NH2 for Plk1 PBD, 5-carboxyfluorescein-Ahx-GPMQTS-pT-PKNG for Plk2 PBD, and with various concentrations of bacterially-expressed purified PBDs of Plk1, Plk2 and Plk3 in a binding buffer containing 10 mM Tris (pH 8.0), 1 mM EDTA, 50 mM NaCl, and 0.01% Nonidet P-40. Fluorescence polarization was analyzed 10 mM after mixing of all components in the 384-well format using a Molecular Devices SpectraMax Paradigm Multi-Mode Microplate Detection Platform. All experiments were performed in triplicate. Obtained data were plotted using GraphPad Prism software version 6.

Isothermal titration calorimetry analyses. The calorimetric titrations were carried out using purified recombinant PBDs (for Plk1 and Plk2) from bacterial cells and the indicated peptides. Further details are presented in Online Supplemental Materials.

Crystallization, Data Collection, and Refinement. All initial crystallization screens for the Plk1 PBD-PLHSpT complex were performed on an Art Robbins Phoenix Liquid Handling System using Index (Hampton Research, Aliso Viejo, Calif.) and PEGs (Qiagen, Valencia, Calif.) crystallization kits. All subsequent crystals were grown using the hanging-drop vapor diffusion method at room temperature. PBD and the kinase domain of Plk1 were concentrated to ~30 mg/ml in buffer A (20 mM Tris-Cl, pH 8.0, 500 mM NaCl, 3 mM DTT). The phosphopeptide Ac-PLHSpT was dissolved in buffer A. The phosphopeptide and PBD were added in 2:1 stoichiometric ratio, respectively, and the final concentration was adjusted to ~15 mg/ml. Crystals of this complex were grown by adding 1 μl of this complex to 1 μl of well solution (0.2 M di-potassium phosphate, 20% w/v PEG 3350). The complex between PBD and kinase domain was formed similarly using a 1:1 stoichiometric ratio, and 0.2 M lithium sulfate monohydrate, 0.1 M Bis-Tris, pH 5.5, 25% w/v PEG 3350 as the well solution. Crystals formed within one week and were soaked for 5 minutes in mother liquor constituted with 20% v/v glycerol prior to flash-freezing in liquid nitrogen. The complex of PBD and Ac-PLHSpT crystallized in the space group P212121 (a=35.19 Å, b=65.76 Å, c=104.11 Å). The kinase domain of Plk1 precipitated and PBD crystallized in the space group P21 (a=35.29 Å, b=102.29 Å, c=68.55 Å, β=) 93.24°.

Crystals of the Plk1 PBD-PPHSpT complex were obtained in a similar fashion using a well solution of 0.1 M MES buffer (pH 6.0) containing 15% PEG 3350. The crystals were soaked for 5 minutes in the mother liquor constituted with 15% v/v glycerol, 10 mM DTT and 2 mM of the phosphopeptide Ac-PPHSpT prior to freezing in liquid nitrogen. This complex crystallized in the space group P212121 (a=35.44 Å, b=66.50 Å, c=105.82 Å). All data were collected at 100K. The data for PBD, and PBD in complex with Ac-PLHSpT were collected at the SER-CAT beamline 22-ID, at the Advanced Photon Source (APS), on a MAR 300CCD detector. The data for the complex of PBD and Ac-PPHSpT were collected at APS beamline 24-ID-C at 100 K. All data were processed and scaled using the HKL2000 package20. Phasing of the data was done by molecular replacement using a previously published structure (PDB ID; 1UMW). The structures were refined independently of each other with the program REFMAC521 and CNS1.122. Model building was performed using Coot (23) and XtalView (24) (Table 4).

Crystals of the Plk1 PBD-LHSpTA complex were grown by hanging drop vapour diffusion using 1 μl of protein solution (12 mg/ml in 10 mM Tris-Cl, pH 8.0, 0.5 M NaCl, 10 mM DTT, 2 mM Ac-LHSpTA-NH2 peptide) mixed with 1 μl of well solution consisting of 32.5% PEG 2000 MME, 0.1 M Tris-Cl, pH 8.5, 0.2 M trimethyl-amine N-oxide. Crystals grew overnight at room temperature. For data collection, a crystal was looped from the drop and flash frozen by direct transfer to a cryostream at 100 K. Data were collected with a rotating anode home source on a Rigagku R-axis IV detector and processed using the HKL2000 package20. A molecular replacement solution was found with AMoRe (25). Initial refinement was done with CNS 1.2126 with manual model fitting using XtalView (24). The final rounds of refinement were completed in PHENIX 1.3 (27) with the addition of riding hydrogens.

Peptide pull-down assay: Peptide pull-down assays were carried out essentially as described previously (Yun, S.-M. et al. Nat. Struct. Mol. Biol. 16, 876-882 (2009). To study Plk1 PBD-binding specificity, p-T78 peptide or its derivatives were cross-linked to beads using SulfoLink Coupling Gel (Pierce, Rockford, Ill.) via either an N-terminal Cys-(CH2) 6-CO linker [PLHSpT, PLHST, 4j, and 4j (S/A)] or an N-terminal Cys residue conjugated to PEG moiety [PEG-4j* and PEG-4j*(S/A)]. Mitotic lysates expressing Plk1-3 were prepared from 293T cells transfected with Flag-Plk1 (K82M), Flag-Plk2 (K108M) or Flg-Plk3 (K52R) (a gift of Wei Dai, New York University School of Medicine, NY) and treated with 200 ng/ml of nocodazole for 16 h. After incubating the cell lysates prepared in TBSN buffer {20 mM Tris-Cl (pH8.0), 150 mM NaCl, 0.5% Np-40, 5 mM EGTA, 1.5 mM EDTA, 20 mM p-nitrophenylphosphate and protease inhibitor cocktail (Roche, Nutley, N.J.)} with the bead-immobilized ligands for 2 h at 4° C., the ligand-associating proteins were precipitated, washed, boiled in sodium dodecyl sulfate (SDS) sample buffer, separated by 8% SDS-polyacrylamide gel electrophoresis (PAGE), and then subjected to immunoblotting analysis with anti-Flag antibody and the enhanced chemilunimescence (ECL) detection system (Pierce). The same membrane was also stained with Coomassies (CBB). Signal intensities were quantified using Image J program.

Peptide and GST-PBD pull-down assays. For Plk1 pull-down assays with immobilized peptides, we used total lysates prepared from mitotic HeLa cells. HeLa cells contain no mutations in Plk1 coding sequence and the level of Plk1 expression is high (2). Cells treated with 200 ng/ml of nocodazole for 16 h were lysed in TBSN buffer {20 mM Tris-Cl (pH8.0), 150 mM NaCl, 0.5% NP-40, 5 mM EGTA, 1.5 mM EDTA, 0.5 mM Na3VO4, 20 mM p-nitrophenyl phosphate, and protease inhibitor cocktail (Roche, Nutley, N.J.)}, and then clarified by centrifugation at 15,000×g for 20 mM at 4° C. The resulting lysates were incubated with bead-immobilized peptides (40 μM per binding) for 2 h, precipitated, washed, and then boiled in sodium dodecyl sulfate (SDS) sample buffer to elute the associated proteins. Samples were separated by 10% SDS-polyacrylamide gel electrophoresis (PAGE), and then either stained with silver or transferred to PVDF membrane for immunoblotting analysis with anti-Plk1 antibody using the enhanced chemi-luminescence (ECL) detection system (Pierce).

To investigate the binding specificity of p-T78 peptides to various Plks, Flag-Plk1 (K82M), Flag-Plk2(K108M)3 or Flag-Plk3(K52R) (a gift of Wei Dai, New York University School of Medicine, NY) construct was first transfected into HeLa cells. Cellular lysates were prepared as above, mixed, and then incubated in TBSN buffer with the immobilized peptides indicated.

To determine whether PLHSpT binds to the phosphate pincer cleft of the PBD, bead-immobilized PLHSpT or the respective non-phospho PLHST control peptide was incubated with soluble control GST, GST-PBD, or GST-PBD (H538A K540M)4 for 2 h, washed, and then precipitated fraction was analyzed.

For p-Cdc25C pull-down assays, either bead-bound GST-PBD or the corresponding GST-PBD(H538A K540M) mutant was incubated with mitotic HeLa lysates in TBSN buffer supplemented with 2 mM DTT. To test the ability of the indicated peptides to compete the PBD-p-Cdc25C interaction, lysates were pre-incubated with GST-PBD for 1.5 h prior to the addition of the indicated peptides. Lysates were then incubated for additional 1.5 h, washed in the binding buffer, and then analyzed. For competition of the interaction between p-Cdc25C and endogenous Plk1, mitotic lysates were prepared in TBSN and incubated with the indicated peptides for 1 h before subjecting to immunoprecipitation with anti-Plk1 antibody.

ELISA-based PBD-binding inhibition assay. A biotinylated p-T78 peptide was first diluted with 1× coating solution (KPL Inc., Gaithersburg, Md.) to the final concentration of 0.3 μM, and then 100 μl of the resulting solution was immobilized onto a 96-well streptavidin-coated plate (Nalgene Nunc, Rochester, N.Y.). The wells were washed once with PBS plus 0.05% Tween20 (PBST), and incubated with 200 μl of PBS plus 1% BSA (blocking buffer) for 1 h to prevent non-specific binding. Mitotic 293A lysates expressing HA-EGFP-Plk1 were prepared in TBSN buffer (~60 μg total lysates in 100 μl buffer), mixed with the indicated amount of the competitors (p-T78 peptide and its derivative compounds), provided immediately onto the biotinylated peptide-coated ELISA wells, and then incubated with constant rocking for 1 h at 25° C. Following the incubation, ELISA plates were washed 4 times with PBST. To detect bound HA-EGFP-Plk1, the plates were probed for 2 h with 100 μl/well of anti-HA antibody at a concentration of 0.5 μg/ml in blocking buffer and then washed 5 times. The plates were further probed for 1 h with 100 μl/well of HRP-conjugated secondary antibody (GE Healthcare, Piscataway, N.J.) at a 1:1,000 dilution in blocking buffer. The plates were washed 5 times with PBST and incubated with 100 μl/well of 3,3',5,5'-tetramethylbenzidine (TMB) solution (Sigma, St. Louis, Mo.) as a substrate until a desired absorbance was reached. The reactions were stopped by the addition of 100 μl/well of stop solution (Cell Signaling Technology, Danvers, Mass.). The optical density (O.D.) was measured at 450 nm by using an ELISA plate reader (Molecular Devices, Sunnyvale, Calif.).

Cell culture, analysis of the cell proliferation and aberrant mitotic population, and indirect immunofluorescence microscopy: HeLa cervical carcinoma cell line CCL2, 293A and 293T cells were cultured as recommended by the American Type Culture Collection (Manassas, Va.), were cultured as recommended by American Type Culture Collection (Manassas, Va.). To prepare mitotic 293A cells expressing HA-EGFP-Plk1, cells were infected with adenovirus expressing HA-EGFP-Plk1 and arrested with 200 ng/ml of nocodazole for 16 h. To analyze the effect of the indicated compounds in cultured cells, logarithmically growing HeLa cells were treated with 200 μM of the indicated compounds for 24 h (a sufficient amount of time to enrich mitotically-arrested cells), treated with Hoechst 33342 for 10 mM, and then fixed with 4% paraformaldehyde.

In a separate experiment, HeLa cells were arrested with 2.5 mM thymidine for 16 h and released into fresh medium. Four hours after release, cells were treated with 200 μM of the compounds, harvested at the indicated time points, and then analyzed. Indirect immunofluorescence studies were performed as described previously (Liu, F. et al. Tetrahedron 65, 9673-9679 (2009)), using anti-Plk1 (Santa Cruz Biotechnologies, Santa Cruz, Calif.) and anti-α-tubulin (Sigma) antibodies followed by Texas red (red) and Alexa Fluor 488 (green)-conjugated secondary antibodies, respectively. Confocal images were acquired using a Zeiss LSM510 system mounted on a Zeiss Axiovert 100 M microscope (Carl Zeiss MicroImaging, Inc., Thornwood, N.Y.).

Isothermal titration calorimetry analyses. The calorimetric titrations were performed on a VP-ITC titration calorimeter (Microcal, Inc., Northampton, Mass.). In a typical experiment, 5 μl aliquots of a phosphorylated peptide were injected from a 250 μl syringe into a rapidly mixing (300 rpm) solution of Plk1 PBD (cell volume=1.3472 ml). Control experiments involved injecting identical amounts of the peptide solution into buffer without Plk1 PBD. The concentrations of Plk1 PBD were 0.033-0.052 mM, and those of the peptides were 0.145-0.365 mM, all concentration values determined by amino acid analysis. Titrations were carried out at 25° C. in 20 mM Tris-Cl (pH 7.5), 100 mM NaCl, 3 mM DTT. The isotherms, corrected for dilution/buffer effects, were fit using the Origin ITC Analysis software according to manufacturer's protocols. A nonlinear least-square method was used to fit the titration data and to calculate the errors. Consistent with the structural data, a 1:1 stoichiometry was assumed and the data were fit to a one-site binding model. From the binding curve, values for enthalpy and binding affinity were extracted. Thermodynamic parameters were calculated using $\Delta G = RT \ln K_a$, $\Delta G = \Delta H - T \Delta S$.

Cloning, Protein Expression, and Purification. Two forms of Plk1 PBD (residues 326-603 and residues 367-603) were expressed as fusion constructs with an N-terminal His6-DsRed tag in a vector based on pDEST-527 (Addgene, Cambridge, Mass.). Another form of Plk1 PBD (residues 371-603) was expressed with an N-terminal His6-MBP tag in a vector based on pET-28a (Novagen, Madison, Wis.). A TEV protease cleavage site was engineered between the tag and PBD. The vectors were expressed in either E. coli BL21(DE3)pLysS or Rosetta 2 cells (Novagen) with similar yield. Cells were grown to an optical density of 0.4 at 30° C. with vigorous shaking. The cultures were cooled to 20° C., induced by addition of IPTG to a final concentration of 0.4 mM, and incubated for 12 h. The cells were harvested and the pellets were frozen prior to lysis. All subsequent purification was done at 4° C. The frozen pellets were thawed in buffer A (20 mM Tris-Cl, pH 8.0, 500 mM NaCl, 3 mM DTT) and lysed by addition of 4% v/v BugBuster 10× protein extraction reagent (Novagen) and 0.1 mg/ml of DNase I (Sigma). The lysate was centrifuged at 40000×g for 30 minutes to pellet the cell debris and filtered through a 0.2 μm filter. The lysate was loaded onto HisTrap HP columns (Amersham Biosciences, Piscataway, N.J.) with 100 mM imidazole, washed with 100 mM imidazole in buffer A, and eluted with 500 mM imidazole in buffer A. The peaks containing the fusion protein were digested with TEV protease (1:100 molar ratio) overnight by dialysis against buffer A. The digestion was reloaded onto HisTrap HP column without imidazole, washed with buffer A, and eluted with 80 mM imidazole in buffer A. A HiLoad 16/60 Superdex 75 gel filtration column (Amersham) equilibrated with buffer A was used as the final step in purification. Full length PBD was dialyzed against a low salt buffer (20 mM Tris-Cl, pH 7.5, 100 mM NaCl, 3 mM DTT), and used in calorimetry experiments. The truncated forms of PBD were used for crystallography. The kinase domain of Plk1 (residues 1-337) was purified in the same manner. His6-MBP constructs were purified by Ni metal affinity chromatography, loaded on to an amylose-agarose column, and then eluted with 50 mM maltose in a buffer {10 mM Tris (pH 8), 0.5 M NaCl, 2 mM DTT}. The resulting protein was digested with TEV protease to cleave the tag, flowed through Ni column, and then finally subjected to gel filtration. The PBD of human Plk2 (residues 373 to 685) was cloned as a MBP fusion with a TEV protease cleavage site and purified as the same fusion with PBD of Plk1.

Cell culture and microinjection. HeLa cells were cultured as subconfluent monolayers under the conditions recommended by American Type Culture Collection (Manassas, Va.). To acutely inhibit the Cdc2 kinase activity, HeLa cells arrested with 200 ng/ml of nocodazole for 16 h were treated with 200 nM of BMI-1026 for 10 mM No mitotic exit was observed during the period of 10 mM BMI-1026 treatment. For microinjection experiments with the Pmab-containing mimetic peptides, cells were arrested for 16 h with 2.5 mM thymidine (Sigma) and released into fresh medium. Two hours after release from the S phase block, the indicated peptides (2.5 mM stock in PBS) were microinjected into the cells using Eppendorf® Transjector 5246 (Eppendorf®, Westbury, N.Y.) at the 150 hPa pressure level and the 0.5 second injection time. All the cells in a single grid were injected and then further incubated to monitor cell cycle progression. For microinjection experiments with the F2Pmab-containing mimetic peptides, cells were arrested with 2.5 mM thymidine for 16 h twice with a 9 h release interval, and then released into fresh medium. Seven hours after release from the G1/S phase block, the indicated peptides (4 mM stock in PBS) were microinjected similarly as above. Where indicated, peptides containing the final concentration of 30 ng/µl of pEGFP-C1 vector (Clontech®, Mountain View, Calif.) were used to visualize the injected cells.

To determine the level of Plk1 delocalization by the microinjected PLHS-Pmab peptide, cells were released for 5 h from the single thymidine (S phase) block and then microinjected. Four hours after microinjection, cells were fixed and subjected to immunostaining analyses as described below.

Similar methods were used for the experiments shown in FIG. 16 using the peptides indicated. HeLa cells were arrested at the G1/S boundary by double thymidine treatment and released into fresh medium. Six hours after release, the cells were microinjected with a mixture of 3 mM of peptides 21, 23 or 24 and 30 ng/µL of pEGFP-C1 vector and the cells were then photographed 15 h after G1/S release. Co-injected EGFP plasmid provided a convenient marker to identify the microinjected cells.

Electroporation. For the purpose of investigating a long term effect of the peptide, a 6-mer Biotin-conjugated p-T78 mimetic peptide {Biotin-(CH)6-PLHS-F2Pmab-A-NH2} was electroporated into asynchronously growing HeLa cells using a Bio-Rad® Gene Pulser (Bio-Rad® Laboratories, Hercules, Calif.) at 250 µFD and 300 V. Cells were then incubated for 2 days, fixed, and then subjected to immunostaining analysis.

Indirect immunofluorescence and confocal microscopy. Indirect immunostaining was carried out as described previously (5) using anti-Plk1 antibody (Santa Cruz Biotechnologies, Santa Cruz, Calif.) and anti-CREST antiserum (Cortex Biochem, San Leandro, Calif.). All the appropriate secondary antibodies were purchased from Jackson ImmunoResearch Laboratories, Inc. (West Grove, Pa.). Biotinylated F2Pmab-positive cells were detected by co-staining with FITC-conjugated Streptavidin (Invitrogen®, Carlsbad, Calif.). Chromosomes were visualized with 4',6-diamidino-2-phenylindole (DAPI) (Sigma). Digital images were collected with a Zeiss LSM510 confocal microscope. For the quantification of the fluorescence signal intensities, images of unsaturated fluorescence signals were acquired with the same laser intensity at 512×512 pixels and 12-bit resolution. Fluorescence intensities for localized signals were determined after subtracting the background signal intensities using Zeiss AIM confocal software.

Example 1

Enzymatic Deprotection of Peptides Containing POM-Protected pThr and Pmab Residues Hydrolysis assays were run on five POM-protected peptides (see below):

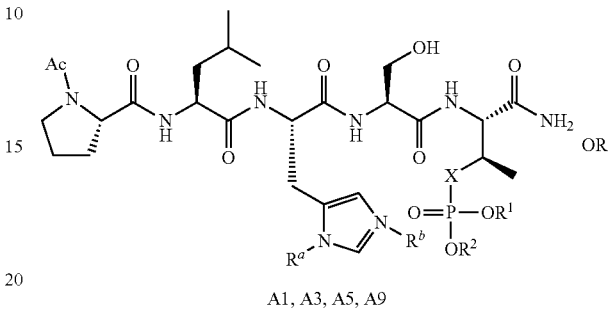

A1, A3, A5, A9

A10

TABLE 3

| Entry | Comp. No. | X | $R^1$ | $R^2$ | $R^a$ | $R^b$ |
|---|---|---|---|---|---|---|
| 1 | A1 | O | POM | POM | H | absent |
| 2 | A3 | $CH_2$ | POM | POM | H | absent |
| 3 | A5 | O | POM | POM | $Ph(CH_2)_8$ | absent |
| 4 | A9 | $CH_2$ | POM | POM | $Ph(CH_2)_8$ | absent |
| 5 | A10 | O | POM | H | $Ph(CH_2)_8$ | $CH_2CH_2OH$ |

There are three types of hydrolysis experiment performed in these peptides. The half-life of each peptide in different type of hydrolysis experiment was calculated and listed in Tables 4-6.

Type 1: 200 µM peptide with Porcine Liver Esterase (58 units, according the protocol presented in Srivastva, D. N.; Farquhar, D. *Bioorg. Chem.* 1984, 12, 118). The results are provided in Table 4:

TABLE 4

| Half-life of peptides in PLE | | |
|---|---|---|
| Entry | Comp. No. | Half-life (min) |
| 1 | A1 | 6.8 |
| 2 | A3 | 5.1 |
| 4 | A5 | 114 |
| 5 | A9 | 2.2 |
| 6 | A10 | 240 |

Type 2: 1 µM peptide in culture medium and 200 µM peptide in culture medium. The results are provided in Table 5 as follows:

TABLE 5

Half-life of peptides in culture medium

| Entry | Comp. No. | Half-life (min) |
|---|---|---|
| 1 | A5 (1 μM) | 32.2 |
| 2 | A5 (200 μM) | 446 |
| 3 | A10 (1 μM) | 412 |
| 4 | A10 (200 μM) | N.D.[a] |

[a] <5% hydrolysis product could be detected after 24 h incubation.

Type 3: 1 μM peptide in cell lysate. The results are provided in Table 6 as follows:

TABLE 6

Half-life of peptides in cell lysate

| Entry | Label | Half-life (min) |
|---|---|---|
| 1 | A5 (1 μM) | 139 |
| 2 | A10 (1 μM) | 89 |

PLE hydrolysis experiment. 0.05M potassium phosphate buffer (pH 7.4) was placed in centrifuge tube. A solution of selected peptide in methanol was added to the buffer. Final concentration of the peptide was 200 μM, MeOH was less than 1% in solution. Take 1 mL of the above solution, then added Pig liver esterase (57.6 units). The reaction mixture was then incubated at 37° C. by shaking. At different time point, certain amount (50 μL) of reaction mixture was taken and placed in a separate Eppendorf tube containing 1 equiv. volume MeCN (50 μL). After work-up, the hydrolysis product was monitored by LC-MS.

Culture medium hydrolysis experiment. Culture medium was placed in centrifuge tube. A solution of selected peptide in methanol was added to the culture medium. Final concentration of the peptide was 1 μM or 200 μM, MeOH was less than 1% in solution. The reaction mixture was then incubated at 37° C. by shaking. At different time point, certain amount (50 μL) of reaction mixture was taken and placed in a separate Eppendorf tube containing 1 equiv. volume MeCN (50 μL). After work-up, the hydrolysis product was monitored by LC-MS.

Cell lysate hydrolysis experiment. Cell lysate was placed in 96-well plate. A solution of selected peptide in DMSO was added to the cell lysate. Final concentration of the peptide was 1 μM, DMSO was less than 1% in solution. The reaction mixture was then incubated at 37° C. by shaking. At different time point, 1 equiv. by volume of MeCN was added to well to quench the reaction. After work-up, the hydrolysis product was monitored by LC-MS.

TABLE 7

Compared the half-life of PP4 and PP6 in different type of hydrolysis experiments (min)

| | PLE | 1 μM in culture medium | 200 μM in culture medium | 1 μM in cell lysate |
|---|---|---|---|---|
| A5 | 114 | 32.2 | 446 | 139 |
| A10 | 240 | 412 | N.D. | 89 |

Example 2

ELISA Binding Data for Select Peptide Derivatives

An ELISA-based PBD-binding inhibition assay was carried out on select peptide derivatives using an immobilized biotinylated 9-mer p-T78 peptide {Biotin-C—(CH2)6-(CH2)6-DPPLHSpTAI-NH 2} and the cellular lysates expressing HA-EGFP-Plk1.ELISA assays were run as previously reported (see: Nat. Struct. Mol. Biol. 2009, 16, 876-882; Nat. Chem. Biol. 2011, 7, 595-601; ACS Chem. Biol. 2012, 7, 805-810; ChemBioChem 2012, 13, 1291-1296). The test data was provided in FIGS. 1-3 and discussed infra.

TABLE 8

| | $IC_{50}/\mu M$ |
|---|---|
| PLHSpT | 9.4 |
| p-13mer | 0.070 |
| 4j | 0.0030 |
| Qn48 | 0.0013 |
| Qn113 | 0.82 |
| Qn49 | 0.0013 |
| Qn50 | 0.0013 |
| Qn51 | 0.0013 |
| Qn52 | 0.0039 |
| Qn53 | 0.0047 |
| Qn54 | 0.0061 |
| Qn55 | 0.0048 |
| Qn63 | 0.039 |
| Qn74 | 0.0012 |
| Qn114 | 0.15 |
| Qn75 | 0.0019 |
| Qn76 | 0.0026 |
| Qn77 | 0.015 |
| Qn110 | 0.0093 |
| Qn115 | 17 |

Figure 2:
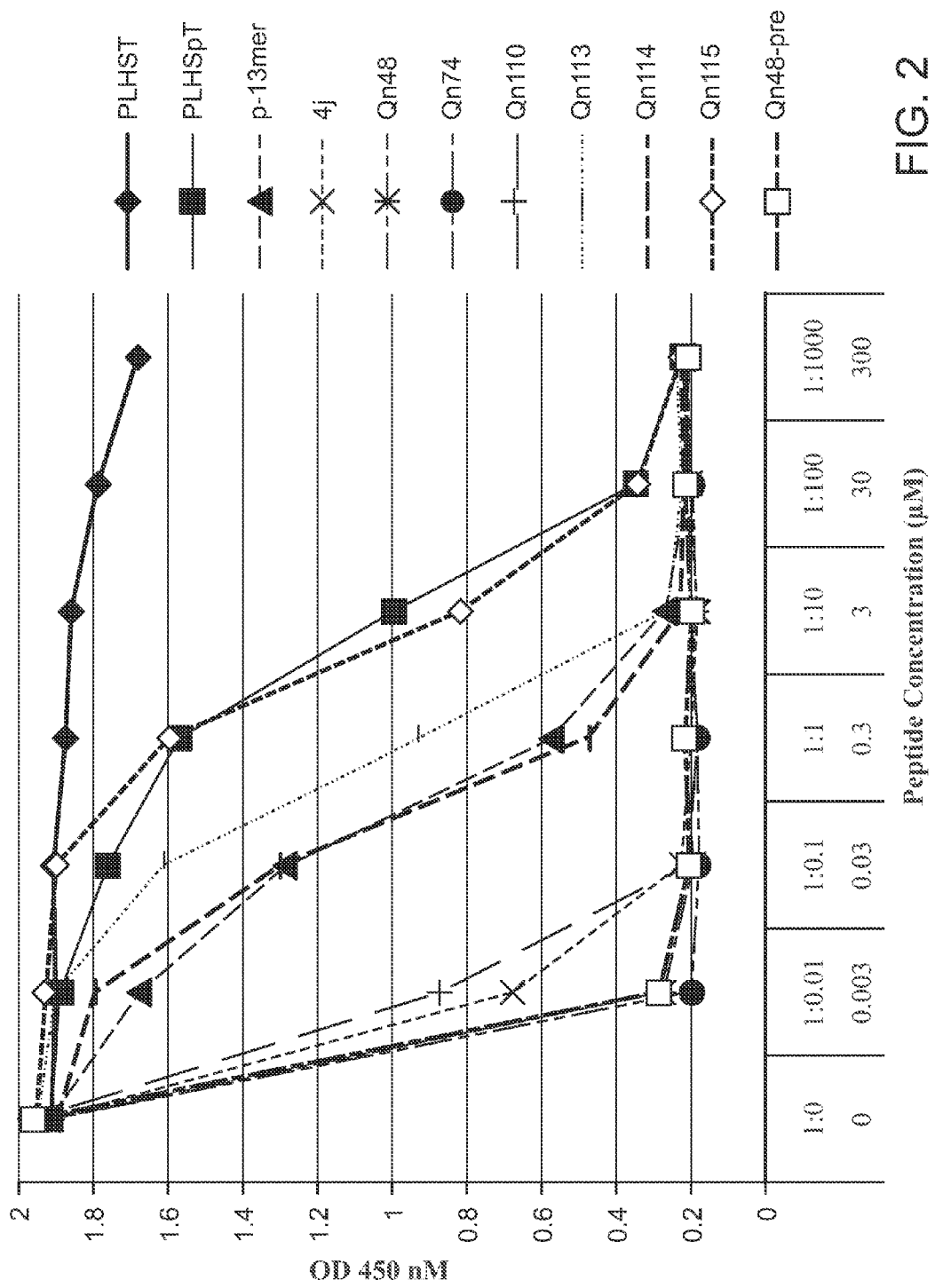
FIG. 2 is a chart showing data from ELISA binding assays on select compounds using cell lysates containing full-length Plk1 that were incubated with the compounds prior to binding.

The test data provided in FIG. 2 was generated from an assay, in which cell lysates containing full-length Plk1 were incubated with test peptides (1.5 h), and test peptides were then added and binding was allowed to occur over 1 h prior to quenching.

Figure 3:
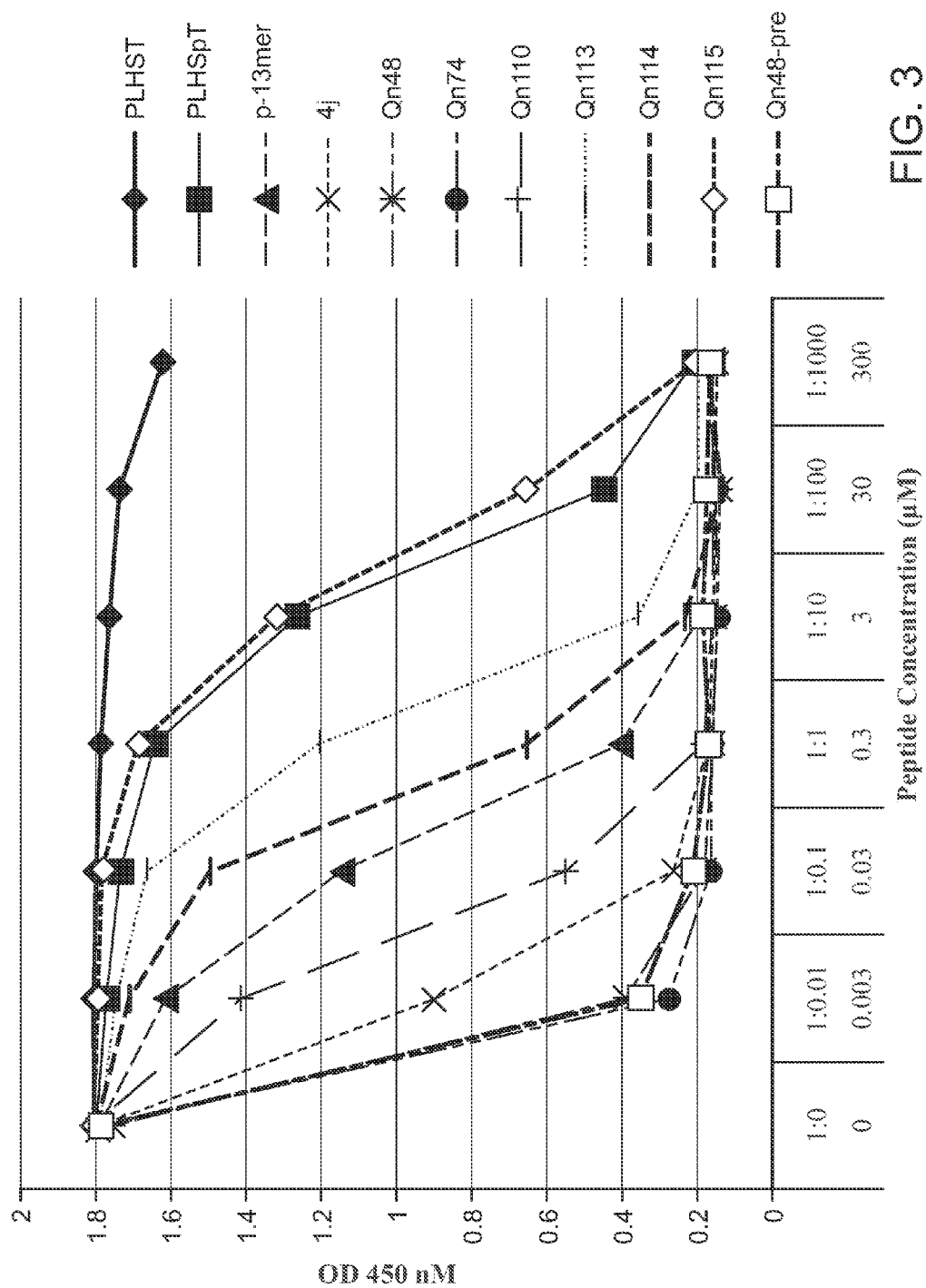
FIG. 3 is a chart showing data for select compounds obtained from ELISA binding assays using cell lysates containing full-length Plk1 that were incubated without the compounds prior to binding.

An assay in which cell lysates containing full-length Plk1 were incubated without test peptides (1.5 h) was also conducted. Binding was then allowed to occur over 1 h prior to quenching. The test results are shown in FIG. 3.

Example 3

PBD Floresence Polarization Binding Assay

Figure 4:
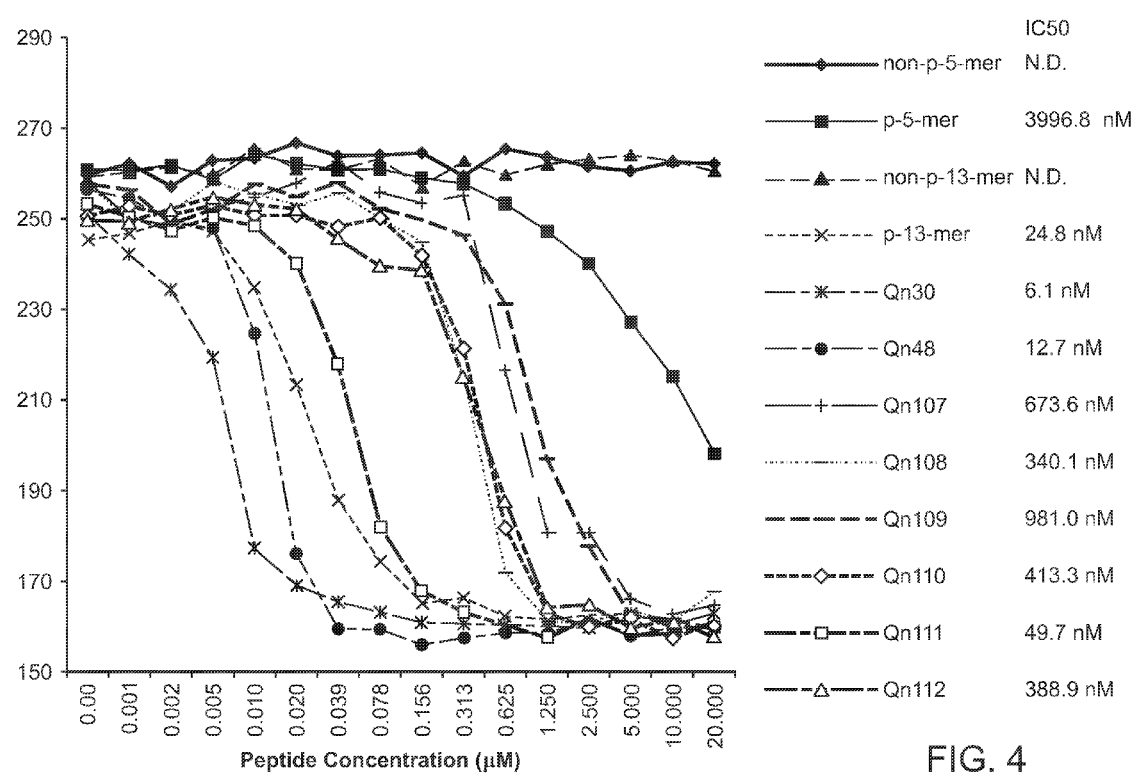
FIG. 4 presents PBD florescence polarization binding data for select compounds.
Figure 5A:
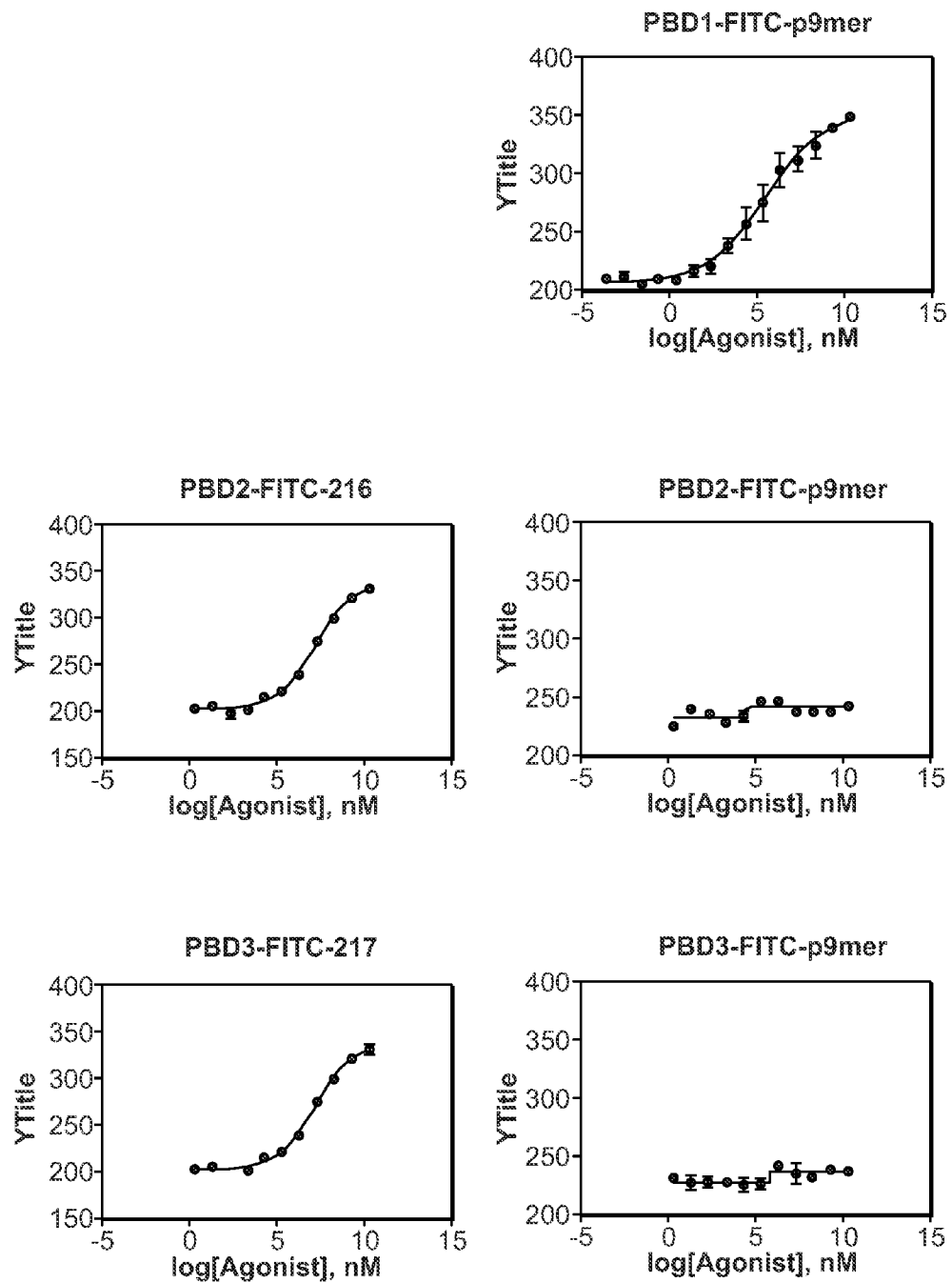
FIG. 5 is a number of graphs showing florescence polarization Plks specific data for select compounds.
Figure 5B:
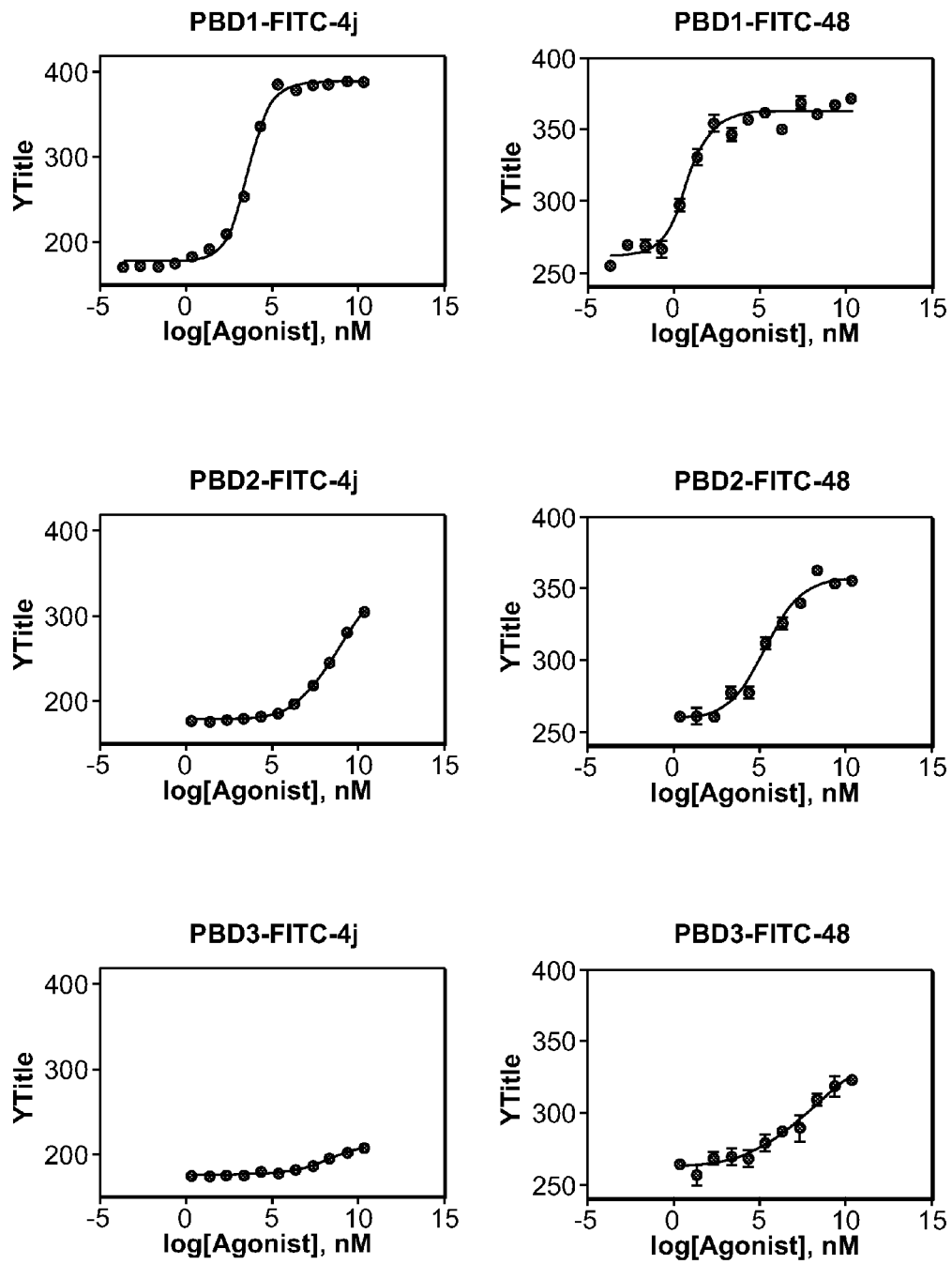
Figure 5C:
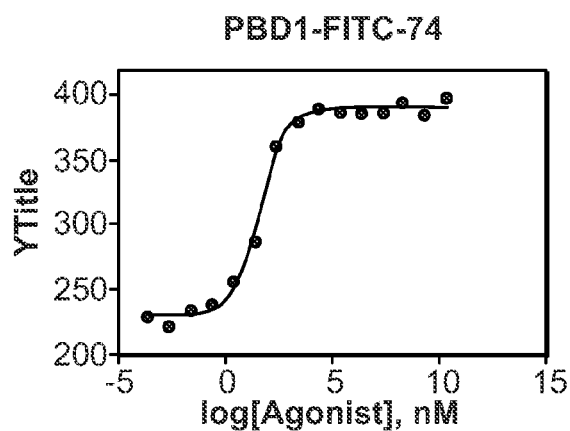
Figure 5C:
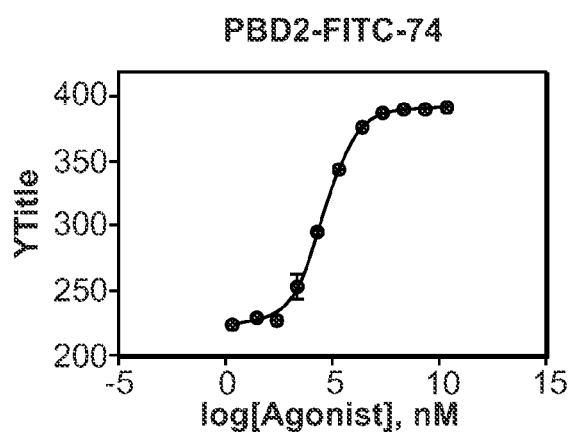
Figure 5C:
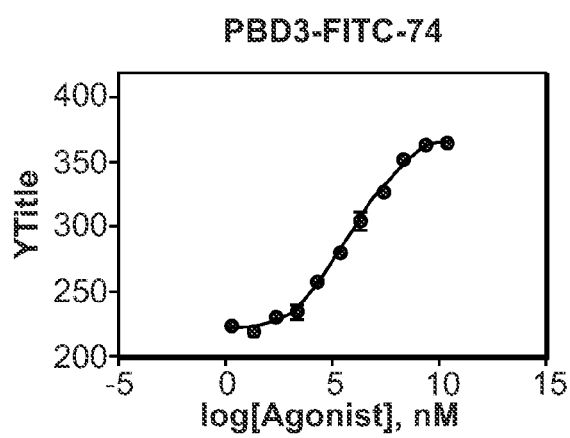

The FP competitive assay shows that the pThr monoester containing peptide demonstrated good binding affinity (~10 nM; see FIG. 4).

To test for Plk specificity of the selected peptides, the inventors prepared appropriate FITC-labeled peptides and performed direct FP binding assays. These assays showed approximately two orders of magnitude less affinity for FITC-Qn48 against Plk2 PBD and Plk3 PBD (see FIG. 5).

Example 4

Figure 6:
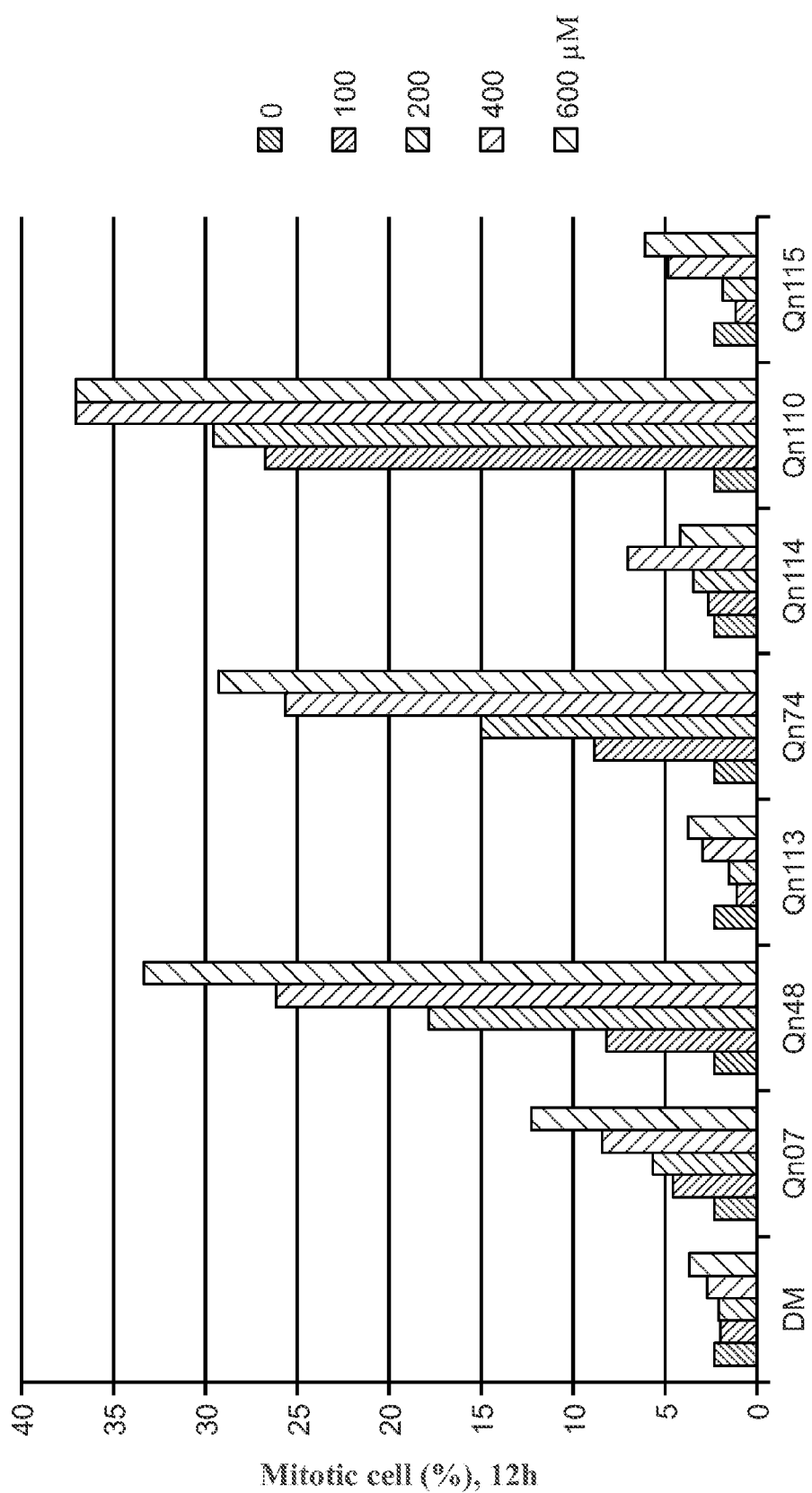
FIG. 6 shows induction of cell cycle arrest (mitotic block) by select compounds after 12 hours.
Figure 7:
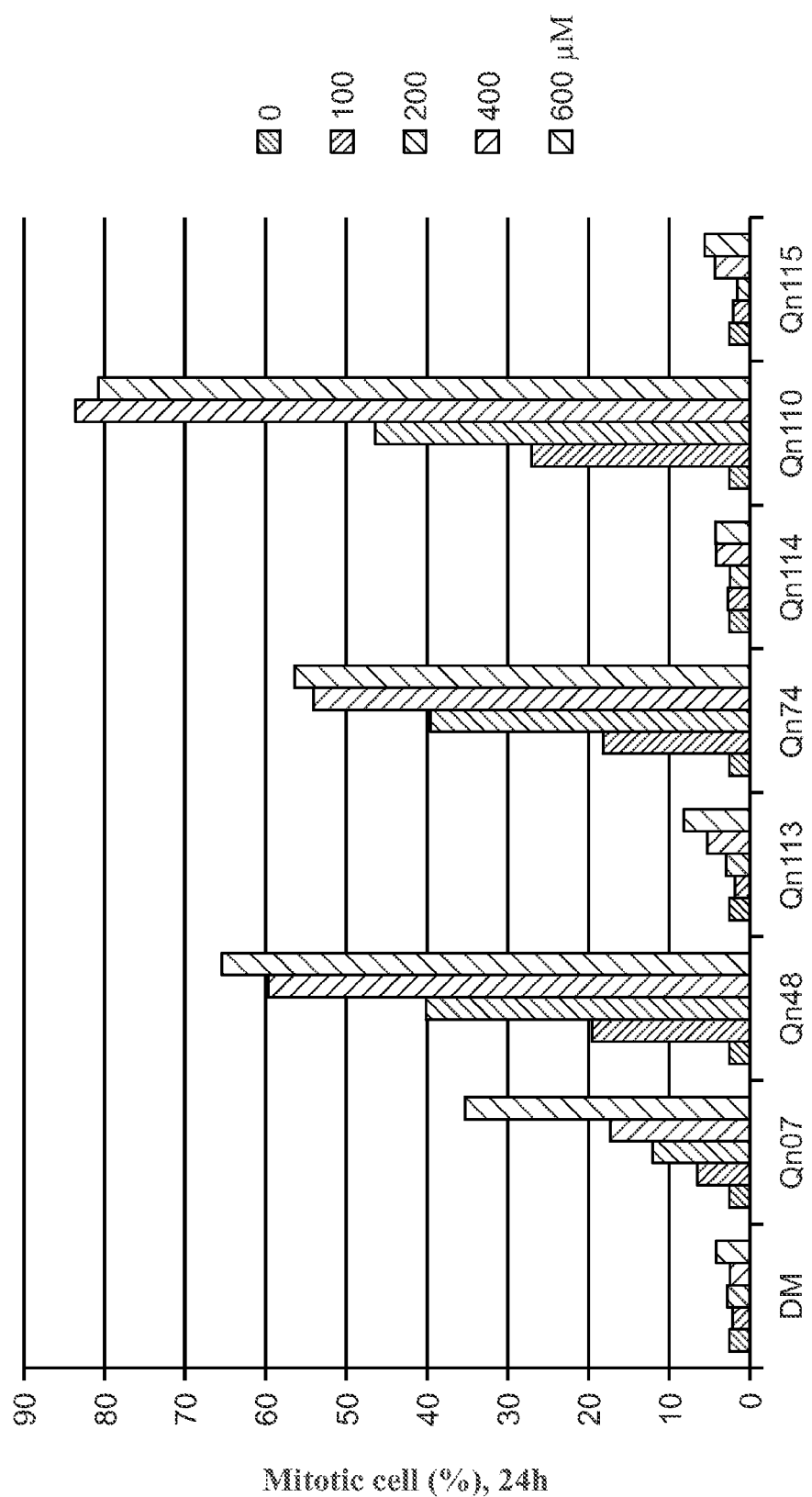
FIG. 7 shows induction of cell cycle arrest (mitotic block) by select compounds after 24 hours.
Figure 8A:
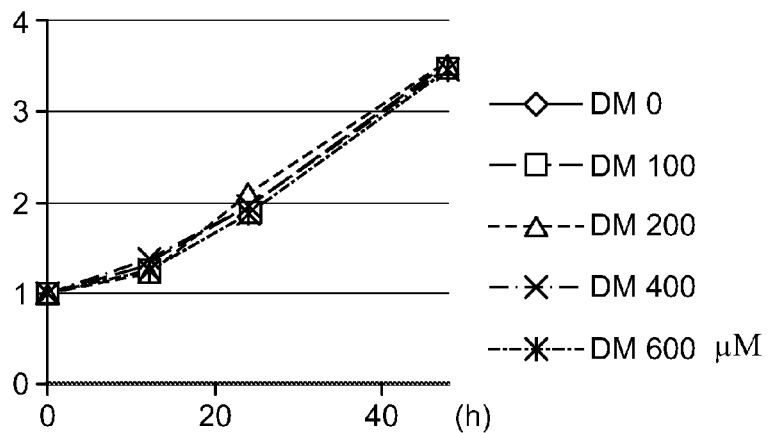
FIGS. 8 (*a-h*) are graphs showing inhibition of cell growth by select compounds at indicated concentrations.
Figure 8B:
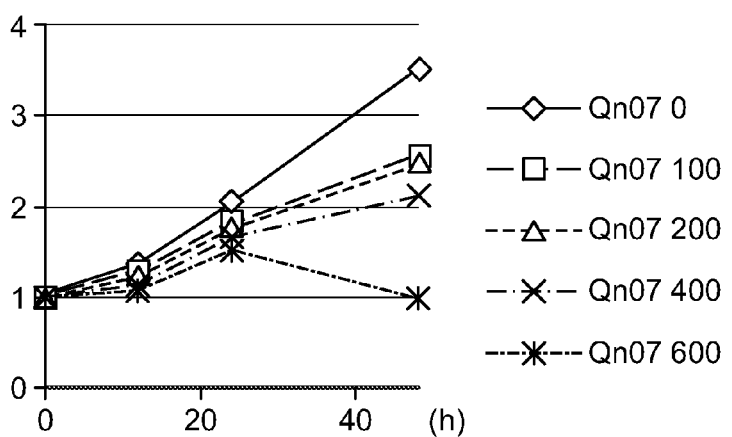
Figure 8C:
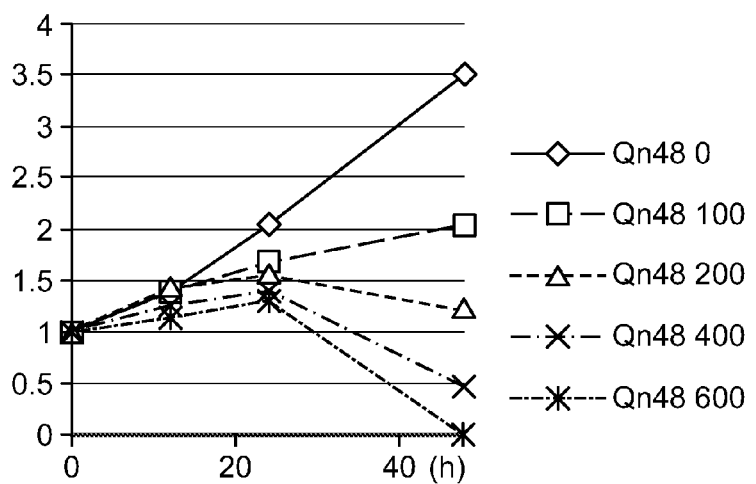
Figure 8D:
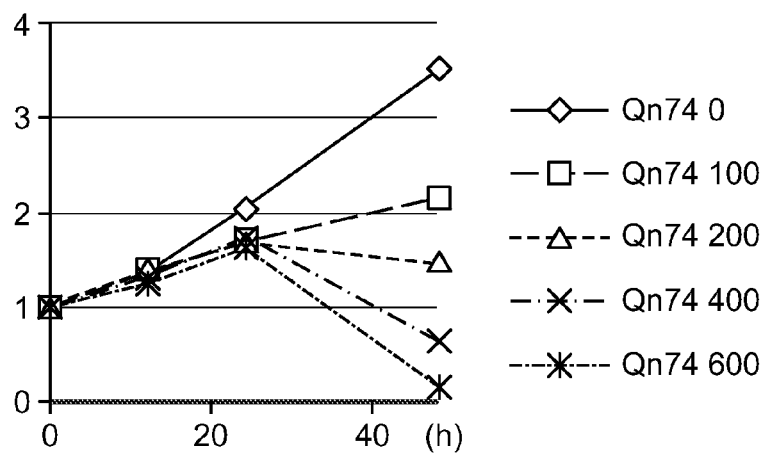
Figure 8E:
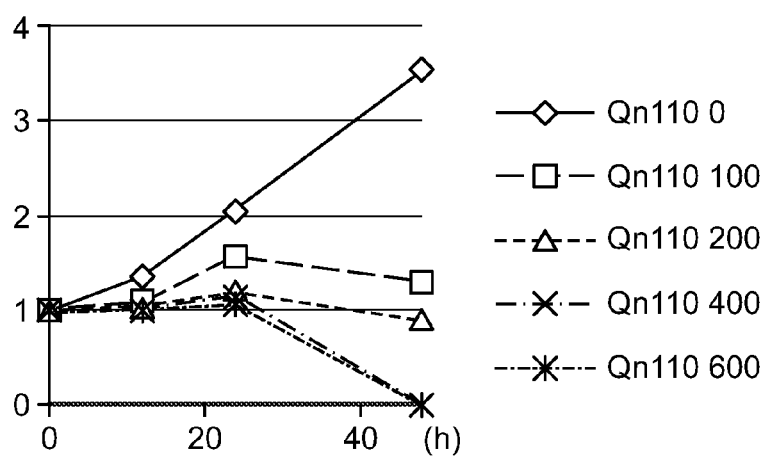
Figure 8F:
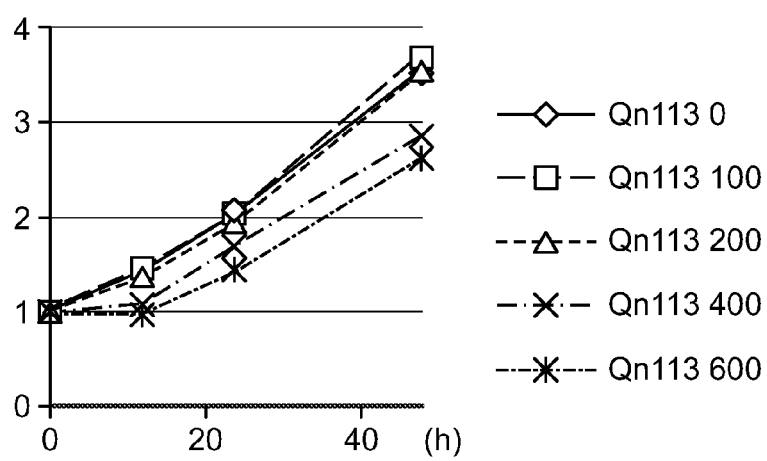
Figure 8G:
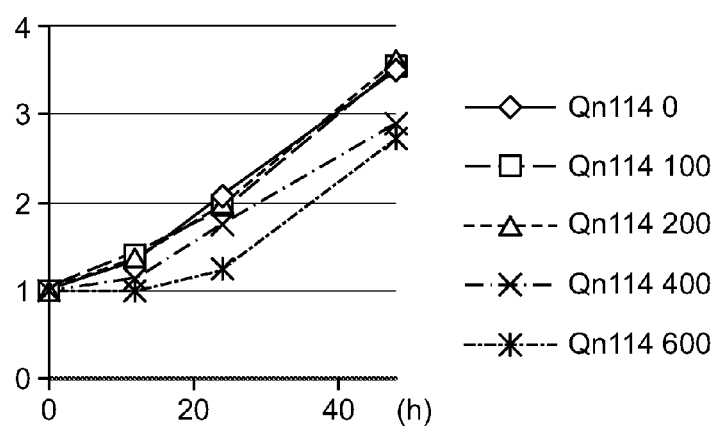
Figure 8H:
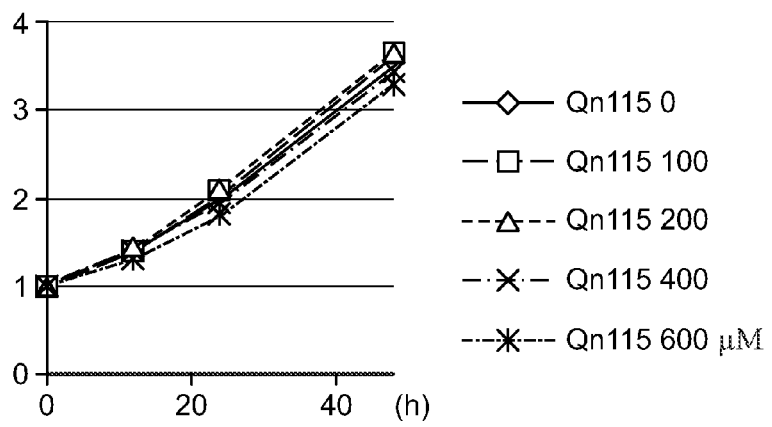
Figures 9, 9A:
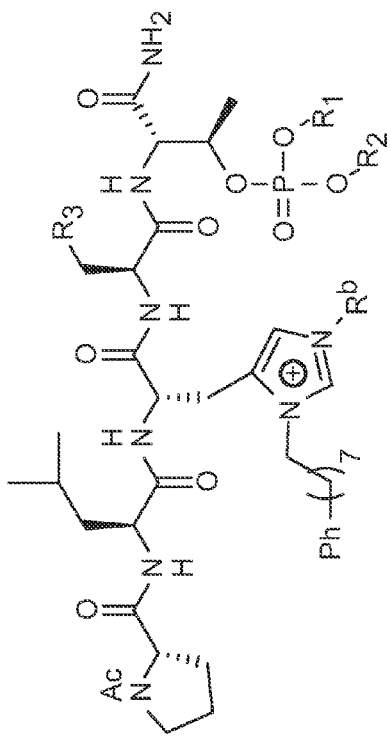
FIG. 9 is a table presenting PBD-binding IC$_{50}$ values for compounds provided in Table 2 infra.

Concentration Dependent Induction of Cell Cycle Arrest (Mitotic Block) by Selected Peptide Derivatives It has been observed that implementation of dual monoester/POM results in enhanced efficacy in whole cell studies, which is reflected in the dose-dependent ability to induce "mitotic block," leading to antiproliferative effects (see FIGS. 6 and 7).

FIG. 6 shows induction of cell cycle arrest (mitotic block) by selected compounds after 12 hours. FIG. 7 shows induction of cell cycle arrest (mitotic block) by selected compounds after 24 hours.

Example 5

Inhibition of Cell Growth by Selected Peptide Derivatives

Cell-based growth inhibition assays were performed. The results were shown in FIG. 8 (a-h) and also provided in Table 9.

TABLE 9

|  | Qn07 | Qn48 | Qn74 | Qn110 |
|---|---|---|---|---|
| $IC_{50}(\mu M)$ | 330 | 85 | 92 | 57 |

Those skilled in the art will recognize, or be able to ascertain using no more than routine experimentation, many equivalents to the specific embodiments of the invention described herein. Such equivalents are intended to be encompassed by the claims.

INCORPORATION BY REFERENCE

The entire contents of all patents, published patent applications and other references cited herein are hereby expressly incorporated herein in their entireties by reference.

REFERENCES

1. Blume-Jensen, P.; Hunter, T. Nature 2001, 411, 355-365;
2. Rogers, L. D.; Foster, L. J. Mol. BioSyst. 2009, 5, 1122-1129;
3. Yaffe, M. B. Nat. Rev. Mol. Cell Biol. 2002, 3, 177-186.
4. Ladbury, J. E. Protein Rev. 2005, 3, 165-184.
5. Elia, A. E. H.; Yaffe, M. B. In Modular Protein Domains; Cesare, G., Ed.; Wiley-VCH Verlag GmbH & Co. KGaA: Weinheim, Germany, 2005, p 163-179.
6. Eisele, F.; Owen, D. J.; Waldmann, H. Bioorg Med Chem 1999, 7, 193-224.
7. Allentoff, A.; Mandiyan, S.; Liang, H.; Yuryev, A.; Vlattas, I.; Duelfer, T.; Sytwu, I.-I.; Wennogle, L. Cell Biochem. Biophys. 1999, 31, 129-140.
8. Richter, S.; Bergmann, R.; Pietzsch, J.; Ramenda, T.; Steinbach, J.; Wuest, F. Biopolymers 2009, 92, 479-488.
9. Schultz, C. Bioorg. Med. Chem. 2003, 11, 885-898.
10. Mathe, C.; Perigaud, C.; Gosselin, G.; Imbach, J.-L. J. Org. Chem. 1998, 63, 8547-8550.
11. Liu, W.-Q.; Vidal, M.; Mathe, C.; Perigaud, C.; Garbay, C. Bioorg. Med. Chem. Lett. 2000, 10, 669-672.
12. Liu, W.-Q.; Vidal, M.; Olszowy, C.; Million, E.; Lenoir, C.; Dhotel, H.; Garbay, C. J. Med. Chem. 2004, 47, 1223-1233.
13. Rothman, D. M.; Vazquez, M. E.; Vogel, E. M.; Imperiali, B. J. Org. Chem. 2003, 68, 6795-6798.
14. Goguen, B. N.; Aemissegger, A.; Imperiali, B. J. Am. Chem. Soc. 2011, 133, 11038-11041.
15. Hecker, S. J.; Erion, M. D. J. Med. Chem. 2008, 51, 2328-2345.
16. Stankovic, C. J.; Surendran, N.; Lunney, E. A.; Plummer, M. S.; Para, K. S.; Shahripour, A.; Fergus, J. H.; Marks, J. S.; Herrera, R.; Hubbell, S. E.; Humblet, C.; Saltiel, A. R.; Stewart, B. H.; Sawyer, T. K. Bioorg. Med. Chem. Lett. 1997, 7, 1909-1914
17. Mandal, P. K.; Liao, W. S. L.; McMurray, J. S.; Org Lett. 2009, 11, 3394-3397.
18. Mandal, P. K.; Gao, F.; Lu, Z.; Ren, Z.; Ramesh, R.; Birtwistle, J. S.; Kaluarachchi, K. K.; Chen, X.; Bast, R. C.; Liao, W. S.; McMurray, J. S. J. Med. Chem. 2011, 54, 3549-3563.
19. Zhao, S.; Etzkorn, F. A. Bioorg. Med. Chem. Lett. 2007, 17, 6615-6618.
20. Ottinger, E. A.; Shekels, L. L.; Bernlohr, D. A.; Barany, G. Biochemistry 1993, 32, 4354-4361.
21. Hwang, Y.; Cole, P. A. Org. Lett. 2004, 6, 1555-1556.
22. McMurray, J. S.; Coleman, D. R. I. V.; Wang, W.; Campbell, M. L. Biopolymers 2001, 60, 3-31.
23. Attard, T. J.; O'Brien-Simpson, N.; Reynolds, E. C. Int. J. Pept. Res. Ther. 2007, 13, 447-468.
24. Toth, G. K.; Kele, Z.; Varadi, G.; Curr. Org. Chem. 2007, 11, 409-426.
25. Yun, S.-M.; Moulaei, T.; Lim, D.; Bang, J. K.; Park, J.-E.; Shenoy, S. R.; Liu, F.; Kang, Y. H.; Liao, C.; Soung, N.-K.; Lee, S.; Yoon, D.-Y.; Lim, Y.; Lee, D.-H.; Otaka, A.; Appella, E.; McMahon, J. B.; Nicklaus, M. C.; Burke, T. R., Jr.; Yaffe, M. B.; Wlodawer, A.; Lee, K. S. Nat. Struct. Mol. Biol. 2009, 16, 876-882.
26. Lu, C. H. S.; Liu, K.; Tan, L. P.; Yao, S. Q. Chem. Eur. J. 2012, 18, 28-39.
27. Burke, T. R., Jr.; Lee, K. Acc. Chem. Res. 2003, 36, 426-433.
28. (a) Shapiro, G.; Buechler, D.; Ojea, V.; Pombo-Villar, E.; Ruiz, M.; Weber, H. P. Tetrahedron Lett. 1993, 34, 6255-6258; (b) Perich, J. W. Int. J. Pept. Protein Res. 1994, 44, 288-294; (c) Nair, S. A.; Lee, B.; Hangauer, D. G. Synthesis 1995, 810-814; (d) Panigrahi, K.; Eggen, M.; Maeng, J.-H.; Shen, Q.; Berkowitz, D. B. Chem. Biol. 2009, 16, 928-936.
29. (a) Otaka, A.; Mitsuyama, E.; Kinoshita, T.; Tamamura, H.; Fujii, N. J. Org. Chem. 2000, 65, 4888-4899; (b) Liu, F.; Park, J.-E.; Lee, K. S.; Burke, T. R., Jr. Tetrahedron 2009, 65, 9673-9679.
30. Boutselis, I. G.; Yu, X.; Zhang, Z.-Y.; Borch, R. F. J. Med. Chem. 2007, 50, 856-864. A M 30308628.1
31. Arrendale, A.; Kim, K.; Choi, J.; Li, W.; Geahlen, R. L.; Borch, R. F. Chem. BioL 2012, 19, 764-771.
32. (a) Stankovic, C. J.; Surendran, N.; Lunney, E. A.; Plummer, M. S.; Para, K. S.; Shahripour, A.; Fergus, J. H.; Marks, J. S.; Herrera, R.; Hubbell, S. E.; Humblet, C.; Saltiel, A. R.; Stewart, B. H.; Sawyer, T. K. Bioorg. Med. Chem. Lett. 1997, 7, 1909-1914; (b) Mandal, P. K.; Liao, W. S. L.; McMurray, J. S. Org. Lett. 2009, 11, 3394-3397; (c) Mandal, P. K.; Gao, F.; Lu, Z.; Ren, Z.; Ramesh, R.; Birtwistle, J. S.; Kaluarachchi, K. K.; Chen, X.; Bast, R. C.; Liao, W. S.; McMurray, J. S. J. Med. Chem. 2011, 54, 3549 3563; (d) Zhao, S.; Etzkorn, F. A. Bioorg. Med. Chem. Lett. 2007, 17, 6615-6618.
33. (a) Yun, S.-M.; Moulaei, T.; Lim, D.; Bang, J. K.; Park, J.-E.; Shenoy, S. R.; Liu, F.; Kang, Y. H.; Liao, C.; Soung, N.-K.; Lee, S.; Yoon, D.-Y.; Lim, Y.; Lee, D.-H.; Otaka, A.; Appella, E.; McMahon, J. B.; Nicklaus, M. C.; Burke, T. R., Jr.; Yaffe, M. B.; Wlodawer, A.; Lee, K. S. Nat. Struct. Mol. Biol. 2009, 16, 876-882; (b) Liu, F.; Park, J.-E.; Qian, W. J.; Lim, D.; Gruber, M.; Berg, T.; Yaffe, M. B.; Lee, K. S.; Burke, T. R., Jr. Nat. Chem. Biol. 2011, 7, 595-601; (c) Liu, F.; Park, J.-E.; Qian, W.-J.; Lim, D.; Scharow, A.; Berg, T.; Yaffe, M. B.; Lee, K. S.; Burke, T. R., Jr. ChemBioChem 2012, 13, 1291-1296.

34. van de Weerdt, W. B. C. M.; Littler, D. R.; Klompmaker, R.; Huseinovic, A.; Fish, A.; Perrakis, A.; Medema, R. H. *Biochim. Biophys. Acta, Mol. Cell Res.* 2008, 1783, 1015-1022
35. (a) *Nat. Struct. Mol. Biol.* 2009, 16, 876-882; (b) *Nat. Chem. Biol.* 2011, 7, 595-601; (c) *ACS Chem. Biol.* 2012, 7, 805-810; (d) *ChemBioChem* 2012, 13, 1291-1296
36. U.S. Patent Publication No. 2012/0065146 A1.
37. PCT Patent Publication No. WO2010132869 A2.
38. PCT Patent Publication No. WO2012142245 A2.

We claim:

1. A compound of Formula (A'):

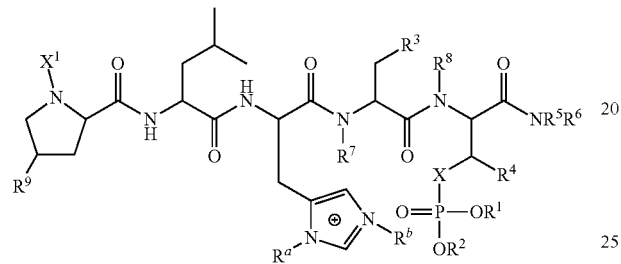

(A')

wherein
X is O, —($C_{1-6}$)alkyl-, or —C(Y)$_2$—; wherein Y, for each occurrence independently, is F, Cl, or Br;
$X^1$ is H, ($C_{1-6}$)alkyl-C(O)—, or a polyethylene glycol moiety or a derivative thereof;
$R^1$ and $R^2$, each independently, are selected from the group of H, ($C_{1-6}$)alkyl-C(O)O—($C_{1-6}$)alkyl-, ($C_{1-20}$)alkyl, aryl-($C_{1-20}$)alkyl-, heteroaryl-($C_{1-20}$)alkyl, $X^2$O—C(O)—($C_{1-6}$)alkyl-, and amino($C_{1-6}$)alkyl, wherein each alkyl moiety that appears at the $R^1$ and $R^2$ positions is further optionally substituted by one or more carboxyl, hydroxyl, or alkoxy groups, and wherein $R^1$ and $R^2$ cannot both be H;
$X^2$ is H or ($C_{1-6}$)alkyl; wherein the ($C_{1-6}$)alkyl is optionally substituted by one or more hydroxyl, halo, or alkoxy groups;
$R^3$ is H, —OH, ($C_{1-6}$)alkyl-C(O)O—, or ($C_{1-6}$)alkoxy;
$R^4$ is H, acyl, ($C_{1-6}$)alkyl-OC(O)O—, or ($C_{1-6}$)alkyl-O—C(S)—O—;
$R^5$ and $R^6$, each independently, are selected from the group of H, ($C_{1-6}$)alkyl-C(O)—, ($C_{1-6}$)alkoxy-($C_{1-6}$)alkyl, $X^3$=N—O—($C_{1-6}$)alkyl, an amino acid, and a glycine moiety;
wherein $X^3$ is derived from a sugar moiety;
$R^a$ is H, aryl-($C_{1-20}$)alkyl, heteroaryl-($C_{1-20}$)alkyl, ($C_{1-20}$)alkyl, allyl-($C_{1-20}$)alkyl, ($C_{0-20}$)alkoxy-C(O)—($C_{1-20}$)alkyl, or amino($C_{1-20}$)alkyl; wherein each of the said alkyl, aryl, and heteroaryl moieties is further optionally substituted by one or more same or different subtituents selected from the group of ($C_{1-6}$)alkyl, carboxyl, halo, hydroxyl, amine, and ($C_{1-6}$)alkoxy groups;
$R^b$ is a member selected from the group of allyl-($C_{1-6}$)alkyl, aryl-($C_{1-6}$)alkyl-, heteroaryl-($C_{1-6}$)alkyl, and ($C_{1-6}$)alkyl optionally substituted by one or more carboxyl, ($C_{1-6}$)alkoxyl, or hydroxyl groups;
$R^7$ and $R^8$, each independently, are selected from the group of H, ($C_{1-6}$)alkyl, and ($C_{1-6}$)alkyl-C(O)—; and
$R^9$ is a bond, R', R'—CH=N—O—, R'—($C_{1-6}$)alkyl-O—, R'—C(O)—NH—O—, R'—($C_{1-6}$)alkyl-S—, or R'—($C_{1-6}$)alkyl;

R' is H, ($C_{1-6}$)alkyl, halo, amino-O—, ($C_{1-6}$)alkyl-C(O)—, ($C_{2-6}$)alkenyl, cycloalkyl, heterocyclic, aryl-($C_{0-6}$)alkyl, or heretoaryl-($C_{0-6}$)alkyl, wherein each of said alkyl, cycloalkyl, heterocyclic, aryl and heteroaryl moieties is optionally substituted by one or more same or different substituents selected from the group of aryl, heteroaryl, hydroxyl, hydrosulfide, alkyl, alkoxy, alkenyl, halogen, nitro, cyano, ester, amine, amide, carboxyl, and alkyl-carbonyl groups;
or a pharmaceutically acceptable salt, solvate, hydrate, or stereoisomer thereof.

2. The compound of any one of claim 1, wherein $X^1$ is $CH_3C(O)$—, and $R^7$ and $R^8$ are both H.

3. The compound of claim 1 wherein said compound is a compound of Formula (B'):

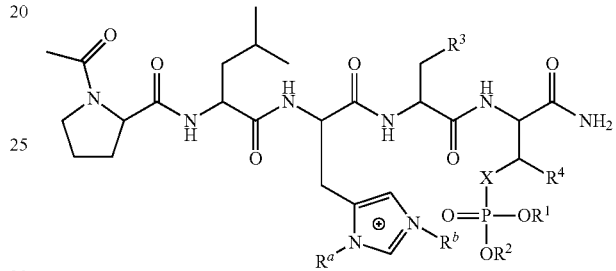

(B')

Wherein
X is O or $CH_2$;
one of $R^1$ and $R^2$ is ($C_{1-6}$)alkyl-C(O)O—($C_{1-6}$)alkyl- or H, and the other is selected from the group of H, ($C_{1-6}$)alkyl, allyl-($C_{1-6}$)alkyl-, aryl-($C_{1-6}$)alkyl-, ($C_{1-6}$)alkyl-C(O)O—($C_{1-6}$)alkyl-, and heteroaryl-($C_{1-6}$)alkyl-; wherein each alkyl moiety is further optionally substituted by one or more carboxyl, hydroxyl, or ($C_{1-6}$)alkoxy groups, and wherein $R^1$ and $R^2$ cannot both be H;
$R^3$ is H, —OH, ($C_{1-6}$)alkyl, ($C_{1-6}$)alkyl-C(O)O—, or ($C_{1-6}$)alkoxy;
$R^4$ is H or ($C_{1-6}$)alkyl; and
$R^a$ is H, aryl-($C_{1-10}$)alkyl, aryl-($C_{1-10}$)alkyl, or heteroaryl-($C_{1-10}$)alkyl; wherein each of the said alkyl, aryl, and heteroaryl moieties is further optionally substituted by one or more same or different substituents selected from the group of carboxyl, hydroxyl, and ($C_{1-6}$)alkoxy;
$R^b$ is a member selected from the group of allyl-($C_{1-6}$)alkyl, aryl-($C_{1-6}$)alkyl-, heteroaryl-($C_{1-6}$)alkyl, and ($C_{1-6}$)alkyl optionally substituted by one or more carboxyl, ($C_{1-6}$)alkoxyl, or hydroxyl groups;
or a pharmaceutically acceptable salt, solvate, hydrate, or stereoisomer thereof.

4. The compound of claim 3, wherein one of $R^1$ and $R^2$ is ($C_{1-6}$)alkyl-C(O)O—($C_{1-6}$)alkyl-, and the other is selected from the group of H, ($C_{1-6}$)alkyl-C(O)O—($C_{1-6}$)alkyl-, aryl-($C_{1-6}$)alkyl-, and ($C_{1-6}$)alkyl optionally substituted by one or more hydroxyl groups.

5. The compound of claim 4, wherein one of $R^1$ and $R^2$ is t-Bu-C(O)O—$CH_2$— ("POM"), and the other is selected from the group of H, t-Bu-C(O)O—$CH_2$—, —($CH_2$)$_2$OH, and benzyl.

6. The compound of claim 3, wherein $R^3$ is H or —OH.

7. The compound of claim 3, wherein $R^a$ is phenyl-$(C_{1-10})$alkyl.

8. The compound of claim 3, wherein $R^b$ is $(C_{1-6})$alkyl optionally substituted by one or more $(C_{1-6})$alkoxyl or hydroxyl groups.

9. The compound of claim 3, wherein $R^4$ is $(C_{1-6})$alkyl.

10. The compound of claim 3, wherein said compound is selected from the group consisting of Compound Nos. A10-A12 as provided in Table 1:

TABLE 1

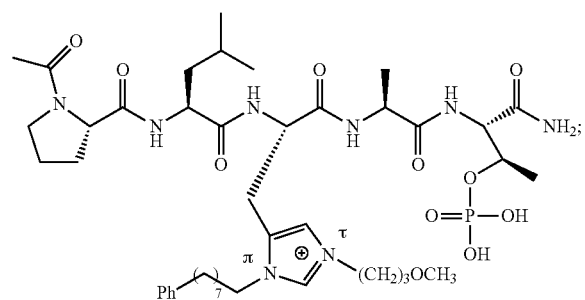

| Comp. No. | X | $R^1$ | $R^2$ | $R^3$ | $R^a$ | $R^b$ |
|---|---|---|---|---|---|---|
| A10 | O | POM | H | OH | Ph(CH$_2$)$_8$— | ⌇⌇⌇⌇OH (butyl-OH) |
| A11 | O | POM | H | H | Ph(CH$_2$)$_8$— | ⌇⌇⌇⌇OH (butyl-OH) |
| A12 | O | POM | H | OH | H | ⌇⌇⌇⌇OH (butyl-OH) | or a pharmaceutically acceptable salt, solvate, hydrate, or stereoisomer thereof.

11. The compound of claim 3, wherein one of $R^1$ and $R^2$ is H, and the other is selected from the group of allyl-$(C_{1-6})$alkyl, aryl-$(C_{1-6})$alkyl-, heteroaryl-$(C_{1-6})$alkyl, and $(C_{1-6})$alkyl optionally substituted by one or more carboxyl or hydroxyl groups.

12. The compound of claim 3, wherein $R^3$ is H.

13. The compound of claim 3, wherein $R^a$ is aryl-$(C_{1-10})$ alkyl.

14. The compound of claim 3, wherein, $R^b$ is $(C_{1-6})$alkyl optionally substituted by one or more carboxyl, $(C_{1-6})$ alkoxyl, or hydroxyl groups.

15. The compound of claim 3, wherein said compound is selected from the group consisting of:

Compound No. A14

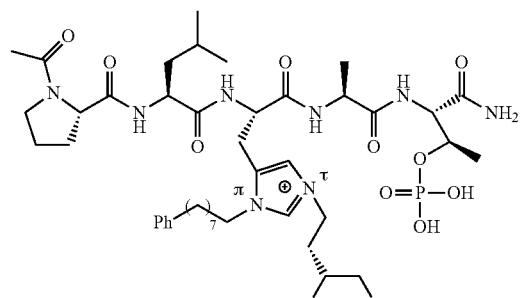

Compound No. A15

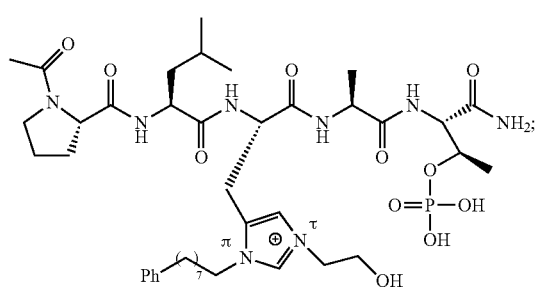

Compound No. A16

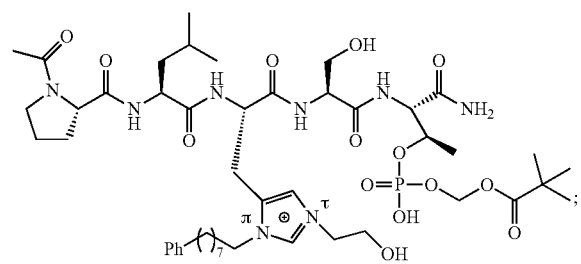

and
or a pharmaceutically acceptable salt, solvate, hydrate, or stereoisomer thereof.

16. The compound of claim 3, wherein said compound is

Compound No. A10 or a pharmaceutically acceptable salt, solvate, hydrate, or stereoisomer thereof.

17. A pharmaceutical composition comprising compound of claim 1, and a pharmaceutically acceptable carrier.

18. A kit comprising at least one compound of claim 1 and instructions for use.

19. A chemical library including two or more compounds of claim 1.

20. The compound of claim 1, wherein X is selected from the group consisting of O, CH$_2$, and CF$_2$.

21. The compound of claim 1, wherein $X^1$ is H or $(C_{1-6})$alkyl-C(O)—.

22. The compound of claim 1, wherein at least one of $R^1$ and $R^2$ is $(C_{1-6})$alkyl-C(O)O—$(C_{1-6})$alkyl- or H, and the other is selected from the group of H, $(C_{1-6})$alkyl, allyl-$(C_{1-6})$alkyl, aryl-$(C_{1-6})$alkyl-, $(C_{1-6})$alkyl-C(O)O—$(C_{1-6})$ alkyl-, and heteroaryl-$(C_{1-6})$alkyl-; wherein each alkyl moiety is further optionally substituted by one or more carboxyl, hydroxyl, or $(C_{1-6})$alkoxy groups.

23. The compound of claim 1, wherein $R^4$ is selected from the group of H, acyl, and $(C_{1-6})$alkyl.

24. The compound of claim 1, wherein $R^5$ and $R^6$ are each independently selected from the group consisting of H, $(C_{1-6})$alkyl, $(C_{1-6})$alkyl-C(O)—, and $(C_{1-6})$alkoxy-$(C_{1-6})$alkyl.

25. The compound of claim 1, wherein $R^9$ is selected from the group consisting of H, halo, $(C_{2-6})$alkenyl-$(C_{1-6})$alkyl-O—, aryl-$(C_{1-6})$alkyl-CH=N—O—, heteroaryl-$(C_{1-6})$alkyl-CH=N—O—, and $(C_{1-6})$alkyl, wherein each of said alkyl, aryl and heteroaryl moieties is optionally substituted by one or more same or different substituents selected from the group of aryl, heteroaryl, hydroxyl, alkyl, alkoxy, alkenyl, halogen, nitro, cyano, ester, amine, amide, carboxyl, and alkyl-carbonyl groups.

26. A method for the amelioration, or treatment of a hyperproliferative disorder comprising administering to a subject in need thereof a composition comprising an effective amount of a compound of claim 1.

27. The method of claim 26, wherein the method further includes the step of identifying of a subject suffering from or suspected of suffering from a hyperproliferative disorder.

28. The method of claim 27, further comprising the step of monitoring the subject for amelioration, or treatment of a hyperproliferative disorder.

29. The method of claim 26, wherein the hyperproliferative disorder comprises cancer.

30. The method of claim 29, wherein the cancer is selected from the group consisting of Acute Lymphoblastic Leukemia, Acute Myeloid Leukemia, Adrenocortical Carcinoma, Basal Cell Carcinoma, Bladder Cancer, Bone Cancer, Brain Tumor, Breast Cancer, Cervical Cancer, Chronic Lymphocytic Leukemia, Chronic Myelogenous Leukemia, Chronic Myeloproliferative Disorders, Colon Cancer, Colorectal Cancer, Cutaneous T-Cell Lymphoma, Esophageal Cancer, Ewing Family of Tumors, Retinoblastoma, Gastric Cancer, Gastrointestinal Tumors, Glioma, Head and Neck Cancer, Hepatocellular Cancer, Hodgkin Lymphoma, Islet Cell Tumors, Kidney Cancer, Laryngeal Cancer, Non-Small Cell Lung Cancer, Small Cell Lung Cancer, Lymphoma, Medulloblastoma, Melanoma, Pancreatic Cancer, Prostate Cancer, Renal Cancer, Rectal Cancer, and Thyroid Cancer.

* * * * *